United States Patent
Tamareselvy et al.

(10) Patent No.: US 7,378,479 B2
(45) Date of Patent: May 27, 2008

(54) MULTI-PURPOSE POLYMERS, METHODS AND COMPOSITIONS

(75) Inventors: Krishnan Tamareselvy, Brecksville, OH (US); Thomas A. Barker, Akron, OH (US); James E. Mullee, Garrettsville, OH (US); Charles T. Greenslade, Willoughby, OH (US); Julie F. Schmucker-Castner, Strongsville, OH (US); Deborah S. Filla, Twinsburg, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 608 days.

(21) Appl. No.: 10/646,856

(22) Filed: Aug. 22, 2003

(65) Prior Publication Data

US 2004/0052746 A1   Mar. 18, 2004

Related U.S. Application Data

(60) Provisional application No. 60/410,697, filed on Sep. 13, 2002.

(51) Int. Cl.
*C08F 216/12* (2006.01)
*C08F 220/10* (2006.01)
*C08F 20/52* (2006.01)

(52) U.S. Cl. ............ 526/333; 526/303.1; 526/304; 526/307.2; 526/307.5; 526/307.7; 526/312; 526/320; 526/328.5; 526/329.6; 526/332

(58) Field of Classification Search ............ 526/303.1, 526/304, 307.2, 307.5, 307.7, 312, 320, 328.5, 526/329.6, 332, 333
See application file for complete search history.

(56) References Cited

U.S. PATENT DOCUMENTS

| | | | |
|---|---|---|---|
| 4,275,055 A | | 6/1981 | Nachtigal et al. |
| 4,728,696 A | * | 3/1988 | Van Phung et al. ......... 526/304 |
| 4,777,037 A | | 10/1988 | Wagman et al. |
| 4,801,671 A | | 1/1989 | Shay et al. |
| 5,073,372 A | | 12/1991 | Turner et al. |
| 5,164,177 A | | 11/1992 | Bhatt et al. |
| 5,292,843 A | * | 3/1994 | Jenkins et al. ........... 526/318.5 |
| 5,376,364 A | | 12/1994 | Darkwa et al. |
| 5,376,709 A | | 12/1994 | Lau et al. |
| 5,599,549 A | | 2/1997 | Wivell et al. |
| 5,639,841 A | * | 6/1997 | Jenkins ....................... 526/333 |
| 5,708,068 A | * | 1/1998 | Carder et al. ............... 524/375 |
| 5,874,095 A | | 2/1999 | Deckner et al. |
| 5,883,085 A | | 3/1999 | Blank et al. |
| 5,948,416 A | | 9/1999 | Wagner et al. |
| 5,997,764 A | | 12/1999 | Ambuter et al. |
| 6,025,431 A | | 2/2000 | Cardinali et al. |
| 6,190,647 B1 | | 2/2001 | Karten et al. |
| 6,268,431 B1 | | 7/2001 | Snyder et al. |
| 6,271,192 B1 | | 8/2001 | Verstrat et al. |
| 6,274,129 B1 | | 8/2001 | Bhatt et al. |
| 6,274,539 B1 | | 8/2001 | Kacher et al. |
| 6,290,943 B1 | | 9/2001 | Naser et al. |
| 6,299,866 B1 | | 10/2001 | Liu et al. |
| 6,319,489 B1 | | 11/2001 | Ashton et al. |
| 6,329,483 B1 | | 12/2001 | Schade et al. |
| 6,346,234 B1 | | 2/2002 | Rollat et al. |
| 6,361,768 B1 | | 3/2002 | Galleguillos et al. ..... 424/70.12 |
| 6,440,431 B1 | | 8/2002 | Yoshida et al. |
| 2001/0003581 A1 | | 6/2001 | Chang et al. |
| 2001/0014313 A1 | | 8/2001 | Roulier et al. |
| 2001/0016617 A1 | | 8/2001 | Reeve |
| 2001/0046952 A1 | | 11/2001 | Verstrat et al. |
| 2001/0055580 A1 | | 12/2001 | Belli et al. |
| 2002/0004035 A1 | | 1/2002 | Bhatt et al. |

FOREIGN PATENT DOCUMENTS

| | | | |
|---|---|---|---|
| EP | 0 398 576 | * | 11/1990 |
| EP | 0 444 791 A1 | * | 9/1991 |
| EP | 0824914 | | 2/1998 |
| EP | 0825200 | | 2/1998 |
| FR | 2 777 011 | | 10/1999 |
| WO | WO 00/40628 | | 7/2000 |

OTHER PUBLICATIONS

Raymond Rigoletto, Jr., et al., "Styleze 2000, A New Fixative Polymer for Gels-Formultaion and Processing Guide Part I," Soap & Cosmetics, pp. 43-46, (Jul./Aug. 2001).
Raymond Rigoletto, Jr., et al., "Styleze 2000, A New Fixative Polymer for Gels-Formulation and Processing Guide Part II," Soap & Cosmetics, pp. 39-43, (Sep. 2001).
"Standard Test Method for Specular Gloss", ASTM Designation: D523-89, pp. 32-36 (Reapproved 1994).
P. Reeve, "Tailoring the Properties of Polymeric Rheology Modifiers. . . ," Proceedings of International Federation of Society of Cosmetic Chemists, IFSCC, Budapest, pp. 337-347 (Apr. 1997).
C. E. Jones, "A Study of the Interaction of Hydrophobically-Modified Polyols with Surfactants," Proceedings of 4th Surfactants Congress, Barcelona, vol. 2, pp. 439-450 (1996).

(Continued)

*Primary Examiner*—Helen L Pezzuto
(74) *Attorney, Agent, or Firm*—Thoburn T. Dunlap; Delores T. Kenney

(57) ABSTRACT

Disclosed are multi-purpose polymers that are the polymerization product of a monomer mixture comprising at least one amino-substituted vinyl monomer; at least one nonionic vinyl monomer; at least one associative vinyl monomer; at least one semihydrophobic vinyl surfactant monomer; and, optionally, comprising one or more hydroxy-substituted nonionic vinyl monomer, crosslinking monomer, chain transfer agent or polymeric stabilizer. These vinyl addition polymers have a combination of substituents, including amino substituents that provide cationic properties at low pH, hydrophobic substituents, hydrophobically modified polyoxyalkylene substituents, and hydrophilic polyoxyalkylene substituents. The polymers provide surprisingly beneficial rheological properties in acidic aqueous compositions, and are compatible with cationic materials. The multi-purpose polymers are useful in a variety of products for personal care, health care, household care, institutional and industrial care, and industrial applications.

29 Claims, No Drawings

OTHER PUBLICATIONS

K. C. Tam, et al., "Rheological and Microcalorimetric Studies of a Model Alkali-Soluble Associative Polymer (HASE) . . . ", Journal of Polymer Science: Part B, vol. 38, pp. 2019-2032 (2000).

Anthony L. L. Hunting, "Shampoo Thickeners," Cosmetics & Toiletries, vol. 97, pp. 53-63 (Mar. 1982).

"Standard Guide for Descriptive Analysis of Shampoo Performance," ASTM Designation: E2082-00, pp. 1-10 (2000).

Kenneth A. Kasprazak, "Volatile Silicones, New Cleaners for Oils and Greases," Soap/Cosmetics/Chemical Specialities, pp. 40-43 (Dec. 1986).

Charles Todd, et al., "Volatile Silicone Fluids for Cosmetic Formulations," Cosmetics and Toiletries, vol. 91 pp. 29-32, (Jan. 1976).

George R. Whalley, "Fabric Conditioning Agents," HAPPI, pp. 55-58 (Feb. 1995).

J. Jachowicz, et al., "Effect of Alkyl Substitution on Styling and Conditioning . . . ", IFSCC Magazine, vol. 5, pp. 1-17 (2002).

George V. Scott, et al., "Sorption of Quaternary Ammonium Surfactants by Human Hair," J. Soc. Cosmetic Chemists, vol. 20, pp. 135-152 (Feb. 5, 1969).

Research Disclosure, Kenneth Mason Publications, Hampshire, GB, vol. 428, Dec. 1999, "Application of Acrylates/Methacrylates/Beheneth-25 Methacrylate Copolymer (Aculyn® 28) As A Thickener And Suspending Agent In Cosmetic Formulations And As A Polymeric Emulsifier", pp. 1553-1554.

* cited by examiner

MULTI-PURPOSE POLYMERS, METHODS AND COMPOSITIONS

CROSS-REFERENCE TO RELATED APPLICATION

This application claims the priority of U.S. Provisional Application Ser. No. 60/410,697, filed on Sep. 13, 2002, which is incorporated herein by reference.

TECHNICAL FIELD OF THE INVENTION

This invention relates to the field of polymers, and in particular, to cationic polymers and associative polymers.

BACKGROUND OF THE INVENTION

Formulations having an acidic pH, (i.e., <7), containing cationic components, such as cationic surfactants and salts thereof or active acidic components are commonly referred to as "low pH" formulations. Stable low pH viscous emulsion and gel formulations are difficult to obtain. Most commonly used thickeners are synthetic associative thickeners that are frequently anionic and hence typically are incompatible with the cationic component, especially quaternary ammonium salts, or are ineffective thickeners at low pH.

Consequently, the formulator of low pH compositions, especially emulsions, has a limited choice of either nonionic thickeners, such as nonionic surfactants, or cationic thickeners. Nonionic thickeners are uncharged and thus are assumed to be less reactive, but nonionics tend to inactivate preservatives and in some cases promote microbial growth. While some cationic polymeric rheology modifiers, such as hydrophobically modified aminoacrylate copolymers, are available commercially, their theological properties are unpredictable, or aesthetically unsatisfactory.

Thus, there is an ongoing need and desire for a cationic compatible polymeric rheology modifier for low pH formulations.

SUMMARY OF THE INVENTION

The present invention provides multi-purpose polymers, which have generally cationic and associative characteristics.

The polymers of the present invention are multifunctional vinyl addition polymers having a combination of amino substituents that provide hydrophilicity and cationic properties at low pH, hydrophobic substituents to attenuate the hydrophilicity, hydrophobically modified polyoxyalkylene substituents that provide associative properties, and hydrophilic polyoxyalkylene substituents that attenuate the associative properties and provide beneficial rheological properties. The polymers are produced by polymerization of a monomer mixture comprising at least one amino-substituted vinyl monomer; at least one hydrophobic nonionic vinyl monomer; at least one associative vinyl monomer; at least one semihydrophobic vinyl surfactant monomer; and, optionally, comprising one or more hydroxy-substituted nonionic vinyl monomer, crosslinking monomer, chain transfer agent, polymeric stabilizer, and the like.

The polymers can swell upon acidification with either inorganic acid or organic acid, including amino acid, or upon alkylation, or by both acidification and alkylation. The inventive, multi-purpose polymers can be employed as thickeners, emulsifiers, stabilizers, suspending agents, film formers, conditioners, moisturizers, spreading aids and carriers for enhancing the efficacy, deposition or delivery of chemically and physiologically active ingredients and cosmetic materials, and as vehicles for improving the psychosensory, and aesthetic properties of a formulation in which they are included. The cationic character of the polymers at low pH makes them useful as antistatic agents, and, under certain conditions, may also provide biocidal, anti-microbial, or other preservative activity.

The polymers of the present invention beneficially can thicken acidic aqueous formulations to provide aesthetically smooth-textured products that flow smoothly and spread easily. The form of a polymer containing product can range from a non-pourable, stiff to soft gel, a semisolid paste to a substantially solid stick or bar, and aerosolized foam to squeezable gel, as well as a non-runny, yet flowable, product, suitable for pumpable spray or roll-on products and liquid lotions. The inventive polymers are surprisingly effective at thickening aqueous systems containing cationic ingredients (e.g., quaternary ammonium compounds and amines), cationic conditioning agents, fabric softeners, surfactants, and the like.

Advantageously, the polymers of this invention can be employed, without being limited thereto, in personal care products, health care products, household care products, institutional and industrial (collectively "I&I") care products, and the like. The polymers can be employed as a film forming conditioner, and for promoting the deposition of color cosmetics and of polar and non-polar oils on skin, hair, or both. Further, the polymers can be employed in products for industrial chemical processes, textile finishing processes, printing, adhesive coating, and like applications as, for example, rheology modifiers, emulsifiers, stabilizers, solubilizers, suspending agents, flocculents, and pigment and grinding additives.

DESCRIPTION OF THE PREFERRED EMBODIMENTS

The polymers of the present invention are generally basic, aqueous acid-swellable, or aqueous acid-soluble, polymers, and salts thereof, which contain at least one basic amino substituent that is cationic at low pH, at least one hydrophobically modified polyoxyalkylene substituent derived from an associative vinyl monomer, and at least one polyoxyalkylene substituent derived from a semihydrophobic vinyl surfactant monomer. The polymer of the present invention can also optionally contain substituent groups derived from other monomer units, such as crosslinking monomer units, hydroxy-substituted nonionic vinyl monomer units, chain transfer agent units, polymeric stabilizers, and the like. The polymers of the present invention generally exhibit associative properties in aqueous solution. For convenience, the polymers of the present invention are generally referred to herein as "cationic associative polymers." The term "low pH formulation" refers to formulations having an acidic pH in the range of about 0.5 to not more than about 7, preferably to not more than about 6.5.

The term "aqueous" as applied to formulations or media means that water is present in an amount sufficient to at least swell or dissolve the cationic associative polymer in the composition into which it is included.

It has been surprisingly discovered that the cationic associative polymers provide desirable theological properties to low pH aqueous personal care, health care, household care, industrial and institutional care products. The cationic associative polymers are cationic compatible making them particularly useful as thickeners in products containing quaternary ammonium salts or amines. The cationic associative polymers are useful thickeners in products containing active acid components and are useful thickeners and emulsifiers for emulsions (creams, lotions). In addition to thickening, the cationic associative polymers are useful film formers, spreading aids and deposition aids for products containing colorants and emollient oils. Surprisingly, the cationic associative polymers are useful in compositions containing a relatively high concentration (e.g. 10-40%) of anionic surfactant, and also provide hair setting efficacy.

The term "personal care products" as used herein includes, without being limited thereto, cosmetics, toiletries, cosmeceuticals and beauty aids, personal hygiene and cleansing products applied to the skin, hair, scalp, and nails of humans and animals. The term "health care products" as used herein includes, without being limited thereto, pharmaceuticals, pharmacosmetics, oral care products (mouth, teeth), eye care products, ear care products and over-the-counter products and appliances, such as patches, plasters, dressings and the like, and medical devices externally applied to or into the body of humans and animals for ameliorating a health-related or medical condition, for generally maintaining hygiene or well-being, and the like. The term "body" includes the keratinous (hair, nails) and non-keratinous skin areas of the entire body (face, trunk, limbs, hands and feet), the tissues of body openings and eyes, and the term "skin" includes the scalp and mucous membranes. The term "household care products" as used herein includes, without being limited thereto, products employed in a domestic household for surface cleaning or biocidal cleaning products for maintaining sanitary conditions, such as in the kitchen and bathroom, and laundry products for fabric care and cleaning, and the like. The term "institutional and industrial care" and "I&I", as used herein includes, without being limited thereto, products employed for cleaning or maintaining sanitary conditions in industrial and institutional environments, including hospital and health care facilities, and the like.

The cationic associative polymers of the present invention are multi-purpose polymers, which are preferably prepared by polymerizing a monomer mixture containing: at least one basic, amino-substituted vinyl (ASV) monomer or salt thereof; at least one hydrophobic nonionic vinyl (HNV) monomer; at least one associative vinyl (AV) monomer; at least one semihydrophobic vinyl surfactant (SVS) monomer; and, optionally one or more hydroxy-substituted nonionic vinyl (HSNV) or crosslinking (XL) monomer. The cationic associative polymers of the present invention can also be prepared from monomer mixtures containing chain transfer agents (CTA) or other functional components commonly utilized in emulsion polymers and emulsion polymerization processes.

In one preferred embodiment, the inventive multi-purpose cationic associative polymer is the polymerization product of a monomer mixture comprising, on a total monomer mixture weight basis: (a) about 10 to about 70 weight percent of at least one ASV monomer or a salt thereof; (b) about 20 to about 80 weight percent of at least one HNV monomer; (c) about 0.01 to about 25 weight percent of at least one AV monomer; (d) about 0.01 to about 25 weight percent of at least one SVS monomer; (e) up to about 10 weight percent of a HSNV monomer; (f) up to about 5 weight percent of a XL monomer; (g) up to about 10 weight percent of a CTA; and (h) up to about 2 weight percent of a polymeric stabilizer.

In another preferred embodiment, the cationic associative polymer is the polymerization product of a monomer mixture comprising, on a total monomer mixture weight basis: (a) about 25 to about 60 weight percent of at least one ASV monomer or a salt thereof; (b) about 20 to about 70 weight percent of at least one HNV monomer; (c) about 0.1 to about 15 weight percent of at least one AV monomer; (d) about 0.1 to about 10 weight percent of at least one SVS monomer; (e) about 0.1 to about 10 weight percent of HSNV monomer; (f) about 0.001 to about 5 weight percent of a XL monomer; and (g) about 0.001 to about 5 weight percent of a CTA.

A particularly preferred polymer of the present invention is a polymer that is the product of polymerization of a monomer mixture comprising, on a total monomer mixture weight basis:

(a) about 20 to about 50 weight percent of at least one amino-substituted vinyl monomer selected from:
3-(N,N-dimethylamino)propyl (meth)acrylate, and N'-(3-N,N-dimethylamino)propyl (meth)acrylamide. Most preferred are 2-(N,N-dimethylamino)ethyl methacrylate (DMAEMA), 2-(N,N-diethylamino)ethyl methacrylate (DEAEMA), 2-(tert-butylamino)ethyl methacrylate (TBAEMA), 2-(N,N-dimethylamino)propyl methacrylamide (DMAPMAm), and 2-(N,N-dimethylamino)neopentyl acrylate (DMANPA).

(b) about 50 to about 65 weight percent of at least one hydrophobic nonionic vinyl monomer selected from $C_1$-$C_{30}$ alkyl ester of acrylic acid, a $C_1$-$C_{30}$ alkyl ester of methacrylic acid, and a mixture thereof;

(c) about 0.1 to about 10 weight percent of at least one associative vinyl monomer selected from cetyl polyethoxylated methacrylate (CEM), cetearyl polyethoxylated methacrylate (CSEM), stearyl polyethoxylated (meth)acrylate, arachidyl polyethoxylated (meth)arcylate, behenyl polyethoxylated methacrylate (BEM), lauryl polyethoxylated methacrylate (LEM), cerotyl polyethoxylated (meth)acrylate, monthanyl polyethoxylated (meth)acrylate, melissyl polyethoxylated (meth)acrylate, lacceryl polyethoxylated (meth) acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM);

(d) about 0.1 to about 10 weight percent of at least one semihydrophobic vinyl surfactant monomer having one of the following chemical formulas:

$$CH_2=CH-O(CH_2)_aO(C_3H_6O)_b(C_2H_4O)_cH \text{ or}$$

$$CH_2=CHCH_2O(C_3H_6O)_d(C_2H_4O)_eH;$$

wherein a is 2, 3, or 4; b is an integer in the range of 1 to about 10; c is an integer in the range of about 5 to about 50; d is an integer in the range of 1 to about 10; and e is an integer in the range of about 5 to about 50;

(e) up to about 10 weight percent of a hydroxy-substituted nonionic vinyl monomer;

(f) up to about 5 weight percent of a crosslinking monomer;

(g) up to about 10 weight percent of a chain transfer agent; and (h) up to about 2 weight percent of a polymeric stabilizer.

As used herein the term "alkyl" means a substituted or unsubstituted aliphatic hydrocarbon moiety including linear, branched and carbocyclic alkyl moieties. The term "carbocyclic alkyl" means an alkyl group comprising one or more carbocyclic rings of from 3 to about 12 carbon atoms in size and optionally including alkyl substituents on the carbocyclic ring. The term "aryl" includes substituted and unsubstituted phenyl and naphthyl moieties. Modifiers of the form "$C_x$-$C_y$," designate that the alkyl or carbocyclic alkyl groups have molecular formulas containing a total of x to y carbon atoms, where x and y are specified integers. As used herein and in the appended claims, the term "complex ester" means a di-, tri-, or poly-ester of a polyol such as a sugar, having at least one hydroxyl group capable of being alkylated with a $C_2$-$C_7$ alkylene oxide. The term "complex ester" includes, in particular the complex hydrophobes described in Jenkins et al., in U.S. Pat. No. 5,639,841, the relevant disclosure of which is incorporated herein by reference.

The terms "halogen-substituted", "hydroxy-substituted", "carboxy-substituted", "polyoxyalkylene-substituted", alkyl-substituted", and "aryl-substituted" as used herein in reference to alkyl or aryl groups, and the like, mean that at least one hydrogen atom on an alkyl, aryl, or like group has been replaced by at least one halogen atom, hydroxyl group, carboxyl group, polyoxyalkylene group, alkyl group, or aryl group, respectively. The terms "poly(meth)acrylate" and "poly(meth)acrylamide" as used herein refer in the alternative to polyacrylate or polymethacrylate, and to polyacrylamide or polymethacrylamide, respectively.

Suitable monomers useful in the preparation of the cationic associative polymers of the present invention are described below.

ASV Monomer

Amino-substituted vinyl monomers suitable for the preparation of the inventive cationic associative polymers are basic, polymerizable, ethylenically unsaturated monomers preferably containing at least one amino functional group. These basic amino groups can be derived from mono-, di- or poly-amino alkyl groups or nitrogen containing heteroaromatic groups. The amino group can comprise primary, secondary or tertiary amines. The monomers can be used in the amino form or in the salt form, as desired.

The polymers of the present invention preferably include an ASV monomer selected from: a mono-($C_1$-$C_4$)alkylamino($C_1$-$C_8$)alkyl (meth)acrylate, a di-($C_1$-$C_4$)alkylamino($C_1$-$C_8$)alkyl (meth)acrylate, a mono-($C_1$-$C_4$)alkylamino($C_1$-$C_8$)alkyl (meth)acrylamide, a di-($C_1$-$C_4$)alkylamino($C_1$-$C_8$)alkyl (meth)acrylamide, a nitrogen-containing heterocyclic (meth)acrylamide, a nitrogen-containing heterocyclic (meth)acrylate, and a mixture thereof.

Examples of preferred ASV monomers include, but are not limited to: a mono- or di-($C_1$-$C_4$)alkylamino($C_1$-$C_4$) alkyl (meth)acrylate, such as 2-(N,N-dimethylamino)ethyl (meth)acrylate, 3-(N,N-dimethylamino)propyl (meth)acrylate, 4-(N,N-dimethylamino)butyl (meth)acrylate, (N,N-dimethylamino)-t-butyl(meth)acrylate, 2-(N,N-diethylamino)ethyl (meth)acrylate, 3-(N,N-diethylamino)propyl (meth)acrylate, 4-(N,N-diethylamino)butyl(meth)acrylate, 2-(N,N-dipropylamino)ethyl (meth)acrylate, 3-(N,N-dipropylamino)propyl (meth)acrylate, 4-(N,N-dipropylamino)butyl (meth)acrylate, and the like; a mono- or di-($C_1$-$C_4$) alkylamino($C_1$-$C_4$)alkyl (meth)acrylamide such as N'-(2-N,N-dimethylamino)ethyl methacrylamide, N'-(3-N,N-dimethylamino)propyl acrylamide, and the like; and a nitrogen-containing heterocyclic (meth)acrylamide or (meth)acrylate such as N-(2-pyridyl)acrylamide, N-(2-imidazoyl)methacrylamide, 2-(4-morpholinyl)ethyl methacrylate, 2-(4-morpholinyl)ethyl acrylate, N-(4-morpholinyl) methacrylamide, N-(4-morpholinyl) acrylamide, 2-vinyl pyridine, 4-vinyl pyridine, and the like.

Suitable salt forms of the monomers include, but are not limited to, mineral acid salts such as the hydrochloride, sulfate, and phosphate salts; and organic acid salts such as the acetate, maleate, and fumarate salts; and the like.

The foregoing monomers or salts thereof can be used as the amino-substituted vinyl monomer component of the inventive cationic associative polymers, individually, or in mixtures of two or more. Particularly preferred ASV monomers are 2-(N,N-dimethylamino)ethyl (meth)acrylate, 3-(N,N-dimethylamino)propyl (meth)acrylate, and N'-(3-N,N-dimethylamino)propyl (meth)acrylamide. Most preferred are 2-(N,N-dimethylamino)ethyl methacrylate (DMAEMA), 2-(N,N-diethylamino)ethyl methacrylate (DEAEMA), 2-(tert-butylamino)ethyl methacrylate (TBAEMA), 2-(N,N-dimethylamino)propyl methacrylamide (DMAPMAm), and 2-(N,N-dimethylamino)neopentyl acrylate (DMANPA).

The ASV monomer preferably comprises about 10 to about 70 weight percent of the total monomer mixture, more preferably about 20 to about 50 weight percent, and most preferably about 30 to about 40 weight percent, on a total monomer mixture weight basis.

HNV Monomer

Hydrophobic nonionic vinyl monomers suitable for use in the preparation of the inventive cationic associative polymers are copolymerizable, nonionic, ethylenically unsaturated monomers having either of the following formulas (I) or (II):

$$CH_2=C(X)Z, \quad\quad\quad (I)$$

$$CH_2=CH-OC(O)R; \quad\quad\quad (II)$$

wherein, in each of formulas (I) and (II), X is H or methyl; and Z is $-C(O)OR^1$, $-C(O)NH_2$, $-C(O)NHR^1$, $-C(O)N(R^1)_2$, $-C_6H_4R^1$, $-C_6H_4OR^1$, $-C_6H_4Cl$, $-CN$, $-NHC(O)CH_3$, $-NHC(O)H$, N-(2-pyrrolidonyl), N-caprolactamyl, $-C(O)NHC(CH_3)_3$, $-C(O)NHCH_2CH_2-N$-ethyleneurea, $-SiR_3$, $-C(O)O(CH_2)_nSiR_3$, $-C(O)NH(CH_2)_xSiR_3$, or $-(CH_2)_xSiR_3$; x is an integer in the range of 1 to about 6; each R is independently $C_1$-$C_{30}$ alkyl; each $R^1$ is independently $C_1$-$C_{30}$ alkyl, hydroxy-substituted $C_2$-$C_{30}$ alkyl or halogen-substituted $C_1$-$C_{30}$ alkyl.

Non-limiting examples of preferred hydrophobic nonionic vinyl monomers include $C_1$-$C_{30}$ alkyl (meth)acrylates; $C_1$-$C_{30}$ alkyl (meth)acrylamides; styrene; substituted styrenes such as vinyl toluene, (e.g., 2-methyl styrene), butyl styrene, isopropyl styrene, p-chloro styrene, and the like; vinyl esters such as vinyl acetate, vinyl butyrate, vinyl caprolate, vinyl pivalate, vinyl neodecanoate, and the like; unsaturated nitrites such as methacrylonitrile, acrylonitrile and the like; and unsaturated silanes such as trimethylvinylsilane, dimethylethylvinylsilane, allyldimethylphenylsilane, allytrimethylsilane, 3-acrylamidopropyltrimethylsilane, 3-trimethylsilylpropyl methacrylate, and the like.

Particularly preferred nonionic vinyl monomers include $C_1$-$C_{30}$ alkyl esters of acrylic acid and of methacrylic acid and mixtures thereof, such as ethyl acrylate (EA), methyl methacrylate (MMA), 3,3,5-trimethylcyclohexyl methacrylate (TMCHMA), and mixtures thereof.

The HNV monomer preferably comprises about 20 to about 80 weight percent of the total monomer mixture, more preferably about 30 to about 70 weight percent, and most preferably about 50 to about 65 weight percent, on a total monomer mixture weight basis.

AV Monomer

Associative vinyl monomers suitable for use in the production of the inventive cationic associative polymers are compounds preferably having an ethylenically unsaturated end group portion (i) for addition polymerization with the other monomers of the system; a polyoxyalkylene midsection portion (ii) for imparting selective hydrophilic properties to the product polymer and a hydrophobic end group portion (iii) for providing selective hydrophobic properties to the polymer.

The portion (i) supplying the ethylenically unsaturated end group preferably is derived from an α,β-ethylenically unsaturated mono or di-carboxylic acid or the anhydride thereof, more preferably a $C_3$ or $C_4$ mono- or di-carboxylic acid or the anhydride thereof. Alternatively, portion (i) of the associative monomer can be derived from an allyl ether or vinyl ether; a nonionic vinyl-substituted urethane monomer, such as disclosed in U.S. Reissue Pat. No. 33,156 or U.S. Pat. No. 5,294,692; or a vinyl-substituted urea reaction product, such as disclosed in U.S. Pat. No. 5,011,978; the relevant disclosures of each are incorporated herein by reference.

The midsection portion (ii) is preferably a polyoxyalkylene segment of about 5 to about 250, more preferably about 10 to about 120, and most preferably about 15 to about 60 repeating $C_2$-$C_7$ alkylene oxide units. Preferred midsection portions (ii) include polyoxyethylene, polyoxypropylene, and polyoxybutylene segments comprising about 5 to about 150, more preferably about 10 to about 100, and most preferably about 15 to about 60 ethylene, propylene or butylene oxide units, and random or non-random sequences of ethylene oxide, propylene oxide and or butylene oxide units.

The hydrophobic end group portion (iii) of the associative monomers is preferably a hydrocarbon moiety belonging to one of the following hydrocarbon classes: a $C_8$-$C_{40}$ linear alkyl, an aryl-substituted $C_2$-$C_{40}$ alkyl, a $C_2$-$C_{40}$ alkyl-substituted phenyl, a $C_8$-$C_{40}$ branched alkyl, a $C_8$-$C_{40}$ carbocyclic alkyl; and a $C_8$-$C_{80}$ complex ester.

Non-limiting examples of suitable hydrophobic end group portions (iii) of the associative monomers are linear or branched alkyl groups having about 8 to about 40 carbon atoms such as capryl ($C_8$), isooctyl (branched $C_8$), decyl ($C_{10}$), lauryl ($C_{12}$), myristyl ($C_{14}$), cetyl ($C_{16}$), cetearyl ($C_{16}$-$C_{18}$), stearyl ($C_{18}$), isostearyl (branched $C_{18}$), arachidyl ($C_{20}$), behenyl ($C_{22}$), lignoceryl ($C_{24}$), cerotyl ($C_{26}$), montanyl ($C_{28}$), melissyl ($C_{30}$), lacceryl ($C_{32}$), and the like.

Examples of linear and branched alkyl groups having about 8 to about 40 carbon atoms that are derived from a natural source include, without being limited thereto, alkyl groups derived from hydrogenated peanut oil, soybean oil and canola oil (all predominately $C_{18}$), hydrogenated tallow oil ($C_{16}$-$C_{18}$), and the like; and hydrogenated $C_{10}$-$C_{30}$ terpenols, such as hydrogenated geraniol (branched $C_{10}$), hydrogenated farnesol (branched $C_{15}$), hydrogenated phytol (branched $C_{20}$), and the like.

Non-limiting examples of suitable $C_2$-$C_{40}$ alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Suitable $C_8$-$C_{40}$ carbocyclic alkyl groups include, without being limited thereto, groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without being limited thereto, cyclooctyl, cyclododecyl, adamantyl, decahydronaphthyl, and groups derived from natural carbocyclic materials such as pinene, hydrogenated retinol, camphor, isobornyl alcohol, and the like.

Exemplary aryl-substituted $C_2$-$C_{40}$ alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Non-limiting examples of suitable $C_8$-$C_{80}$ complex esters include hydrogenated castor oil (predominately the triglyceride of 12-hydroxystearic acid); 1,2-diacyl glycerols such as 1,2-distearyl glycerol, 1,2-dipalmityl glycerol, 1,2-dimyristyl glycerol, and the like; di-, tri-, or poly-esters of sugars such as 3,4,6-tristearyl glucose, 2,3-dilauryl fructose, and the like; and sorbitan esters such as those disclosed in U.S. Pat. No. 4,600,761 to Ruffner et al., the pertinent disclosures of which are incorporated herein by reference.

Useful associative monomers can be prepared by any method known in the art. See, for example, U.S. Pat. No. 4,421,902 to Chang et al.; U.S. Pat. No. 4,384,096 to Sonnabend; U.S. Pat. No. 4,514,552 to Shay et al.; U.S. Pat. No. 4,600,761 to Ruffner et al.; U.S. Pat. No. 4,616,074 to Ruffner; U.S. Pat. No. 5,294,692 to Barron et al.; U.S. Pat. No. 5,292,843 to Jenkins et al.; U.S. Pat. No. 5,770,760 to Robinson; and U.S. Pat. No. 5,412,142 to Wilkerson, III et al.; the pertinent disclosures of which are incorporated herein by reference.

Examples of preferred associative vinyl monomers include those having the following formula (III):

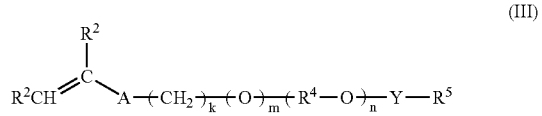

(III)

wherein, each $R^2$ is independently H, methyl, —C(O)OH, or —C(O)OR$^3$; $R^3$ is $C_1$-$C_{30}$ alkyl; A is —CH$_2$C(O)O—, —C(O)O—, —O—, —CH$_2$O—, —NHC(O)NH—, —C(O)NH—, —Ar—(CE$_2$)$_z$—NHC(O)O—, —Ar—(CE$_2$)$_z$—NHC(O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; (R$^4$—O)$_n$ is a polyoxyalkylene, which is a homopolymer, a random copolymer, or a block copolymer of $C_2$-$C_4$ oxyalkylene units, wherein R$^4$ is $C_2H_4$, $C_3H_6$, $C_4H_8$, or a mixture thereof, and n is an integer in the range of about 5 to about 250, preferably about 5 to about 100, more preferably about 10 to about 80, and most preferably about 15 to about 60; Y is —R$^4$O—, —R$^4$NH—, —C(O)—, —C(O)NH—, —R$^4$NHC(O)NH—, or —C(O)NHC(O)—; and R$^5$ is a substituted or unsubstituted alkyl selected from the group consisting of a $C_8$-$C_{40}$ linear alkyl, a $C_8$-$C_{40}$ branched alkyl, a $C_8$-$C_{40}$ carbocyclic alkyl, a $C_2$-$C_{40}$ alkyl-substituted phenyl, an aryl-substituted $C_2$-$C_{40}$ alkyl, and a $C_8$-$C_{80}$ complex ester; wherein the R$^5$ alkyl group optionally comprises one or more substituents selected from the group consisting of a hydroxyl group, an alkoxyl group, and a halogen group.

Particularly preferred associative vinyl monomers of formula (III) include cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), where the polyethoxylated portion of the monomer comprises about 5 to about 100, preferably about 10 to about 80, and more preferably about 15 to about 60 ethylene oxide repeating units.

Preferably, the AV monomer component in the monomer mixture comprises, on a total monomer mixture weight basis, about 0.001 to about 25 weight percent of the monomer mixture, more preferably about 0.01 to about 15 weight percent, most preferably about 0.1 to about 10 weight percent.

SVS Monomer

It was surprisingly found that a semihydrophobic vinyl surfactant (SVS) monomer, which contains a polyoxyalkylene chain, can moderate the associative properties of cationic associative polymers containing them, thus producing aqueous gels with highly desirable texture and rheological properties. Not wishing to be bound by theory, it is thought that the polyoxyalkylene group of the SVS monomer interrupts or shields against non-specific associations between the hydrophobic groups of the associative monomers in the polymer and thus attenuates the associative properties of the polymers. Such SVS monomers can tailor the thickening efficiency of the resulting polymers to customize the theological properties of the polymer as desired for a selected application. Most surprisingly, the SVS monomers were found to impart desirable rheological and aesthetic properties to aqueous gels, providing softer, smoother and more spreadable gels than cationic associative polymers containing no SVS monomer.

Surprisingly, incorporation of a SVS monomer into a cationic associative polymer can minimize or diminish viscosity reduction under low shear stress and can provide a shear thinning profile that is smooth flowing.

As used herein the terms "semihydrophobic vinyl surfactant monomer" and "SVS monomer" refer to compounds having two portions: (i) an ethylenically unsaturated end group portion for addition polymerization with the other monomers of the reaction mixture, and (ii) a polyoxyalkylene portion for attenuating the associations between the hydrophobic groups of the polymer or hydrophobic groups from other materials in a composition containing the polymer. A SVS monomer is similar in structure to an associative monomer, but has a substantially non-hydrophobic end group portion and thus, does not impart any associative properties to the polymer.

The unsaturated end group portion (i) supplying the vinyl or other ethylenically unsaturated end group for addition polymerization is preferably derived from an α,β-ethylenically unsaturated mono or di-carboxylic acid or the anhydride thereof, preferably a $C_3$ or $C_4$ mono- or di-carboxylic acid, or the anhydride thereof. Alternatively, the end group portion (i) can be derived from an allyl ether, vinyl ether or a nonionic unsaturated urethane.

The polymerizable unsaturated end group portion (i) can also be derived from a $C_8$-$C_{30}$ unsaturated fatty acid group containing at least one free carboxy-functional group. This $C_8$-$C_{30}$ group is part of the unsaturated end group portion (i) and is different from the hydrophobic groups pendant to the associative monomers, which are specifically separated from the unsaturated end group of the associative monomer by a hydrophilic "spacer" portion.

The polyoxyalkylene portion (ii) specifically comprises a long-chain polyoxyalkylene segment, which is substantially similar to the hydrophilic portion of the associative monomers. Preferred polyoxyalkylene portion (ii) includes polyoxyethylene, polyoxypropylene, and polyoxybutylene units comprising about 5 to about 250, and preferably about 10 to about 100 oxyalkylene units. When the SVS monomer comprises more than one type of oxyalkylene unit, the units can be arranged in random, non-random, or block sequences.

Preferred SVS monomers include those having either of the following formulas (IV) or (V):

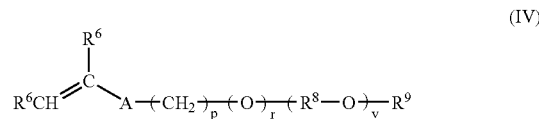

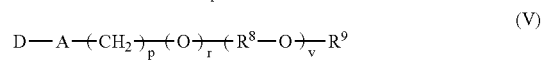

wherein, in each of formulas (IV) and (V), each $R^6$ is independently H, $C_1$-$C_{30}$ alkyl, —C(O)OH, or —C(O)OR$^7$; $R^7$ is $C_1$-$C_{30}$ alkyl; A is —CH$_2$C(O)O—, —C(O)O—, —O—, —CH$_2$O—, —NHC(O)NH—, —C(O)NH—, —Ar—(CE$_2$)$_z$—NHC(O)O—, —Ar—(CE$_2$)$_z$—NHC(O)NH—, or —CH$_2$CH$_2$NHC(O)—; Ar is a divalent aryl; E is H or methyl; z is 0 or 1; p is an integer in the range of 0 to about 30, and r is 0 or 1, with the proviso that when p is 0, r is 0, and when p is in the range of 1 to about 30, r is 1; $(R^8$—O$)_v$ is a polyoxyalkylene, which is a homopolymer, a random copolymer or a block copolymer of $C_2$-$C_4$ oxyalkylene units, wherein $R^8$ is $C_2H_4$, $C_3H_6$, $C_4H_8$, or a mixture thereof, and v is an integer in the range of about 5 to about 250, preferably about 5 to about 100, more preferably about 10 to about 80, and most preferably about 15 to about 60; $R^9$ is H or $C_1$-$C_4$ alkyl; and D is a $C_8$-$C_{30}$ unsaturated alkyl, or a carboxy-substituted $C_8$-$C_{30}$ unsaturated alkyl.

Particularly preferred SVS monomers include monomers having the following chemical formulas:

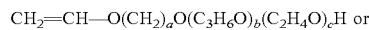

wherein a, preferably, is 2, 3, or 4; b, preferably, is an integer in the range of 1 to about 10, more preferably about 2 to about 8, most preferably about 3 to about 7; c, preferably, is an integer in the range of about 5 to about 50, more preferably about 8 to about 40, most preferably about 10 to about 30; d, preferably, is an integer in the range of 1 to about 10, more preferably about 2 to about 8, most preferably about 3 to about 7; and e, preferably, is an integer in the range of about 5 to about 50, more preferably about 8 to about 40.

Examples of preferred SVS monomers include polymerizable emulsifiers commercially available under the trade names EMULSOGEN® R109, R208, R307, RAL109, RAL208, and RAL307 sold by Clariant Corporation; BX-AA-E5P5 sold by Bimax, Inc.; and MAXEMUL® 5010 and 5011 sold by Uniqema; and combinations thereof.

Particularly preferred SVS monomers include EMULSOGEN® R208, R307, and RAL307.

According to the manufacturers: EMULSOGEN® R109 is a randomly ethoxylated/propoxylated 1,4-butanediol vinyl ether having the empirical formula $CH_2=CH-O(CH_2)_4O(C_3H_6O)_4(C_2H_4O)_{10}H$;

EMULSOGEN® R208 is a randomly ethoxylated/propoxylated 1,4-butanediol vinyl ether having the empirical formula:

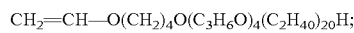

$CH_2=CH-O(CH_2)_4O(C_3H_6O)_4(C_2H_{40})_{20}H$;

EMULSOGEN® R307 is a randomly ethoxylated/propoxylated 1,4-butanediol vinyl ether having the empirical formula:

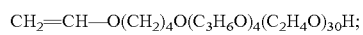

$CH_2=CH-O(CH_2)_4O(C_3H_6O)_4(C_2H_4O)_{30}H$;

EMULSOGEN® RAL109 is a randomly ethoxylated/propoxylated allyl ether having the empirical formula $CH_2=CHCH_2O(C_3H_6O)_4(C_2H_{40})_{10}H$;

EMULSOGEN® RAL208 is a randomly ethoxylated/propoxylated allyl ether having the empirical formula $CH_2=CHCH_2O(C_3H_{60})_4(C_2H_4O)_{20}H$;

EMULSOGEN® RAL307 is a randomly ethoxylated/propoxylated allyl ether having the empirical formula $CH_2=CHCH_2O(C_3H_6O)_4(C_2H_{40})_{30}H$;

MAXEMUL® 5010 is a carboxy-functional $C_{12}$-$C_{15}$ alkenyl hydrophobe, ethoxylated with about 24 ethylene oxide units;

MAXEMUL® 5011 is a carboxy-functional $C_{12}$-$C_{15}$ alkenyl hydrophobe, ethoxylated with about 34 ethylene oxide units; and BX-AA-E5P5 is a randomly ethoxylated/propoxylated allyl ether having the empirical formula $CH_2=CHCH_2O(C_3H_{60})_5(C_2H_{40})_5H$.

The amount of SVS monomers utilized in the preparation of the cationic associative polymers of the present invention can vary widely and depends, among other things, on the final rheological properties desired in the polymer. When utilized, the monomer reaction mixture preferably contains at least about 0.01 weight percent of one or more SVS monomers based on the total monomer mixture weight, more preferably at least about 0.1 weight percent. The monomer mixture preferably comprises not more than about 25 weight percent of SVS monomer, more preferably not more than about 10 weight percent, based on the total monomer mixture weight.

HSNV Monomer

The inventive cationic associative polymers can optionally be prepared from monomer mixtures containing hydroxy-substituted nonionic vinyl monomers. HSNV monomers are ethylenically unsaturated monomers comprising one or more hydroxyl substituents.

Examples of suitable HSNV monomers include, but are not limited to, a hydroxy-substituted ($C_1$-$C_4$)alkyl (meth) acrylate such as 2-hydroxyethyl methacrylate (HEMA), 2-hydroxyethyl acrylate (2-HEA), 3-hydroxypropyl acrylate, and the like; a hydroxy-substituted ($C_1$-$C_4$)alkyl (meth) acrylamide such as N-(2-hydroxyethyl) methacrylamide, N-(2-hydroxyethyl) acrylamide, N-(3-hydroxypropyl) acrylamide, N-(2,3-dihydroxypropyl) acrylamide, and the like. Other useful HSNV monomers include allyl alcohol, glycerol monoallyl ether, 3-methyl-3-buten-1-ol, and vinyl alcohol precursors and equivalents, such as vinyl acetate.

When utilized, the monomer reaction mixture preferably contains one or more HSNV monomers in amounts up to about 10 weight percent based on the total monomer mixture weight. In a preferred embodiment, the amount of HSNV monomer in the mixture is in the range of about 0.01 to about 10 weight percent based on the total monomer mixture weight, more preferably about 1 to about 8 weight percent, most preferably about 1 to about 5 weight percent.

XL Monomer

The inventive cationic associative polymers can be prepared from a monomer mixture comprising one or more crosslinking monomers for introducing branching and controlling molecular weight. Suitable polyunsaturated crosslinkers are well known in the art. Mono-unsaturated compounds carrying a reactive group that is capable of causing a formed copolymer to be crosslinked before, during, or after polymerization has taken place can also be utilized. Other useful crosslinking monomers include polyfunctional monomers containing multiple reactive groups such as epoxide groups, isocyanate groups, and hydrolyzable silane groups. Various polyunsaturated compounds can be utilized to generate either a partially or substantially cross-linked three dimensional network.

Examples of suitable polyunsaturated crosslinking monomer components include, without being limited thereto, polyunsaturated aromatic monomers such as divinylbenzene, divinyl naphthylene, and trivinylbenzene; polyunsaturated alicyclic monomers, such as 1,2,4-trivinylcyclohexane; di-functional esters of phthalic acid such as diallyl phthalate; polyunsaturated aliphatic monomers, such as dienes, trienes, and tetraenes, including isoprene, butadiene, 1,5-hexadiene, 1,5,9-decatriene, 1,9-decadiene, 1,5-heptadiene; and the like.

Other suitable polyunsaturated crosslinking monomers include polyalkenyl ethers such as triallyl pentaerythritol, diallyl pentaerythritol, diallyl sucrose, octaallyl sucrose, and trimethylolpropane diallyl ether; polyunsaturated esters of polyalcohols or polyacids such as 1,6-hexanediol di(meth) acrylate, tetramethylene tri(meth)acrylate, allyl acrylate, diallyl itaconate, diallyl fumarate, diallyl maleate, trimethylolpropane tri(meth)acrylate, trimethylolpropane di(meth) acrylate, and polyethylene glycol di(meth)acrylate; alkylene bisacrylamides, such as methylene bisacrylamide, propylene bisacrylamide, and the like; hydroxy and carboxy derivatives of methylene bisacrylamide, such as N,N'-bismethylol methylene bisacrylamide; polyethyleneglycol di(meth)acrylates, such as ethyleneglycol di(meth)acrylate, diethyleneglycol di(meth)acrylate, and triethyleneglycol di(meth)acrylate; polyunsaturated silanes, such as dimethyldivinylsilane, methyltrivinylsilane, allyldimethylvinylsilane, diallyldimethylsilane, and tetravinylsilane; polyunsaturated stannanes, such as tetraallyl tin, and diallyldimethyl tin; and the like.

Useful monounsaturated compounds carrying a reactive group include N-methylolacrylamide; N-alkoxy(meth)acrylamide, wherein the alkoxy group is a $C_1$-$C_{18}$ alkoxy; and unsaturated hydrolyzable silanes such as triethoxyvinylsilane, tris-isopropoxyvinylsilane, and 3-triethoxysilylpropyl methacrylate; and the like.

Useful polyfunctional crosslinking monomers containing multiple reactive groups include, but are not limited to, hydrolyzable silanes such as ethyltriethoxysilane and ethyltrimethoxysilane; epoxy-substituted hydrolyzable silanes, such as 2-(3,4-epoxycyclohexyl)ethyltriethoxysilane and 3-glycidoxypropyltrimethyoxysilane; polyisocyanates, such as 1,4-diisocyanatobutane, 1,6-diisocyanatohexane, 1,4-phenylenediisocyanate, and 4,4'-oxybis(phenylisocyanate); unsaturated epoxides, such as glycidyl methacrylate and allylglycidyl ether; polyepoxides, such as diglycidyl ether, 1,2,5,6-diepoxyhexane, and ethyleneglycoldiglycidyl ether; and the like.

Particularly useful are polyunsaturated crosslinkers derived from ethoxylated polyols, such as diols, triols and bis-phenols, ethoxylated with about 2 to about 100 moles of ethylene oxide per mole of hydroxyl functional group and end-capped with a polymerizable unsaturated group such as a vinyl ether, allyl ether, acrylate ester, methacrylate ester, and the like. Examples of such crosslinkers include bisphenol A ethoxylated dimethacrylate; bisphenol F ethoxylated dimethacrylate, ethoxylated trimethylol propane trimethacrylate, and the like. Other ethoxylated crosslinkers useful in the cationic associative polymers of the present invention include ethoxylated polyol-derived crosslinkers disclosed in U.S. Pat. No. 6,140,435 to Zanotti-Russo, the pertinent disclosures of which are incorporated herein by reference.

Examples of particularly preferred XL monomers are acrylate and methacrylate esters of polyols having at least two acrylate or methacrylate ester groups, such as trimethylolpropane triacrylate (TMPTA), trimethylolpropane dimethacrylate, triethylene glycol dimethacrylate (TEGDMA), ethoxylated (30) bisphenol A dimethacrylate (EOBDMA), and the like.

When utilized, crosslinking monomers are present in the monomer reaction mixture preferably in an amount of up to about 5 weight percent, based on total monomer mixture weight. In a preferred embodiment, the XL monomers are present in an amount in the range of about 0.01 to about 3 weight percent, based on the total monomer mixture weight, more preferably about 0.05 to about 2 weight percent, most preferably about 0.1 to about 1 weight percent of the monomer mixture.

Chain Transfer Agent

The inventive cationic associative polymers can optionally be prepared from a monomer mixture comprising one or more chain transfer agents, which are well known in the polymer arts.

Suitable chain transfer agents for use in this invention, without being limited thereto, are selected from a variety of thio and disulfide containing compounds, such as $C_1$-$C_{18}$ alkyl mercaptans, mercaptocarboxylic acids, mercaptocarboxylic esters, thioesters, $C_1$-$C_{18}$ alkyl disulfides, aryldisulfides, polyfunctional thiols, and the like; phosphites and hypophosphites; haloalkyl compounds, such as carbon tetrachloride, bromotrichloromethane, and the like; and unsaturated chain transfer agents, such as alpha-methylstyrene.

Polyfunctional thiols include trifunctional thiols, such as trimethylolpropane-tris-(3-mercaptopropionate), tetrafunctional thiols, such as pentaerythritol-tetra-(3-mercaptopropionate), pentaerythritol-tetra-(thioglycolate), and pentaerythritol-tetra-(thiolactate); hexafunctional thiols, such as dipentaerythritol-hexa-(thioglycolate); and the like.

Alternatively, the chain transfer agent can be any catalytic chain transfer agent which reduces molecular weight of addition polymers during free radical polymerization of vinyl monomers. Examples of catalytic chain transfer agents include, for example, cobalt complexes (e.g., cobalt (II) chelates). Catalytic chain transfer agents can often be utilized in relatively low concentrations relative to thiol-based CTAs.

Examples of preferred chain transfer agents include octyl mercaptan, n-dodecyl mercaptan, t-dodecyl mercaptan, hexadecyl mercaptan, octadecyl mercaptan (ODM), isooctyl 3-mercaptopropionate (IMP), butyl 3-mercaptopropionate, 3-mercaptopropionic acid, butyl thioglycolate, isooctyl thioglycolate, dodecyl thioglycolate, and the like. The chain transfer agents can be added to a monomer reaction mixture preferably in amounts of up to about 10 weight percent of polymerizable monomer mixture, based on total monomer mixture weight. When present, the chain transfer agent preferably comprises at least about 0.1 percent by weight based on the total monomer weight.

The inventive cationic associative polymers can be manufactured by conventional polymerization techniques, such as emulsion polymerization, as is known in the polymer art. The polymerization can be performed as a simple batch process, as a metered addition process, or the reaction can be initiated as a small batch and then the bulk of the monomers can be continuously metered into the reactor (seed process). Typically the polymerization process is carried out at a reaction temperature in the range of about 20 to about 80° C., however, higher or lower temperatures can be used. To facilitate emulsification of the monomer mixture, the emulsion polymerization is carried out in the presence of at least one surfactant. Preferably the emulsion polymerization is carried out in the presence of surfactant in the amount of about 1 to about 10 percent by weight, more preferably in the range of about 3 to about 8, most preferably in the range of about 5 to about 7 percent by weight, on a total emulsion weight basis. The emulsion polymerization reaction mixture also includes one or more free radical initiators, preferably in an amount in the range of about 0.01 to about 3 weight percent based on total monomer weight. The polymerization can be performed in an aqueous or aqueous alcohol medium at neutral to moderately alkaline pH.

In a typical polymerization, a mixture of monomers is added with mixing agitation to a solution of emulsifying surfactant, such as a nonionic surfactant, preferably a linear or branched alcohol ethoxylate, or mixtures of nonionic surfactants and anionic surfactants, such as fatty alcohol sulfates or alkyl sulfonates, in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable addition polymerization catalyst, as is well known in the emulsion polymerization art. The reaction is agitated until the polymerization is complete, typically for a time in the range of about 4 to about 16 hours. The monomer emulsion can be heated to a temperature in the range of about 20 to about 80° C. prior to addition of the initiator, if desired. Unreacted monomer can be eliminated by addition of more catalyst, as is well known in the emulsion polymerization art. The resulting polymer emulsion product can then be discharged from the reactor and packaged for storage or use. Optionally, the pH or other physical and chemical characteristics of the emulsion can be adjusted prior to discharge from the reactor. Typically, the product emulsion has a total solids content in the range of about 10 to about 40 weight percent. Typically, the total polymer content of the product emulsion is in the range of about 15 to about 35 weight percent, generally not more than about 25 weight percent.

Suitable surfactants for facilitating emulsion polymerizations include nonionic, anionic, amphoteric, cationic surfactants, and mixtures thereof. Most commonly, nonionic and anionic surfactants are utilized or mixtures thereof. The physical properties of the neutralized polymer (e.g., viscosity, spreadability, clarity, texture, and the like) can be varied by appropriate selection of the hydrophobic and hydrophilic properties of the emulsifying surfactant, as is well known in the art.

Nonionic surfactants suitable for facilitating emulsion polymerizations are well known in the polymer art, and include, without limitation, linear or branched alcohol ethoxylates, $C_8$-$C_{12}$ alkylphenol alkoxylates, such as octylphenol ethoxylates, polyoxyethylene polyoxypropylene block copolymers, and the like. Other useful nonionic surfactants include $C_8$-$C_{22}$ fatty acid esters of polyoxyethylene glycol, mono and diglycerides, sorbitan esters and ethoxylated sorbitan esters, $C_8$-$C_{22}$ fatty acid glycol esters, block copolymers of ethylene oxide and propylene oxide having an HLB value of greater than about 15, ethoxylated octylphenols, and combinations thereof.

Preferred alkylphenol alkoxylate surfactants include an octylphenol sold under the trade name IGEPAL® CA-897 by Rhodia, Inc. Preferred linear alcohol alkoxylates include polyethylene glycol ethers of cetearyl alcohol (a mixture of cetyl and stearyl alcohols) sold under the trade names PLURAFAC® C-17, PLURAFAC® A-38 and PLURAFAC® A-39 by BASF Corp. Preferred polyoxyethylene polyoxypropylene block copolymers include copolymers sold under the trade names PLURONIC® F127, and PLURONIC® L35 by BASF Corp.

Other preferred nonionic surfactants include Ethoxylated (50) linear fatty alcohols such as DISPONIL® A 5060 (Cognis), branched alkyl ethoxylates such as GENAPOL® X 1005 (Clariant Corp.), secondary $C_{12}$-$C_{14}$ alcohol ethoxylates such as TERGITOL® S15-30 and S15-40 (Dow Chemical Co.), ethoxylated octylphenol-based surfactants such as TRITON® X-305, X-405 and X-705 (Dow Chemical Co.), IGEPAL® CA 407, 887, and 897 (Rhodia, Inc.), ICONOL® OP 3070 and 4070 (BASF Corp.), SYNPERONIC® OP 30 and 40 (Uniqema), block copolymers of ethylene oxide and propylene oxide such as PLURONIC® L35 and F127 (BASF Corp.), and secondary $C_{11}$ alcohol ethoxylates such as EMULSOGEN® EPN 407 (Clariant Corp.). Numerous other suppliers are found in the trade literature.

Anionic surfactants suitable for facilitating emulsion polymerizations are well known in the polymer art, and include sodium lauryl sulfate, sodium dodecyl benzene sulfonate, sodium dioctyl sulfosuccinate, sodium di-sec-butyl naphthylene sulfonate, disodium dodecyl diphenyl ether sulfonate, and disodium n-octadecyl sulfosuccinate, and the like.

Suitable polymeric stabilizers (also known as protective colloids) for the emulsion polymerization process of this invention are water-soluble polymers, including, for example, synthetic polymers, such as polyvinyl alcohol, partially hydrolyzed polyvinyl acetate, polyvinylpyrrolidone, polyacrylamide, polymethacrylamide, carboxylate-functional addition polymers, polyalkyl vinyl ethers and the like; water-soluble natural polymers, such as gelatin, pectins, alginates, casein, starch, and the like; and modified natural polymers, such as methylcellulose, hydroxypropylcellulose, carboxymethylcellulose, allyl modified hydroxyethylcellulose, and the like. In some cases, it can be of advantage to use mixtures of a synthetic and a natural protective colloid, for example, a mixture of polyvinyl alcohol and casein. Further suitable natural polymers are mixed ethers such as methylhydroxyethylcellulose and carboxymethylmethylcellulose. Polymeric stabilizers can be utilized in amounts up to about 2 weight percent based on the total emulsion weight. When utilized, a polymeric stabilizer preferably is included in an amount in the range of about 0.0001 to about 1 weight percent, more preferably about 0.01 to about 0.5 weight percent.

The polymeric stabilizers which are used according to this invention are termed water-soluble when they are miscible in water in any proportion or have a solubility in 20° C. water of at least about 0.1% by weight and do not precipitate from these aqueous solutions on dilution with water at the foregoing temperature. The molecular weight of the water-soluble synthetic polymeric stabilizers is typically in the range of about 5,000 to about 2,000,000, preferably about 25,000 to about 1,500,000 Daltons. The viscosity of aqueous solutions of the polymeric stabilizers is typically in the range of about 1 to about 10,000 mPa·s at a concentration of about 2 to about 10% by weight and a temperature of about 20° C.

A particularly preferred polymeric stabilizer is an allyl modified hydroxyethylcellulose, such as TYLOSE® AM-HEC grades available from Clariant. The reactive allyl groups in the side chain increase the grafting power of the cellulose ether resulting in a stable emulsion. A preferred TYLOSE® stabilizer is allyl modified hydroxyethylcellulose powder (particle size <180 μm) TYLOSE® AM H40 YP2 (AMHEC).

Exemplary preferred free radical initiators include, without being limited thereto, the water-soluble inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid; and oil soluble, free radical producing agents, such as 2,2'-azobisisobutyronitrile, and the like, and mixtures thereof. Peroxides and peracids can optionally be activated with reducing agents, such as sodium bisulfite or ascorbic acid, transition metals, hydrazine, and the like. Particularly suitable free-radical polymerization initiators include water soluble azo polymerization initiators, such as 2,2'-azobis(tert-alkyl) compounds having a water solubilizing substituent on the alkyl group. Preferred azo polymerization catalysts include the VAZO® free-radical polymerization initiators, available from DuPont, such as VAZO® 44 (2,2'-azobis(2-(4,5-dihydroimidazolyl)propane), VAZO® 56 (2,2'-azobis(2-methylpropionamidine) dihydrochloride), and VAZO® 68 (4,4'-azobis(4-cyanovaleric acid)).

Optionally, other emulsion polymerization additives, which are well known in the emulsion polymerization art, such as solvents, buffering agents, chelating agents, inorganic electrolytes, chain terminators, and pH adjusting agents can be included in the polymerization system.

A preferred general emulsion polymerization procedure for the preparation of cationic associative polymers of the present invention and of cationic emulsion polymers, in general, is provided below:

A monomer emulsion is preferably prepared in a reactor equipped with a nitrogen inlet and an agitator by combining a desired amount of each monomer in a quantity of water containing an emulsifying amount of a nonionic surfactant, or a mixture of a nonionic surfactant and an anionic surfactant, under a nitrogen atmosphere, and with mixing agitation. The degree of agitation required to form an emulsion from a monomer mixture of the type described above is well known to those of skill in the art. The so-formed emulsion is substantially deoxygenated by any suitable method known in the art, such as by sparging with nitrogen, and then a free radical initiator is added to the emulsion, with continuous mixing agitation, to initiate polymerization. The temperature of the emulsion can be adjusted, before or after addition of the initiator, to a temperature in the range of about 20 to about 60° C. if desired. After the addition of initiator, the temperature of the polymerization reaction mixture is typically adjusted to a temperature in the range of about 60 to 80° C. and held at such temperature for a time sufficient to complete the polymerization, typically in the range of about 3 to about 14 hours. Optionally, unreacted residual monomers can be destroyed or further polymerized by the addition of various redox reagents or catalysts. The resulting polymer emulsion can then be cooled and discharged from the reactor and collected.

One skilled in the polymer art will recognize that the amounts of each monomer component can be adjusted to obtain polymers having any desired ratio of monomer components. Varying proportions of water can also be utilized, as desired. Water miscible solvents, such as alcohols, and other polymerization additives, as described above, may also be included in the reaction mixture. Preferred alcohols include glycols such as ethylene glycol, propylene glycol, butylene glycol, hexylene glycol, glycerol, and the like.

The product polymer emulsions can be prepared to preferably contain about 1 percent to about 60 percent total polymer solids, more preferably about 10 percent to about 40 percent total polymer solids, most preferably about 15 percent to about 25 percent total polymer solids based on the weight of the polymer.

Prior to any neutralization, the polymer emulsions, as produced, typically have a pH in the range of about 7.5 or greater, a Brookfield viscosity of not more than about 100 mPa·s at ambient room temperature (spindle #2, 20 rpm), and a particle size of not more than about 300 nm as determined by Method D below.

Optionally, the produced cationic associative polymer emulsions can be further processed by adjusting the pH to a value preferably in the range of about 1 to not more than about 7, if an acidic pH is desired, with acidic materials, preferably organic acids, mineral acids, and the like. The cationic associative polymer emulsions typically swell to form smooth, viscous solutions that are flowable and sprayable, or gels at neutral to acidic pH, and the polymers are generally substantially stable at such pH values. The cationic associative polymer emulsions can be diluted with water or solvent, or concentrated by evaporating a portion of the water. Alternatively, the obtained cationic associative polymer emulsion can be substantially dried to a powder or crystalline form by utilizing equipment well known in the art, such as, for example, a spray drier, a drum drier, a freeze drier, and the like.

The inventive cationic associative polymers can be prepared by emulsion polymerization and utilized by incorporating various known additives and conventional adjuvants, and solvents other than water, into the liquid cationic associative polymer emulsion product, as needed, to achieve the intended form for use of the final composition without altering or adversely affecting the performance or properties of the cationic associative polymer. Alternatively, the cationic associative polymer can be incorporated as an ingredient into a formulation, preferably in a liquid form, employing conventional mixing equipment.

A preferred cationic associative polymer of this invention, at a weight concentration of about 2% in deionized water, in its neutralized or acidic form at a pH in the range of about 1 to about 7, can provide a Brookfield viscosity ranging from about 300 mPa·s to about 100,000 mPa·s or more (Brookfield RVT, 20 rpm, at about 25° C. ambient room temperature).

The inventive multi-purpose cationic associative polymers can be employed as emulsifiers, stabilizers, suspending agents, film formers, conditioners, moisturizers, spreading aids and carriers for enhancing the efficacy, deposition or delivery of chemically and physiologically active ingredients and cosmetic materials, and as vehicles for improving the psychosensory, and aesthetic properties of a formulation in which they are included. The cationic character of the cationic associative polymers makes them useful as anti-stats, and, under certain conditions, may also provide biocidal, bacteriostatic, preservative, and anti-microbial activity. The cationic associative polymers can be utilized in a variety of products for personal care, health care, household care, institutional and industrial (collectively "I&I") care, and in a variety of products for medical and industrial applications. The cationic associative polymers are preferably incorporated in compositions that are non-alkaline, i.e., acidic to substantially neutral in pH, but are not limited thereto.

The amount of cationic associative polymer that can be employed depends upon the purpose for which they are included in the formulation and can be readily determined by person skilled in the formulation arts. Thus, as long as the physicochemical and functional properties of the compositions containing a cationic associative polymer are achieved, a useful amount of cationic associative polymer, active weight percent, on a total composition weight basis, typically can vary in the range of about 0.01% to about 25%, but is not limited thereto. In a given composition or application, therefore, the cationic associative polymers of this invention can, but need not, serve more than one function, such as thickener and conditioner, film-former and carrier, and the like, as described in more detail below.

A polymer of this invention can be employed as a rheology modifier or emulsion stabilizing agent in conventional emulsion formulations by incorporating the polymer in the formulation at any step during the formation of an oil-in-water or water-in-oil or multiphase emulsion process. For example, a polymer, supplied as an aqueous emulsion product, can be included with the water phase components. In one preferred emulsion embodiment, the polymer is added to the formulation after the final emulsion has formed and cooled, adjusting the pH downward with an organic acid or mineral acid to optimize acid swelling to the desired viscosity, and then adjusting the final composition to the desired pH. If the pH of a completed composition or formulation containing an acid-swollen cationic associative polymer is more acidic than required for the intended use of the formulation, the pH can then be further adjusted with any, preferably physiologically tolerable, inorganic or organic base.

Compositions containing a cationic associative polymer can be packaged and dispensed from containers, such as jars, bottles, tubes, spray bottles, wipes, cans, roll-on containers, stick containers, and the like, without limitation. There is no limitation as to the form of product in which the cationic associative polymer can be incorporated, so long as the purpose for which the product is used is achieved. For example, personal care and health care products containing a cationic associative polymer can be applied to the skin, hair, scalp and nails in the form of, without being limited thereto, gels, sprays (liquid or foam), emulsions (creams, lotions, pastes), liquids (rinses, shampoos), bars, ointments, suppositories, impregnated wipes, patches, and the like.

The cationic associative polymers of the invention are suitable for the preparation of personal care (cosmetics, toiletries, cosmeceuticals) and topical health care products, including without limitation, hair care products, such as shampoos (including combination shampoos, such as "two-in-one" conditioning shampoos); post-shampoo rinses; setting and style maintenance agents including setting aids, such as gels and sprays, grooming aids, such as pomades, conditioners, perms, relaxers, hair smoothing products, and the like; skin care products (facial, body, hands, scalp and feet), such as creams, lotions, conditioners, and cleansing products; antiacne products; antiaging products (exfoliant, keratolytic, anticellulite, antiwrinkle, and the like); skin protectants such as sunscreens, sunblock, barrier creams, oils, silicones, and the like; skin color products (whiteners, lighteners, sunless tanning accelerators, and the like); hair colorants (hair dyes, hair color rinses, highlighters, bleaches and the like); pigmented skin colorants (face and body makeups, foundation creams, mascara, rouge, lip products, and the like); bath and shower products (body cleansers, body wash, shower gel, liquid soap, soap bars, syndet bars, conditioning liquid bath oil, bubble bath, bath powders, and the like); nail care products (polishes, polish removers, strengtheners, lengtheners, hardeners, cuticle removers, softeners, and the like); and any aqueous acidic to substantially neutral composition to which an effective amount of cationic associative polymer can be incorporated for achieving a beneficial or desirable, physical or chemical, effect therein during storage and/or usage.

Toiletries and health and beauty aids, commonly referred to as HBAs, containing a cationic associative polymer, can include, without limitation, hair-removal products (shaving creams and lotions, depilatories, after-shave skin conditioners, and the like); deodorants and antiperspirants; oral care products (mouth, teeth and gums), such as mouthwash, dentrifrice, such as toothpaste, tooth powder, tooth polishes, tooth whiteners, breath fresheners, denture adhesives, and the like; facial and body hair bleach; and the like. Other health and beauty aids that can contain cationic associate polymers, include, without limitation, sunless tanning applications containing artificial tanning accelerators, such as dihydroxyacetone (DHA), tyrosine, tyrosine esters, and the like; skin depigmenting, whitening, and lightening formulations containing such active ingredients as kojic acid, hydroquinone, arbutin, fruital, vegetal or plant extracts, (lemon peel extract, chamomile, green tea, paper mulberry extract, and the like), ascorbyl acid derivatives (ascorbyl palmitate, ascorbyl stearate, magnesium ascorbyl phosphate, and the like); foot care products, such as keratolytic corn and callous removers, foot soaks, foot powders (medicated, such as antifungal athlete's foot powder, ointments, sprays, and the like, and antiperspirant powders, or non-medicated moisture absorbent powder), liquid foot sprays (non-medicated, such as cooling, and deodorant sprays, and medicated antifungal sprays, antiperspirant sprays, and the like), and foot and toenail conditioners (lotions and creams, nail softeners, and the like).

Topical health and beauty aids that can include cationic associative polymers (e.g., as spreading aids and film formers) include, without being limited thereto, skin protective spray, cream, lotion, gel, stick and powder products, such as insect repellants, itch relief, antiseptics, disinfectants, sun blocks, sun screens, skin tightening and toning milks and lotions, wart removal compositions, and the like.

Cationic associative polymers are particularly useful as suspending agents for particulates, such as mica, pearlizing agents, beads, and the like, making them suitable for dermal products containing particulates, microabrasives, and abrasives, such as shower gels, masks and skin cleansers containing exfoliative scrub agents. Numerous cosmetically useful particulate exfoliating agents are known in the art, and the selection and amount is determined by the exfoliating effect desired from the use of the composition, as recognized by those skilled in the cosmetic arts. Useful exfoliating agents include, but are not limited to, biological abrasives, inorganic abrasives, synthetic polymers, and the like, and mixtures thereof. Biological abrasives include, without limitation, shell, seed, and kernel or stone granules or powders, obtained from nuts, such as from walnut (*Juglans regia*) shells, almonds, pecans, and the like; fruital sources, such as apricots, avocados, coconuts, olives, peaches, and the like; vegetal sources, such as corn cob, oat bran, rice, rose hip seed, jojoba (wax, seed powder), microcrystalline cellulose, ground loofa, ground seaweed, and the like; animal sources, such as oyster shell, silk, microcrystalline collagen, and the like. Inorganic abrasives include, without limitation, stannic oxide, talc, silica (hydrated, colloidal and the like), kaolin, precipitated chalk, salts (sodium chloride, dead sea salt, and the like), ground pumice, and the like. Synthetic polymers include, without limitation, microcrystalline polyamides (nylons), microcrystalline polyesters (polycarbonates), and the like. The polymers of the present invention are also useful for suspending gaseous bubbles in a liquid medium.

The cationic associative polymers are useful as thickeners and film-formers in a variety of dermatological, cosmeceutical compositions employed for topically ameliorating skin conditions caused by drying, photodamage, aging, acne, and the like, containing conditioners, moisturizers, antioxidants, exfoliants, keratolytic agents, vitamins, and the like, typically containing an active acidic ingredient and having a pH in the range of about 0.5 to about 5. When a cationic associative polymer is incorporated into these foregoing acidic product embodiments, the active acid ingredient can serve as both the active skin treatment agent and acid swelling agent for the cationic associative polymer to achieve the desired viscosity.

In one cosmeceutical aspect, a cationic associative polymer can be employed as a thickener for active skin treatment lotions and creams containing, as active ingredients, acidic anti-aging, anti-cellulite, and anti-acne agents, hydroxy carboxylic acids, such as alpha-hydroxy acid (AHA), beta-hydroxy acid (BHA), alpha-amino acid, alpha-keto acids (AKAs), and mixtures thereof. In such cosmeceuticals, AHAs can include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, azelaic acid, alpha-lipoic acid, salicylic acid, AHA salts and derivatives, such as arginine glycolate, ammonium glycolate, sodium glycolate, arginine lactate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. BHAs can include, but are not limited to, 3-hydroxy propanoic acid, beta-hydroxybutyric acid, beta-phenyl lactic acid, beta-phenylpyruvic acid, and the like. Alpha-amino acids include, without being limited thereto, alpha-amino dicarboxylic acids, such as aspartic acid, glutamic acid, and mixtures thereof, sometimes employed in combination with fruit acid. AKAs include pyruvic acid. In some antiaging compositions, the acidic active agent may be retinoic acid, a halo-carboxylic acid, such as trichloroacetic acid, an acidic antioxidant, such as ascorbic acid (vitamin C), a mineral acid, phytic acid, lysophosphatidic acid, and the like. Some acidic anti-acne actives, for example, can include salicylic acid, derivatives of salicylic acid, such as 5-octanoylsalicylic acid, retinoic acid, and its derivatives.

A discussion of the use and formulation of active skin treatment compositions is in COSMETICS & TOILETRIES®, C&T Ingredient Resource Series, "AHAs & Cellulite Products How They Work", published 1995, and "Cosmeceuticals", published 1998, both available from Allured Publishing Corporation, incorporated herein by reference. Compositions containing alpha-amino acids acidified with ascorbic acid are described in U.S. No. 6,197,317 B1, and a commercial cosmeceutical preparation utilizing these acids in an anti-aging, skin care regimen is sold under the tradename, AFAs, by exCel Cosmeceuticals (Bloomfield Hills, Mich.). The term "AFA", as described in the supplier's trade literature, was coined by the developer to describe the amino acid/vitamin C combination as Amino Fruit Acids and as the acronym for "Amino acid Filaggrin based Antioxidants."

Other health care products in which cationic associate polymers can be included are medical products, such as topical and non-topical pharmaceuticals, and devices. In the formulation of pharmaceuticals, a cationic associative polymer can be employed as a thickener and/or lubricant in such products as creams, pomades, gels, pastes, ointments, tablets, gel capsules, purgative fluids (enemas, emetics, colonics, and the like), suppositories, anti-fungal foams, eye products (ophthalmic products, such as eyedrops, artificial tears, glaucoma drug delivery drops, contact lens cleaner, and the like), ear products (wax softeners, wax removers, otitis drug delivery drops, and the like), nasal products (drops, ointments, sprays, and the like), and wound care (liquid bandages, wound dressings, antibiotic creams, ointments, and the like), without limitation thereto.

The film-forming and acid-swellable character of the cationic associative polymer makes the cationic associative polymer particularly suitable as a vehicle for topical medical compositions for promoting and enhancing the transdermal delivery of active ingredients to or through the skin, for enhancing the efficacy of anti-acne agents formulations and topical analgesics, and for controlling release of drugs, such as antacids from tablets, or syrups, at low pH, such as in the stomach; controlling drug release from tablets, lozenges, chewables, and the like in the mildly acidic environment of the mouth; or from suppositories, ointments, creams, and the like in the mildly acidic environment of the vagina; to promote deposition of dandruff control agents from shampoos, salves, and the like; to enhance the deposition of colorants on skin from pigmented cosmetics (makeups, lipsticks, rouges, and the like) and on hair from hair dyes, and the like.

In addition to the foregoing, the cationic character of the polymers of the present invention at acid pH, and its surprising cationic compatibility, makes the cationic associative polymer useful as a thickener for antistatic, biocidal, antimicrobial, and other preservative compositions, in a variety of personal care, health care, I&I, and medical applications. For example, the polymer can be employed as a thickener in over-the-counter (OTC) health care and pharmaceutical products where cationic biocides are typically employed, such as in oral care compositions for plaque and tartar control, and liquid vehicles containing therapeutic agents, such as syrups, gels, and the like. Under certain controlled pH conditions, the cationic character of the cationic associative polymer, itself, may also provide antistatic activity or biocidal, antimicrobial, or like preservative activity.

The polymers of the present invention can be employed, without being limited thereto, as a lubricant coating for medical devices, such as soft tissue implants, surgical gloves, catheters, cannulae, and the like, as removable protective film coatings for medical instruments, wound dressings, and the like, as a muco-adhesive, especially in the acid environment of the stomach, as a carrier and thickener in formulated products for medical applications, such as disinfectant hand creams, antiviral products (for anionic viruses), antibiotic ointments, sprays and creams, non-drip, sprayable disinfectant in hospitals, hard surface antimicrobial finish applied during routine maintenance, and the like.

The polymers of the present invention can be used in home care, and I&I applications, for example, as a rheology modifier, fabric conditioning agent, antistatic agent, especially to improve formulation efficiency through "cling-on-surface" or improving efficacy of disinfectants, and biocidal formulations, and to synergistically improve fabric softening efficacy in combination with traditional fabric softeners. Typical household and I&I products that may contain polymers of the invention, include, without being limited thereto, laundry and fabric care products, such as detergents, fabric softeners (liquids or sheets), ironing sprays, dry cleaning aids, antiwrinkle sprays, spot removers and the like; hard surface cleansers for the kitchen and bathroom and utilities and appliances employed or located therein, such as toilet bowl gels, tub and shower cleaners, hard water deposit removers, floor and tile cleansers, wall cleansers, floor and chrome fixture polishes, alkali-strippable vinyl floor cleaners, marble and ceramic cleaners, air freshener gels, liquid cleansers for dishes, and the like; disinfectant cleaners, such as toilet bowl and bidet cleaners, disinfectant hand soaps, room deodorizers, and the like.

The polymers of the present invention can be utilized as rheology modifiers, dispersants, stabilizers, promoters, or antimicrobials, and the like, in industrial product applications, such as, without being limited thereto, textiles (processing, finishing, printing, and dyeing aids, protective washable surface coatings, manufacture of synthetic leather by saturation of non-woven fabrics, and the like, manufacturing of woven fabrics, non-woven fabrics, natural and synthetic fibers and the like); water treatments (waste water, cooling water, potable water purification, and the like); chemical spill containments (acid-spill absorbent, and the like); leather and hide processing (processing aids, finishing, coating, embossing, and the like); paper and papermaking (surface coatings, such as pigmented coatings, antistatic coatings, and the like, pulp binders, surface sizings, dry and wet strength enhancers, manufacture of wet-laid felts, and the like); printing (inks, antiwicking ink-jet printer inks, thickeners for ink formulations containing cationic dyes for printing acrylic fabrics, and the like); paints (pigment and grinding additive, crosslinking agent for epoxy latex emulsions, particulate-suspending aid for clays, pigments, and the like); industrial plant effluent treatment (flocculents for phenolics in paper mill effluent, and the like); metal working (acid etch cleaners, low pH metal coatings, pickling agents in cold rolled steel processing, and the like); adhesives (clear adhesives, adhesion promoters for metal, plastic, wood, and the like, non-woven floc adhesive tie coatings, bonding, and the like); wood preservation; and industrial construction products for buildings and roads (cement plasticizers, asphalt emulsion stabilizers at low pH, acid etch for cement, consistency modifiers of concrete, mortar, putty, and the like). The polymers of the present invention are particularly useful as thickeners for rust removers, acid truck cleaners, scale removers, and the like, and as dispersion stabilizers of products containing particulates, such as clay, pigments (titanium dioxide, calcium carbonate, and other minerals), abrasives, and the like, employed in a variety of the foregoing industrial applications, and in drilling muds.

Products containing polymers of the present invention can contain various conventional additives and adjuvants known in the art, some of which can serve more than one function. The amounts employed will vary with the purpose and character of the product and can be readily determined by one skilled in the formulation arts and from the literature. The term "cosmetic adjuvant" includes cosmetically and pharmaceutically acceptable product stabilizing and product finishing agents that maintain the physical stability of the composition and its visible aesthetic appearance and market appeal during the useful shelf life of the composition.

The term "fixative" as applied to polymers encompasses the properties of film-formation, adhesion, or coating deposited on a surface on which the polymer is applied. The terms "hair styling and hair fixative" as commonly understood in the hair care arts, and as used herein, refer collectively to hair setting agents that are hair fixatives and film formers and which are topically applied to the hair to actively contribute to the ease of styling and/or holding of a hair set, and to maintain the restylability of the hair set. Hence, hair setting compositions include hair styling, hair fixative, and hair grooming products that conventionally are applied to the hair (wet or dry) in the form of gels, rinses, emulsions (oil-in-water, water-in-oil or multiphase), such as lotions and creams, pomades, sprays (pressurized or non-pressurized), spritzes, foams, such as mousses, shampoos, solids, such as sticks, semisolids and the like, or are applied from a hair setting aid having the hair setting composition impregnated therein or coated thereon, to leave the hair setting agent in contact on the hair for some period until removed, as by washing.

The term "conditioning agents", and grammatical variations thereof, as it relates to compositions for skin care and hair care includes cosmetically and pharmaceutically useful materials that are humectants, moisturizers, and emollients. It is recognized that some conditioning agents can serve more than one function in a composition, such as emulsifying agents, lubricants, and solvents.

A preferred hair care composition embodiment comprises a polymer of the present invention in an amount effective to provide to the hair care composition a property, such as a hair fixative property, a hair conditioning property, a viscid property (thickening, rheology modifying), or a combination thereof. Optionally, the hair care composition can include one or more auxiliary film-forming agent, auxiliary hair-fixative agent, auxiliary hair conditioning agent, auxiliary rheology modifying agent, or a mixture thereof.

A preferred skin care composition embodiment comprises a polymer of the present invention in an amount effective to provide to the skin care composition a property, such as a skin conditioning property, a viscid property (thickening, rheology modifying), or a combination thereof. Optionally, the skin care composition can include one or more auxiliary skin conditioning agent, auxiliary rheology modifying agent, or a mixture thereof.

Product formulations comprising a polymer of this invention can contain various additives and cosmetic adjuvants, conventionally or popularly included in personal care, household care, institutional care, and industrial care products, and in industrial processes, including, without being limited thereto, acidifying or alkalizing pH adjusting agents and buffering agents; auxiliary fixatives and film formers, such as nonionic, anionic, cationic, or amphoteric polymers of synthetic or natural origin, and the like; auxiliary rheology modifiers, such as viscosity-increasing polymeric, gum, or resin thickeners or gellants; additives, such as emulsifiers, emulsion stabilizers, waxes, dispersants, and the like, and viscosity control agents, such as solvents, electrolytes, and the like; auxiliary conditioning agents, such as antistatic agents, synthetic oils, vegetable or animal oils, silicone oils, monomeric or polymeric quaternized ammonium compounds and derivatives thereof, sheen enhancers, moisturizers, emollients, humectants, lubricants, sunscreen agents, and the like; oxidizing agents; reducing agents; surfactants, such as anionic, cationic, nonionic, amphoteric, zwitterionic surfactants, and silicone derivatives thereof; polymer film modifying agents, such as plasticizers, tackifiers, detackifiers, wetting agents, and the like; product stabilizing and finishing agents, such as chelating agents, opacifiers, pearlescing agents, proteinaceous materials and derivatives thereof, vitamins and derivatives thereof, preservatives, fragrances, solubilizers, colorants (temporary or permanent), such as pigments and dyes, UV absorbers, and the like; propellants (water-miscible or water-immiscible), such as fluorinated hydrocarbons, liquid volatile hydrocarbons, compressed gases, and the like; and mixtures thereof.

Additives and adjuvant ingredients, products, or materials, which may be employed with the inventive cationic associative polymers discussed herein will be referred to by the international nomenclature commonly referred to as INCI name given them in the *International Cosmetic Ingredient Dictionary*, published by the Cosmetic, Toiletry, and Fragrance Association, Washington D.C. (hereafter INCI Dictionary), such as can be found in any edition thereof, for example, Volumes 1 and 2, Sixth Edition, (1995) or Volumes 1-3, Seventh and Eighth Editions, (1997, 2000), or by their commonly used chemical names. Numerous commercial suppliers of materials listed by INCI name, trade name or both can be found in the INCI Dictionary and in numerous commercial trade publications, including but not limited to the 2001 *McCutcheon's* Directories, Volume 1: Emulsifiers & Detergents and Volume 2: Functional Materials, published by McCutcheon's Division, The Manufacturing Confectioner Publishing Co., Glen Rock, N.J. (2001); and 2001 *Cosmetic Bench Reference*, edition of *COSMETICS & TOILETRIES*® 115 (13), published by Allured Publishing Corporation, Carol Stream, Ill. (2001); the relevant disclosures of each are incorporated herein by reference. Such components and the formulation of compositions are also described in detail in well known references, such as *Cosmetics Science and Technology*, First Edition (Sagarin (ed)), published 1957, and Second Edition (Balsam, et al. (eds)), published 1972-74; and *The Chemistry and Manufacture of Cosmetics*, Second Edition (deNavarre (ed)), published 1975, and Third Edition (Schlossman (ed)), published 2000, both available from Allured Publishing Corporation; Rieger (ed), *Harry's Cosmeticology*, 8th Edition, Chemical Publishing, Co., Inc., New York, N.Y. (2000); and various formularies available to those skilled in the pharmaceutical arts, such as *Remington's Pharmaceutical Sciences*, Fourteenth Edition, Mack Publishing Company, Easton, Pa. (1970); the relevant disclosures of each are incorporated herein by reference.

It is known that formulated compositions for personal care and topical, dermatological, health care, which are applied to the skin and mucous membranes for cleansing or soothing, are compounded with many of the same or similar physiologically tolerable ingredients and formulated in the same or similar product forms, differing primarily in the purity grade of ingredient selected, by the presence of medicaments or pharmaceutically accepted compounds, and by the controlled conditions under which products may be manufactured. Likewise, many of the ingredients employed in products for households, and I&I are the same or similar to the foregoing, differing primarily in the amounts and material grade employed. It is also known that the selection and permitted amount of ingredients also may be subject to governmental regulations, on a national, regional, local, and international level. Thus, discussion herein of various useful ingredients for personal care and health care products may apply to household and I&I products and industrial applications.

The choice and amount of ingredients in formulated compositions containing a cationic associative polymer will vary depending on the product and its function, as is well known to those skilled in the formulation arts. Formulation ingredients for personal care and topical health care products typically can include, but are not limited to, solvents, surfactants (as cleansing agents, emulsifying agents, foam boosters, hydrotropes, solubilizing agents, and suspending agents), nonsurfactant suspending agents, emulsifiers, skin conditioning agents (emollients, humectants, moisturizers, and the like), hair conditioning agents, hair fixatives, film-formers, skin protectants, binders, chelating agents, antimicrobial agents, antifungal agents, antidandruff agents, abrasives, adhesives, absorbents, dyes, deodorant agents, antiperspirant agents, opacifying and pearlescing agents, antioxidants, preservatives, propellants, spreading aids, sunscreen agents, sunless skin tanning accelerators, ultraviolet light absorbers, pH adjusting agents, botanicals, hair colorants, oxidizing agents, reducing agents, skin bleaching agents, pigments, physiologically active agents, anti-inflammatory agents, topical anesthetics, fragrance and fragrance solubilizers, and the like, in addition to ingredients previously discussed that may not appear herein. Oral care products, for example, can contain anticaries, antitartar and/or antiplaque agents in addition to surfactants, abrasives, humectants, and flavorants. An extensive listing of substances and their conventional functions and product categories appears in the INCI Dictionary, generally, and in Vol. 2, Sections 4 and 5 of the Seventh Edition, in particular, incorporated herein by reference.

The polymers of the present invention prepared as aqueous emulsions are particularly useful for water-based formulations, and formulations containing water-miscible auxiliary solvents, but are not limited thereto. Useful solvents commonly employed are typically liquids, such as water (deionized, distilled or purified), alcohols, polyols, and the like, and mixtures thereof. Non-aqueous or hydrophobic auxiliary solvents are commonly employed in substantially water-free products, such as nail lacquers, aerosol propellant sprays, or for specific functions, such as removal of oily soils, sebum, make-up, or for dissolving dyes, fragrances, and the like, or are incorporated in the oily phase of an emulsion. Non-limiting examples of auxiliary solvents, other than water, include linear and branched alcohols, such as ethanol, propanol, isopropanol, hexanol, and the like; aromatic alcohols, such as benzyl alcohol, cyclohexanol, and the like; saturated $C_{12}$-$C_{30}$ fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, $C_2$-$C_4$ alkoxylated alcohols and $C_2$-$C_4$ alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Non-limiting examples of non-aqueous auxiliary solvents include silicones, and silicone derivatives, such as cyclomethicone, and the like, ketones such as acetone and methylethyl ketone; natural and synthetic oils and waxes, such as vegetable oils, plant oils, animal oils, essential oils, mineral oils, $C_7$-$C_{40}$ isoparaffins, alkyl carboxylic esters, such as ethyl acetate, amyl acetate, ethyl lactate, and the like, jojoba oil, shark liver oil, and the like. Some of the foregoing non-aqueous auxiliary solvents may also be conditioners and emulsifiers.

Surfactants are generally employed as cleansing agents, emulsifying agents, foam boosters, hydrotropes and suspending agents. The polymers of the present invention may be employed in formulations containing all classes of surfactants, i.e., anionic surfactants, cationic surfactants, nonionic surfactants, amphoteric surfactants. The term "amphoteric surfactant" as used herein includes zwitterionic surfactants. In addition to the foregoing references, discussions of the classes of surfactants are in *Cosmetics & Toiletries®C&T Ingredient Resource Series*, "Surfactant Encyclopedia", 2nd Edition, Rieger (ed), Allured Publishing Corporation (1996); Schwartz, et al., *Surface Active Agents, Their Chemistry and Technology*, published 1949; and *Surface Active Agents and Detergents*, Volume II, published 1958, Interscience Publishers; each incorporated herein by reference.

Surprisingly, the polymers of the present invention are useful as thickeners and deposition aids in compositions containing a relatively high concentration (about 10-40 weight percent) of anionic surfactant, such as shampoos and two-in-one type liquid conditioning/cleansers for hair and body (bath) products. The present cationic associative polymers are compatible with cationic surfactants having antistatic activity, such as are employed in hair care products and fabric care products.

Anionic surfactants include substances having a negatively charged hydrophobe or that carry a negative charge when the pH is elevated to neutrality or above, such as acylamino acids, and salts thereof, for example, acylglutamates, acyl peptides, sarcosinates, and taurates; carboxylic acids, and salts thereof, for example, alkanolic acids and alkanoates, ester carboxylic acids, and ether carboxylic acids; phosphoric acid ester and salts thereof; sulfonic acids and salts thereof, for example, acyl isethionates, alkylaryl sulfonates, alkyl sulfonates, and sulfosuccinates; and sulfuric acid esters, such as alkyl ether sulfates and alkyl sulfates.

Non-limiting examples of anionic surfactants include mono-basic salts of acylglutamates that are slightly acidic in aqueous solution, such as sodium acylglutamate and sodium hydrogenated tallow glutamate; salts of acyl-hydrolyzed protein, such as potassium, palmitoyl hydrolyzed milk protein, sodium cocoyl hydrolyzed soy protein, and TEA-abietoyl hydrolyzed collagen; salts of acyl sarcosinates, such as ammonium myristoyl sarcosine, sodium cocoyl sarcosinate, and TEA-lauroyl sarcosinate; salts of sodium methyl acyltaurates, such as sodium lauroyl taurate and sodium methyl cocoyl taurate; alkanoic acids and alkanoates, such as fatty acids derived from animal and vegetable glycerides that form water-soluble soaps and water-insoluble emulsifying soaps, including sodium stearate, aluminum stearate, and zinc undecylenate; ester carboxylic acids, such as dinonoxynol-9-citrate; salts of acyl lactylates such as calcium stearoyl lactylate and laureth-6 citrate; ethercarboxylic acids derived from ethyoxylated alcohols or phenols having varying lengths of polyoxyethylene chains, such as nonoxynol-8 carboxylic acid, and sodium trideceth-13 carboxylate; mono- and di-esters of phosphoric acid and their salts, such as phospholipids, dilaureth-4-phosphate, DEA-oleth-10 phosphate and triethanolamine lauryl phosphate; salts of acylisethionate, such as sodium cocoyl isethionate; alkylarylbenzene sulfonates, such as alpha-olefin sulfonate (AOS) and alkali metal, alkaline earth metal, and alkanolamine salts thereof, and sodium dodecylbenzene sulfonate; alkyl sulfonates, such as sodium $C_{12}$-$C_{14}$ olefin sulfonate, sodium cocomonoglyceride sulfonate, sodium $C_{12}$-$C_{15}$ pareth-15 sulfonate, and sodium lauryl sulfoacetate; sulfosuccinates, such as mono- and di-esters of sulfosuccinic acid, salts thereof and alkoxylated alkyl and alkylamido derivatives thereof, such as di-$C_4$-$C_{10}$ alkyl sodium sulfosuccinate, disodium laureth sulfosuccinate, disodium oleamido MEA-sulfosuccinate, and disodium $C_{12}$-$C_{15}$, pareth sulfosuccinate; alkyl ether sulfates, such as sodium and ammonium lauryl ether sulfate (having about 1 to about 12 moles ethylene oxide); alkyl sulfates, such as sodium, ammonium and triethanolamine salts of $C_{12}$-$C_{18}$ alkylsulfates, sodium $C_{12}$-$C_{14}$ olefin sulfates, sodium laureth-6 carboxylate, sodium $C_{12}$-$C_{18}$ pareth sulfate, and the like.

Cationic surfactants can have a hydrophobe that carries a positive charge or that is uncharged at pH values close to neutrality or lower, such as alkylamines, alkyl imidazolines, ethoxylated amines, and quaternary ammonium compounds. Cationic surfactants used in cosmetics are preferably N-derivatives and the neutralizing anion may be inorganic or organic. Among the cationic surfactant materials useful herein are quaternary ammonium compounds corresponding to the general formula: $(R^{10}R^{11}R^{12}R^{13}N^+)$ $E^-$, wherein each of $R^{10}$, $R^{11}$, $R^{12}$, and $R^{13}$ are independently selected from an aliphatic group having from 1 to about 22 carbon atoms, or an aromatic, alkoxy, polyoxyalkylene, alkylamido, hydroxyalkyl, aryl or alkylaryl group having 1 to about 22 carbon atoms in the alkyl chain; and $E^-$ is a salt-forming anion such as those selected from halogen, (e.g. chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated.

Alkylamines can be salts of primary, secondary and tertiary fatty $C_{12}$-$C_{22}$ alkylamines, substituted or unsubstituted, and substances sometimes referred to as "amidoamines". Non-limiting examples of alkyl amines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane). Non-limiting examples of amidoamines and salts thereof include stearamido propyl dimethyl amine, stearamidopropyl dimethylamine citrate, palmitamidopropyl diethylamine, and cocamidopropyl dimethylamine lactate. Other cationic surfactants include distearyldimonium chloride, dicetyldimonium chloride, guar hydroxypropyltrimonium chloride, and the like. At low pH, amine oxides may protonate and behave similarly to N-alkyl amines.

Non-limiting examples of alkyl imidazolines include alkyl hydroxyethyl imidazoline, such as stearyl hydroxyethyl imidazoline, coco hydroxyethyl imidazoline, ethyl hydroxymethyl oleyl oxazoline, and the like. Non-limiting examples of ethyoxylated amines include PEG-cocopolyamine, PEG-15 tallow amine, quaternium-52, and the like.

Quaternary ammonium compounds are monomeric or polymeric materials containing at least one nitrogen atom that is linked covalently to four alkyl and/or aryl substituents, and the nitrogen atom remains positively charged regardless of the environmental pH. Quaternary ammonium compounds comprise a large number of substances that are used extensively as surfactants, conditioners, antistatic agents, and antimicrobial agents and include, alkylbenzyldimethyl ammonium salts, alkyl betaines, heterocyclic ammonium salts, and tetraalkylammonium salts. Long-chain (fatty) alkylbenzyldimethyl ammonium salts are preferred as conditioners, as antistatic agents, and as fabric softeners, discussed in more detail below. Other quaternary ammonium compounds include quaternary ammonium silicones.

Non-limiting examples of alkylbenzyldimethylammonium salts include stearalkonium chloride, benzalkonium chloride, quaternium-63, olealkonium chloride, didecyldimonium chloride, and the like. Alkyl betaine compounds include alkylamidopropyl betaine, alkylamidopropyl hydroxysultaine, and sodium alkylamido propyl hydroxyphostaine. Non-limiting examples of alkyl betaine compounds include oleyl betaine, coco-betaine, cocoamidopropyl betaine, coco-hydroxy sultaine, coco/oleamidopropyl betaine, coco-sultaine, cocoamidopropylhydroxy sultaine, and sodium lauramidopropyl hydroxyphostaine. Heterocyclic ammonium salts include alkylethyl morpholinium ethosulfate, isostearyl ethylimidonium ethosulfate, and alkylpyridinium chlorides, and are generally used as emulsifying agents. Non-limiting examples of heterocyclic ammonium salts include cetylpyridinium chloride, isostearylethylimidonium ethosulfate, and the like. Non-limiting examples of tetraalkylammonium salts include cocamidopropyl ethyldimonium ethosulfate, hydroxyethyl cetyldimonium chloride, quaternium-18, and cocodimonium hyroxypropyl hydrolyzed protein, such as hair keratin, and the like.

The polymers of the present invention are surprisingly compatible with cationic surfactants and other cationic compounds suitable as antistatic agents. The term "antistatic agents" refers to ingredients that alter the electrical properties of cosmetic raw materials or of human body surfaces (skin, hair, etc.) and textiles, for example, by reducing their tendency to acquire an electrical charge and thus, can condition hair, skin and fabrics. The cationic compatibility of the cationic associative polymers makes them suitable for incorporation into formulations containing antistatic agents typically employed in hair care compositions, such as shampoos, post-shampoo conditioning rinses, hair sprays, hair dressings and the like. The antistatic agent can be employed in amounts up to about 30 weight percent of the final composition, but is not limited thereto.

Antistatic agents include, but are not limited to, quaternary ammonium compounds, protein derivatives, synthetic quaternary ammonium polymers, amines, protonated amine oxides, betaines, and the like, which may act as antistatic agents in specific formulations and under controlled pH conditions in addition to any surfactant properties imparted by such materials. In addition to antistatic agents previously discussed, non-limiting examples of quaternary ammonium compounds useful as antistatic agents are acetamidopropyl trimonium chloride, behenamidopropyl dimethylamine, behenamidopropyl ethyldimonium ethosulfate, behentrimonium chloride, cetethyl morpholinium ethosulfate, cetrimonium chloride, cocoamidopropyl ethyldimonium ethosulfate, dicetyldimonium chloride, dimethicone hydroxypropyl trimonium chloride, hydroxyethyl behenamidopropyl dimonium chloride, quaternium-26, quaternium-27, quaternium-53, quaternium-63, quaternium-70, quaternium-72, quaternium-76 hydrolyzed collagen, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, and the like.

Synthetic quaternary ammonium polymers, include film-forming polymers and conditioning polymers. Non-limiting examples of synthetic quaternary ammonium polymers include polymers and copolymers of dimethyl diallyl ammonium chloride, such as polyquaternium-4, polyquaternium-6, polyquaternium-7, polyquaternium-22, polyquaternium-10, polyquaternium-11 polyquaternium-15, polyquaternium-16, polyquaternium-24, polyquaternium-28, polyquaternium-32, polyquaternium-33, polyquaternium-35, polyquaternium-37, polyquaternium-39, polyquaternium-44, PEG-2-cocomonium chloride, quaternium-52, and the like.

The term "hair setting composition" encompasses products comprising at least one polymer of the present invention as a hair setting agent, which are applied to the hair (wet or dry) before, during or after configuring the hair into the shape (curly or straight) desired, without limitation as to product form.

The polymers of the present invention are surprisingly useful in hair setting and hair styling compositions as the sole film-forming, rheology modifying, conditioning fixative agent. The polymers of the present invention are also useful in combination with commercially available auxiliary hair fixative polymers, such as nonionic, cationic, and amphoteric hair setting polymers, cationic conditioning polymers, and combinations thereof. It was surprisingly found that unexpectedly increased viscosity and hair setting efficacy properties were produced by appropriate combinations of a polymer of the present invention with an auxiliary conventional hair fixative and/or hair conditioning polymer. Conventional polymeric hair fixative and hair styling polymers, well known in the art, include natural gums and resins and neutral or anionic polymers of synthetic origin. Listings of commercially available hair fixative and conditioning fixative polymers can be readily found in the INCI Dictionary, in supplier websites, and in the trade literature. See, for example, the Polymer Encyclopedia published in *Cosmetics & Toiletries®*, 117(12), December 2002 (Allured Publishing Corporation, Carol Stream, Ill.), the relevant disclosures of which are incorporated herein by reference.

Suitable commercially available nonionic polymers (i.e., neutral) used as hair styling or fixative polymers include, without limitation thereto, polyvinylpyrrolidone (PVP), polyvinylpyrrolidone/vinylacetate copolymer (PVP/VA), and the like. Commercially available cationic fixative polymers include, without limitation thereto, polymers having the INCI name, polyquaternium, such as polyquaternium-4, a diallyldimonium chloride/hydroxyethylcellulose copolymer (such as CELQUAT® H-100, National Starch); polyquaternium-11, a quaternized vinyl pyrrolidone/dimethylaminoethyl methacrylate copolymer (such as GAFQUAT® 734, 755, 755N, ISP); polyquaternium-16, a quaternized vinyl pyrrolidone/vinylimidazolium chloride copolymer (such as LUVIQUAT® FC-370, BASF); polyquaternium-28, a vinylpyrrolidone/methacrylamidopropyltrimethylammonium chloride copolymer (such as GAFQUAT® HS-100, ISP); polyquaternium-46, a quaternized vinylcaprolactam/vinylpyrrolidone/methylvinylimidazolium methosulfate copolymer; polyquaternium-55, a quaternized vinylpyrrolidone/dimethylaminopropylmethylacrylamide/lauryldimethylpropylmethacrylamidoammonium chloride copolymer (such as STYLEZE™ W, ISP), and the like; and amino-substituted polymers which are cationic under acidic pH conditions, such as vinylcaprolactam/PVP/dimethylaminoethylmethacrylate copolymer (such as GAFFIX® VC-713, ISP); PVP/dimethylaminoethylmethacrylate copolymer (such as Copolymer 845, ISP), PVP/DMAPA acrylates copolymer (such as STYLEZE™ CC-10, ISP), the pyrrolidone carboxylic acid salt of chitosan, having the INCI name, Chitosan PCA (such as KYTAMER® PC, Amerchol), and the like.

Suitable amphoteric fixative polymers include, without limitation thereto, octylacryamide/acrylates/butylaminoethylmethacrylate copolymer (such as the AMPHOMER® polymers, National Starch), acrylates/lauryl acrylate/stearyl acrylate/ethylamine oxide methacrylate copolymers (such as the DIAFORMER® polymers, Clariant Corp.), and the like.

Suitable commercial conditioning polymers include polymeric quaternary ammonium salts such as, without being limited thereto, polyquaternium-7, a polymeric quaternary ammonium salt of acrylamide and dimethyl diallylammonium chloride monomers (such as MACKERNIUM™-007, McIntyre Group, Ltd.); polyquaternium-10, a polymeric quaternary ammonium salt of hydroxyethylcellulose reacted with a trimethylammonium substituted epoxide (such as the UCARE® Polymers JR, LK, LR, SR series, Amerchol and CELQUAT® SC series, National Starch); polyquaternium-39, a polymeric quaternary ammonium salt of acrylic acid, diallyl dimethylammonium chloride and acrylamide (such as the MERQUAT® and MERQUAT® Plus polymers, Ondeo Nalco); quaternized derivatives of natural gums, e.g., guar hydroxypropyltrimonium chloride (such as the JAGUAR® and JAGUAR® Excel polymers, Rhodia, Inc.), and the like.

A number of quaternary ammonium compounds are used for fabric conditioning and fabric care, generally referred to as fabric softening agents, and are typically employed in amounts of up to about 20 weight percent of the total weight of the formulation, but are not limited thereto. Fabric softening agents useful in combination with the cationic associative polymers of the present invention generally include long-chain alkylated quaternary ammonium compounds such as dialkyldimethyl quaternary ammonium compounds, imidazoline quaternary compounds, amidoamine quaternary compounds, dialkyl ester quat derivatives of dihydroxypropyl ammonium compounds; dialkyl ester quat derivatives of methyltriethanol ammonium compounds, ester amide amine compounds, and diester quat derivatives of dimethyldiethanol ammonium chloride, as described in the review article by Whalley, "Fabric Conditioning Agents", *HAPPI*, pp. 55-58 (February 1995), incorporated herein by reference.

In addition to the previously discussed antistatic agents, non-limiting examples of dialkyldimethyl quaternary ammonium compounds, include N,N-dioleyl-N,N-dimethylammonium chloride, N,N-ditallowyl-N,N-dimethylammonium ethosulfate, N,N-di(hydrogenated-tallowyl)-N,N-dimethylammonium chloride, and the like. Non-limiting examples of imidazoline quaternary compounds include 1-N-methyl-3-N-tallowamidoethylimidazolium chloride, 3-methyl-1-tallowylamidoethyl-2-tallowylimidazolinium methylsulfate, available from Witco Chemical Company under the tradename VARISOFT® 475, and the like. Non-limiting examples of amidoamine quaternary compounds include N-alkyl-N-methyl-N,N-bis(2-tallowamidoethyl)ammonium salts where the alkyl group can be methyl, ethyl, hydroxyethyl, and the like. Non-limiting examples of dialkyl ester quat derivatives of dihydroxypropyl ammonium compounds include 1,2-ditallowoyloxy-3-N,N,N-trimethylammoniopropane chloride, 1,2-dicanoloyloxy-3-N,N,N-trimethylammoniopropane chloride, and the like.

In addition, other types of long chain (e.g. natural oil and fatty acid-derived) alkylated quaternary ammonium compounds are suitable fabric softening agents, including, but not limited, to N,N-di(alkyloxyethyl)-N,N-dimethylammonium salts such as N,N-di(tallowyloxyethyl)-N,N-dimethylammonium chloride, N,N-di(canolyloxyethyl)-N,N-dimethylammonium chloride, and the like; N,N-di(alkyloxyethyl)-N-methyl-N-(2-hydroxyethyl)ammonium salts such as N,N-di(tallowyloxyethyl)-N-methyl-N-(2-hydroxyethyl)ammonium chloride, N,N-di(canolyloxyethyl)-N-methyl-N-(2-hydroxyethyl)ammonium chloride, and the like; N,N-di(2-alkyloxy-2-oxoethyl)-N,N-dimethylammonium salts, such as N,N-di(2-tallowyloxy-2-oxoethyl)-N,N-dimethylammonium chloride, N,N-di(2-canolyloxy-2-oxoethyl)-N,N-dimethylammonium chloride, and the like; N,N-di(2-alkyloxyethylcarbonyloxyethyl)-N,N-dimethylammonium salts, such as N,N-di(2-tallowyloxyethylcarbonyloxyethyl)-N,N-dimethylammonium chloride, N,N-di(2-canolyloxyethylcarbonyloxyethyl)-N,N-dimethylammonium chloride, and the like; N-(2-alkanoyloxy-2-ethyl)-N-(2-alkyloxy-2-oxoethyl)-N,N-dimethyl ammonium salts, such as N-(2-tallowoyloxy-2-ethyl)-N-(2-tallowyloxy-2-oxoethyl)-N,N-dimethyl ammonium chloride, N-(2-canoloyloxy-2-ethyl)-N-(2-canolyloxy-2-oxoethyl)-N,N-dimethyl ammonium chloride, and the like; N,N,N-tri(alkyloxyethyl)-N-methyl ammonium salts, such as N,N,N-tri(tallowyloxyethyl)-N-methylammonium chloride, N,N,N-tri(canolyloxyethyl)-N-methylammonium chloride, and the like; N-(2-alkyloxy-2-oxoethyl)-N-alkyl-N,N-dimethyl ammonium salts, such as N-(2-tallowyloxy-2-oxoethyl)-N-tallowyl-N,N-dimethyl ammonium chloride, N-(2-canoloyloxy-2-oxoethyl)-N-canolyl-N,N-dimethyl ammonium chloride, and the like.

Preferably, the long-chain alkyl groups are derived from tallow, canola oil, or from palm oil, however, other alkyl groups derived from soybean oil and coconut oil, for example, are also suitable, as are lauryl, oleyl, ricinoleyl, stearyl, palmityl, and like fatty alkyl groups. The quaternary ammonium salt compounds can have any anionic group as a counter-ion, for example, chloride, bromide, methosulfate (i.e. methylsulfate), acetate, formate, sulfate, nitrate, and the like.

Examples of preferred quaternary ammonium fabric softening compounds include N-methyl-N,N-bis(tallowamidoethyl)-N-(2-hydroxyethyl)ammonium methylsulfate and N-methyl-N,N-bis(hydrogenated-tallowamidoethyl)-N-(2-hydroxyethyl) ammonium methylsulfate, each of which materials are available from Witco Chemical Company under the trade names VARISOFT® 222 and VARISOFT® 110, respectively; dialkyl esterquat derivatives of methyltriethanol ammonium salts such as the DEHYQUART® AU series of bis(acyloxyethyl) hydroxyethylmethylammonium methosulfate esterquats available from Cognis, such as DEHYQUART® AU35, AU46, AU56, and the like; and N,N-di(tallowoyloxyethyl)-N,N-dimethylammonium chloride, where the tallow chains are at least partially unsaturated. Other preferred fabric softening agents include the well-known dialkyldimethyl ammonium salts such as N,N-ditallowyl-N,N-dimethyl ammonium methylsulfate, N,N-di(hydrogenated-tallowyl)-N,N-dimethyl ammonium chloride, N,N-distearyl-N,N-dimethyl ammonium chloride, N,N-dibehenyl-N,N-dimethylammonium chloride, N,N-di(hydrogenated tallow)-N,N-dimethyl ammonium chloride (trade name ADOGEN® 442), N,N-ditallowyl-N,N-dimethyl ammonium chloride (trade name ADOGEN® 470, PRAEPAGEN® 3445), N,N-distearyl-N,N-dimethyl ammonium chloride (trade name AROSURF® TA-100), all available from Witco Chemical Company; N,N-dibehenyl-N,N-dimethyl ammonium chloride, sold under the trade name KEMAMINE® Q-2802C by Humko Chemical Division of Witco Chemical Corporation; and N,N-dimethyl-N-stearyl-N-benzylammonium chloride sold under the trade names VARISOFT® SDC by Witco Chemical Company and AMMONYX® 490 by Onyx Chemical Company.

Any of the foregoing fabric softening agents, and mixtures thereof, can be utilized in combination with the cationic associative polymers of the present invention, particularly in laundry and fabric care products. For ester-containing fabric softening agents, the pH of the compositions can influence the stability of the fabric softening agents, especially in prolonged storage conditions. The pH, as defined in the present context, is measured in the neat compositions at about 20° C. Preferably, the pH of the composition is less than about 6. For optimum hydrolytic stability of these compositions, the pH is preferably in the range of from about 2 to about 5, more preferably about 2.5 to about 3.5.

In addition to protein derivatives previously described, non-limiting examples of protein derivatives include cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl hydrolyzed silk amino acids, hydroxypropyl trimonium hydrolyzed collagen, hydroxypropyl trimonium hydrolyzed keratin, hydroxypropyl trimonium hydrolyzed silk, hydroxypropyl trimonium hydrolyzed rice bran, hydroxypropyl trimonium hydrolyzed soy protein, hydroxypropyl trimonium hydrolyzed vegetable protein, hydroxypropyl trimonium hydrolyzed wheat protein, soyethyldimonium ethosulfate, soyethyl morpholinium ethosulfate, and the like.

Nonionic surfactants are generally uncharged amphiphiles and usually are alkoxylated to varying degrees. Classes of nonionic surfactants include alcohols, alkanolamides, amine oxides, esters, and ethers. Nonionic alcohols are usually hydroxy derivatives of long-chain $C_8$-$C_{18}$ alkane hydrocarbons, such as cetearyl alcohol, hydrogenated tallow alcohol, lanolin alcohols, alkanolamides, and the like. Alkanolamides contain at least one alkoxyl or one polyoxyethylene grouping and include alkanol-derived amides, such as acylamide DEA, N-alkyl pyrrolidone, palmamide MEA, peanutamide MIPA, and the like and ethoxylated amides, such as PEG-50 tallow amide. Amine oxides include alkylamine oxides, such as lauramine oxide; and acylamidopropyl morpholine oxides, such as cocamidopropylamine oxide; and the like. Esters include ethoxylated carboxylic acids, such as PEG-8 dilaurate, PEG-8 laurate, and the like; ethoxylated glycerides, such as PEG-4 castor oil, PEG-120 glyceryl stearate, triolein PEG-6 esters, and the like; glycol esters and derivatives thereof, such as glycol stearate SE, propylene glycol ricinoleate, and the like; monoglycerides, such as glyceryl myristate, glyceryl palmitate lactate, and the like; polyglyceryl esters, such as polyglyceryl-6-distearate, polyglyceryl-4 oleyl ether, and the like, polyhydric alcohol esters and ethers, such as methyl gluceth-20 sesquistearate, sucrose distearate; and the like; sorbitan/sorbitol esters, such as polysorbate-60, sorbitan sequiisostearate, and the like; and triesters of phosphoric acid, such as trideceth-3 phosphate, trioleth-8 phosphate, and the like. Ethers include ethoxylated alcohols, such as ceteareth-10, nonoxynol-9, and the like; ethoxylated lanolin, such as PEG-20 lanolin, PPG-12-PEG-65 lanolin oil, and the like; ethoxylated polysiloxanes, such as dimethicone copolyol, and the like; propoxylated POE ethers, such as meroxapol 314, poloxamer 122, PPG-5-ceteth-20, and the like; and alkyl polyglycosides, such as lauryl glucose, and the like.

Nonionic surfactants can be used as emulsifiers, suspending agents, solubilizers, foam boosters, and in some cases, as hydrotropes. Non-limiting examples of generally preferred nonionic surfactants include linear or branched alcohol ethoxylates, $C_8$-$C_{12}$ alkylphenol alkoxylates, such as octylphenol ethoxylates, polyoxyethylene polyoxypropylene block copolymers, and the like; $C_8$-$C_{22}$ fatty acid esters of polyoxyethylene glycol mono- and di-glycerides; sorbitan esters and ethoxylated sorbitan esters; $C_8$-$C_{22}$ fatty acid glycol esters; block copolymers of ethylene oxide and propylene oxide; and the like. Non-limiting examples of surfactant foam boosters or hydrotropes include alkanolamides, such as acetamide MEA, monoethanolamide, diethanolamide, cocamide DEA, isopropanolamide, and the like; amine oxides, such as hydrogenated tallowamine oxide; short chain alkyl aryl sulfonates, such as sodium toluene sulfonate; sulfosuccinates, such as disodium stearyl sulfosuccinate; and the like.

Amphoteric and zwitterionic surfactants are those compounds that have the capacity of behaving either as an acid or a base, by carrying a positive charge in strongly acidic media, carrying a negative charge in strongly basic media, and forming zwitterionic species at intermediate pH. The major classes of amphoteric surfactants are acyl/dialkyl ethylenediamines and derivatives thereof, such as disodium cocoamphocarboxymethylhydroxy-propyl sulfate, disodium cocamphodipropionate, sodium cocoamphoacetate, sodium lauroampho PG-acetatephosphate, sodium tallowamphopropionate, sodium undecylenoamphopropionate, and the like; and N-alkylamino acids, such as aminopropyl laurylglutamide, dihydroxyethyl soya glycinate, lauraminopropionic acid, and the like.

Some suitable zwitterionic surfactants for use in the present compositions include those broadly described as derivatives of aliphatic quaternary ammonium, phosphonium, and sulfonium compounds, wherein which the aliphatic radicals can be straight chain or branched, and wherein one of the aliphatic substituents contains about 8 to about 18 carbon atoms and another substituent contains an anionic water-solubilizing group, such as carboxy, sulfonate, sulfate, phosphate, phosphonate, and the like. Classes of zwitterionics include alkylamino sulfonates, alkyl betaines and alkylamido betaines, such as stearamidopropyldimethylamine, diethylaminoethylstearamide, dimethylstearamine, dimethylsoyamine, soyamine, myristylamine, tridecylamine, ethylstearylamine, N-tallowpropane diamine, ethoxylated (5 moles ethylene oxide) stearylamine, dihydroxy ethyl stearylamine, arachidylbehenylamine, and the like. Some suitable betaine surfactants include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates, and acyl glutamates, wherein the alkyl and acyl groups have from 8 to 18 carbon atoms. Non-limiting examples of preferred amphoteric surfactants include cocamidopropyl betaine, sodium cocoamphoacetate, cocamidopropyl hydroxysultaine, and sodium cocoamphopropionate, which are particularly suitable as mild-type cleansers for skin and hair.

A pH adjusting agent can be added either to a previously acid-swollen, or water-swollen cationic associative polymer or to a formulation containing a cationic associate polymer. Thus, the pH adjusting agent can be utilized in any amount necessary to obtain a desired pH value in the final composition. Non-limiting examples of alkaline pH adjusting agents include alkali metal hydroxides, such as sodium hydroxide, and potassium hydroxide; ammonium hydroxide; organic bases, such as triethanolamine, diisopropylamine, dodecylamine, diisopropanolamine, aminomethyl propanol, cocamine, oleamine, morpholine, triamylamine, triethylamine, tromethamine (2-amino-2-hydroxymethyl)-1, 3-propanediol), and tetrakis(hydroxypropyl)ethylenediamine; and alkali metal salts of inorganic acids, such as sodium borate (borax), sodium phosphate, sodium pyrophosphate, and the like, and mixtures thereof. Acidic pH adjusting agents can be organic acids, including amino acids, and inorganic mineral acids. Non-limiting examples of acidic pH adjusting agents include acetic acid, citric acid, fumaric acid, glutamic acid, glycolic acid, hydrochloric acid, lactic acid, nitric acid, phosphoric acid, sodium bisulfate, sulfuric acid, tartaric acid, and the like, and mixtures thereof.

The polymers of the present invention can be used as a thickener, film former, or as a dye or pigment suspending agent for promoting deposition of colorants on hair and skin. Colorants for hair can be temporary, semipermanent or permanent hair dyes or color restorers that pigment the hair gradually. Temporary and semipermanent hair dyes typically are rinses, gels, sprays, shampoos, sticks, and the like, and hair color restorers are typically in the form of hair dressings or emulsions. Permanent hair dyes, and longer-lasting semipermanent hair dyes, are generally two-part products, one part containing the oxidative dye intermediates and dye couplers, and the other part containing stabilized oxidizing agent, usually hydrogen peroxide at about pH 3-4, and are mixed together immediately before use. It is known that such two-part hair dyeing products are formulated with combinations of surfactant ingredients, usually nonionic surfactants or anionic surfactants, to thicken when the dye mixture is prepared. In addition to the foregoing literature, a general discussion of hair dyeing chemistry and compositions is in Brown et al, *SCC Monograph*, "Permanent Hair Dyes", Society of Cosmetic Chemists (1996), incorporated herein by reference. The polymers of the present invention may be incorporated in one or both of the two-parts of such hair dyeing systems, either as the thickener for the acidic stabilized oxidizing portion or in the non-oxidizing portion to be thickened upon mixing with the acidic portion.

In addition to ingredients discussed above, other ingredients commonly used for antiacne products, facial and body hair bleaches, and antiseptic products include oxidizing agents, such as hydrogen peroxide, benzoyl peroxide, and water-soluble inorganic persulfate compounds such as ammonium persulfate, potassium persulfate, and sodium persulfate.

The polymers of the present invention are particularly useful as emulsification aids for water-insoluble (hydrophobic) oily materials such as natural and synthetic oils, fats, and waxes, including, for example, vegetable oils, animal oils and fats, paraffin oils and waxes, silicone oils and waxes; and the like. Many oily materials are used as solvents, carriers, emollients, or conditioning agents, for example, in hair and skin care products.

The polymers of the present invention are surprisingly useful stabilizers of silicone fluids, which are commonly used in shampoo products, such as the so-called "two-in-one" combination cleansing/conditioning shampoos. Silicone fluids are generally described as alkylsiloxane polymers. The most common class of silicone polymers are the linear polydimethyl siloxanes having the general formula $CH_3$—$(Si(CH_3)_2$—$O)_w$—$Si(CH_3)_3$ where w denotes an integer greater than 2. Silicones can also be branched materials wherein one or more alkyl groups in a polymer are replaced with an oxygen to create a branch point. Silicone fluids are typically water-insoluble oils having a viscosity in the range of a few mPa·s to several hundred thousand mPa·s.

A particularly useful class of silicones for use in hair care products are the so-called rigid silicones (also known as silicone gums), as described, for example in U.S. Pat. No. 4,902,499, incorporated herein by reference, which generally have a viscosity (at about 20° C.) of greater than about 600,000 mPa·s and have a weight average molecular weight of at least about 500,000 Daltons as determined by intrinsic viscosity measurement. The polymers of the present invention are surprisingly effective for stabilizing two-in-one type shampoo formulations containing rigid silicone conditioning agents.

Another class of silicone materials that are particularly useful in combination with the polymers of the present invention are the volatile silicones, which are often used as lubricants in hair care products, such as shampoos. Volatile silicones include cyclic and linear polydimethylsiloxanes, and the like. Cyclic volatile silicones typically contain about 3 to about 7 silicon atoms, alternating with oxygen atoms, in a cyclic ring structure. Each silicon atom is also substituted with two alkyl groups, typically methyl groups. Linear volatile silicones are silicone fluids, as described above, having viscosities of not more than about 25 mPa·s. A description of volatile silicones is found in Todd and Byers, "Volatile Silicone Fluids for Cosmetics", *Cosmetics and Toiletries*, Vol. 91(1), pp. 27-32 (1976), and in Kasprzak, "Volatile Silicones", *Soap/Cosmetics/Chemical Specialities*, pp. 40-43 (December 1986), each incorporated herein by reference.

Other silicone oils include the dimethicone copolyols, which are linear or branched copolymers of dimethylsiloxane (dimethicone) and alkylene oxides. The dimethicone polyols can be random or block copolymers. A generally useful class of dimethicone polyols are block copolymers having blocks of polydimethylsiloxane and blocks of polyalkylene oxide, such as blocks of polyethylene oxide, polypropylene oxide, or both. Silicone fluids, including volatile silicones, silicone gums, and silicone copolymers, are available from a variety of commercial sources such as Dow Corning, General Electric Company, and Noveon, Inc.

Other oily materials that are useful in combination with the polymers of the present invention include, for example, acetylated lanolin alcohols; lanolin alcohol concentrates; esters of lanolin fatty acids such as the isopropyl esters of lanolin fatty acid; polyol fatty acids; ethoxylated alcohols, such as ethoxylate and castor oils; sterols; sterol esters; sterol ethoxylates; and like materials. Many of such esters and ethoxylates are also useful as non-ionic surfactants.

Numerous ingredients are known in the art as conditioning agents for hair or skin, and humectants, and in addition to those previously discussed, non-limiting examples include PCA (DL-pyrrolidone carboxylic acid) and its salts, such as lysine PCA, aluminum PCA, copper PCA, chitosan PCA, and the like, allantoin; urea; hyaluronic acid and its salts; ceramides; sorbic acid and its salts; sugars and starches and derivatives thereof; lactamide MEA; and the like.

The following examples further illustrate the preparation and use of preferred embodiments but are not intended to be limiting.

Materials and Procedures

The materials are generally commercially available from chemical supply houses known to those skilled in the chemical arts or from the supplier indicated.

| 1. Materials Abbreviations and Trade Names | |
|---|---|
| EA | Ethyl acrylate |
| DMAEMA | 2-(N,N-dimethylamino)ethyl methacrylate |
| DEAEMA | 2-(N,N-diethylamino)ethyl methacrylate |
| TBAEMA | 2-(tert-butylamino)ethyl methacrylate |
| DMAPMAm | 2-(N,N-dimethylamino)propyl methacrylamide |
| DMANPA | 2-(N,N-dimethylamino)neopentyl acrylate |
| TMCHMA | 3,3,5-Trimethylcyclohexyl methacrylate |
| MMA | Methylmethacrylate |
| BEM25 | Beheneth-25 methacrylate |
| CCEM25 | Approximately 1:1 mixture of Choleth-25 methacrylate and Ceteth-25 methacrylate |
| LEM23 | Laureth-23 methacrylate |
| TEM25 | Tristyrylphenol ethoxylated (25) methacrylate |
| CSEM25 | Ceteareth-25 methacrylate |
| HEMA | 2-Hydroxyethyl methacrylate |
| EOBDMA | Ethoxylated (30) bisphenol A dimethacrylate |
| TEGDMA | Triethyleneglycol dimethacrylate |
| R307 | A randomly ethoxylated/propoxylated 1,4-butanediol vinyl ether having the empirical formula $CH_2$=CH—$O(CH_2)_4O(C_3H_6O)_4(C_2H_4O)_{30}H$ (EMULSOGEN ® R307, Clariant Corporation) |
| RAL307 | A randomly ethoxylated/propoxylated allyl ether having the empirical formula $CH_2$=$CHCH_2O(C_3H_6O)_4(C_2H_4O)_{30}H$; (EMULSOGEN ® RAL307, Clariant Corporation) |
| R208 | A randomly ethoxylated/propoxylated 1,4-butanediol vinyl ether having the empirical formula $CH_2$=CH—$O(CH_2)_4O(C_3H_6O)_4(C_2H_4O)_{20}H$ (EMULSOGEN ® R208, Clariant Corporation) |
| C897 | Ethoxylated octylphenol, INCI name octoxynol-40, reportedly having an HLB of 18 (IGEPAL ® CA-897, Rhodia, Inc.) |
| P-38 | Ethoxylated (27) cetearyl alcohol, INCI name Ceteareth-27, reportedly having an HLB of 19 (PLURAFAC ® A-38, BASF Corp.) |
| P-39 | Ethoxylated (55) cetearyl alcohol, INCI name Ceteareth-55, reportedly having an HLB of 24 (PLURAFAC ® A-39, BASF Corp.) |
| E407 | Secondary $C_{11}$ ethoxylate having 40 ethylene oxide units per alcohol unit (EMULSOGEN ® EPN 407, Clariant Corp.) |
| F127 | Block copolymer of ethylene oxide and propylene oxide reportedly having an HLB of 22 and the formula: $HO(C_2H_4O)_{98}(C_3H_6)_{67}(C_2H_4O)_{98}H$, (PLURONIC ® F127, BASF Corp.) |
| L-35 | Block copolymer of ethylene oxide and propylene oxide reportedly having an HLB of 19 and the formula: $HO(C_2H_4O)_{11}(C_3H_6)_{16}(C_2H_4O)_{11}H$, (PLURONIC ® L35, BASF Corp.) |
| X1005 | Ethoxylated (100) Isotridecyl alcohol (GENAPOL ® X 1005, Clariant Corp.) |
| A5060 | Ethoxylated (50) linear fatty alcohols (DISPONIL ® A 5060; Cognis) |
| AMHEC | Allyl modified hydroxyethyl cellulose powder (<180 μm) (TYLOSE ® AM H40 YP2; Clariant Corp.) |

2. Methods.

A. Viscosity. The reported viscosity of each polymer containing composition was measured in milli-Pascal seconds (mPa·s), employing a Brookfield rotating spindle viscometer, (Brookfield, Model RVT) at 20 revolutions per minute (rpm), at ambient room temperature of about 20 to about 25° C. (referred to as Brookfield viscosity).

A "thin or low viscosity" typically refers to a pourable, runny product having a viscosity of up to about 1,000 mPa·s; a "medium viscosity" refers to a product having a viscosity in the range of above 1,000 to about 3,000 mPa·s; a "high viscosity" refers to a product having a viscosity in the range of above 3,000 to about 10,000 mPa·s; and "gel" refers to a product having a viscosity greater than 10,000 mPa·s, unless otherwise indicated.

B. Clarity. When reported, the clarity of the polymer-containing composition was measured in % T (transmittance) by Brinkmann PC 920 colorimeter at least about 24 hours after the composition was made. Clarity measurements were taken against deionized water (clarity rating of 100%). Compositions having a clarity of about 60% or more were substantially clear; compositions having a clarity in the range of about 45-59% were judged substantially translucent.

C. Turbidity. When reported, the turbidity of a polymer-containing composition was determined in Nephelometric Turbidity Units (NTU) employing a Nephelometric turbidity meter with distilled water (NTU=0) as the standard. Compositions having an NTU value of about 90 or greater were judged turbid.

D. Particle Size. The particle size of the polymer emulsion was measured in nanometers (nm) employing a NICOMP® 370 Autodilution submicron particle size analyzer (Particle Sizing Systems, Santa Barbara, Calif.) following the manufacturer's recommended procedures and the data was recorded for 50% volume.

E. Stability. The stability of the polymer product emulsion or formulated composition was evaluated by one or more of the following procedures.

1. Freeze/Thaw Cycle. A sample of about 20 grams of the test product was subjected to at least one freeze/thaw (F/T) cycle by freezing the sample at a temperature of about −12° C. for about 16 hours and then thawing it at a temperature of about 26° C. for about 8 hours. The sample was then visually evaluated for phase separation. If an emulsion displayed creaming, or an increase in viscosity that negatively affected flow, it failed the F/T test. Products remaining substantially unchanged through five F/T cycles were judged very stable.

2. Shelf Storage. A sample of test product was stored at one or more of the following temperatures: a) at ambient room temperature in the range of about 20 to about 25° C. for a period of at least one week and up to about six months; b) at elevated temperature in an oven at a selected temperature in the range of about 5 to about 45° C. (unless otherwise indicated) for a period of up to about 5 weeks (accelerated aging storage).

Stability was determined by periodically visually observing the stored sample for visible sedimentation or a noticeable increase in measurable Brookfield viscosity determined at a selected interval as indicated in the following examples. At ambient temperature storage, the sample was visually checked daily for one week, then biweekly during a total storage period of about two months and monthly thereafter during a total storage period of up to about six months. Under either storage temperature, compositions were judged stable, a) if no sedimentation was observed, or if some sedimentation occurred, it was not more than about 2% of the total volume of the sample, and b) if the viscosity did not increase, or if an increase occurred, the increase was not more than about 1,000 mPa·s E. High Humidity Curl Retention (HHCR). The hair setting efficacy of a polymer was measured by its ability to hold a curl set on hair after absorption of water from the applied composition and from the surrounding atmosphere at high humidity (about 90% Relative Humidity (RH)) employing the well known technique commonly referred to as high humidity curl retention (HHCR). Descriptions of the HHCR methodology are readily found in the cosmetic literature. See, for example, Ch. 30, *Harry's Cosmeticology*, 8th Ed., M. J. Rieger, Ph.D. (ed.), 666-667, Chemical Publishing Co., Inc., New York, N.Y. (2000), and Diaz et al., *J. Soc. Cosmet. Chem.*, 34, 205-212 (July 1983), the relevant disclosures of each are incorporated herein by reference.

Tresses of commercially blended Caucasian untreated (virgin) human hair were prepared employing natural brown or black color European hair supplied by International Hair Importers and Products Inc., New York. Each hair tress (about 3 grams weight) was about 7 inches (about 18 cm) in length and was anchored with glue at the scalp (root) end portion. Prior to use, each hair tress was pre-cleaned by washing with a dilute aqueous solution of sodium lauryl sulfate (10% SLS), followed by thorough rinsing with deionized water at ambient room temperature and dried with towel blotting. The initial extended length of the hair ($L_e$) was measured. About 0.8 grams of polymer-containing composition to be evaluated was applied to the hair tress and distributed uniformly from the scalp to end portion. The treated hair tress was then wrapped around a hair curler having an outer diameter of about 3 cm, and dried on the curler overnight at an ambient room temperature of about 21 to about 23° C. After drying, the curler was carefully removed, leaving the hair styled into a single curl, the initial length of the hair curl ($L_i$) was measured, and the curled hair tress was vertically hung in a humidity chamber set at an ambient temperature of about 26 to about 27° C. and ambient high humidity of about 90% RH.

The percent curl retention (HHCR) was determined by measuring the length of the hair curl as the curl relaxed after selected intervals ($L_t$) of exposure to humidity. The following equation was used to calculate percent curl retention, relative to the initial curl length ($L_i$) and length of the fully extended hair, before curling ($L_e$).

$$\% \text{ Curl Retention} = \frac{L_e - L_t}{L_e - L_i} \times 100$$

The change in curl length (droop, helix formation) was periodically measured and monitored over a period in the range of about 4 to about 24 hours with a final reading being taken after about 24 hours. A retention of about 70% or more curl (HHCR) for a minimum period of about 0.75 hours at about 90% RH is a conventional benchmark for good high humidity resistance. Hair setting efficacy (i.e., HHCR) of about 70% for at least 1.25 hours to about 3 hours was judged very good, and an HHCR greater than about 70% after a period of at least about 3 hours or longer was judged excellent. A HHCR of not more than 50% was judged weak.

EXAMPLE 1

Polymers

The cationic acid-swellable associative polymer identified as Polymer A in Table 2 was prepared according to the general procedure described above, and as described in detail below.

A monomer emulsion was prepared by adding with mixing agitation about 56 parts by weight of ethyl acrylate, about 37 parts by weight of DMAEMA, about two parts by weight of HEMA, about three parts by weight of BEM25, about two parts by weight of R208 and about 0.15 parts by weight of TEGDMA into a reactor containing about 350 parts by weight of water containing about seven parts by weight C897 nonionic surfactant and about 0.3 parts by weight of sodium lauryl sulfate (30%) anionic surfactant. The resulting mixture was agitated (about 200 rpm) at a temperature in the range of about 30 to about 40° C. under a nitrogen atmosphere until an emulsion was obtained. A solution of about 0.15 parts by weight of sodium persulfate in about three parts by weight of water was then added to the monomer emulsion, with mixing agitation, to initiate the polymerization reaction. The temperature of the reaction mixture was maintained at a temperature in the range of about 60 to about 62° C. for about 2.5 hours after addition of the initiator. Additional quantities of initiator were added at about 0.5 hours and about 1.5 hours after the reaction was initiated (about 0.02 parts by weight of sodium persulfate in about 3.5 parts by weight of water for each additional quantity of initiator added).

The resulting polymer emulsion was cooled to a temperature in the range of about 44 to about 46° C. over a period of about 45 minutes and an oxidizing solution was added to the reaction mixture in two portions at one hour intervals thereafter. Each oxidizing (redox) solution contained about 0.15 parts by weight of t-butylhydroperoxide (70%), about 0.015 parts by weight of sodium lauryl sulfate (30%) and about 0.15 parts by weight of sodium metabisulfite in about nine parts by weight of water.

The polymer emulsion was then cooled to ambient room temperature and discharged from the reactor, bottled, and stored under an inert atmosphere at ambient room temperature. The resulting polymer emulsion, Polymer A, had a total polymer solids of about 21% by weight, a pH of about 8.3, and a viscosity of about 32 mPa·s. The concentration of residual ethyl acrylate monomer was less than about 1.2 ppm and of residual DMAEMA was less than about 9 ppm.

Comparative Polymers CP-1, CP-2, CP-3, CP-4 and CP-5 each having the monomer components and surfactants shown in Table 1, and inventive cationic associative polymers, Polymers B-Y and AA-AT each having the monomer components and surfactants as shown in Tables 2 and 2A, were prepared following the general method for the preparation of Polymer A, above. The amount of each monomer type and surfactant was adjusted, as needed, to achieve the monomer weight percent and surfactant weight percent values listed in Tables 1, 2, and 2A. All monomer % values in the tables are weight percent based on total monomer mixture weight; whereas all surfactant % values are based on total emulsion weight (i.e., combined weight of all monomers, additives, surfactants, and water). All of the emulsions were prepared at an active polymer concentration in the range of at least about 15 weight percent, up to about 20 weight percent, based on total emulsion weight. The Polymer Emulsions CP-1 and CP-2 in Table 1 and Emulsions B, C, D, E and F in Table 2 also contain about 2.5 weight % of propylene glycol, on a total emulsion weight basis, as an emulsification aid.

In Tables 1, 2, and 2A, ASV=amino-substituted vinyl; HNV=hydrophobic nonionic vinyl, AV=associative vinyl; and in Tables 2 and 2A, Mon.=monomer; and SVS=semihydrophobic vinyl surfactant.

TABLE 1

Comparative Acidic Polymer Emulsions

| Polymer No. | ASV Monomer (%) | HNV Monomer (%) | AV Monomer (%) | Other Monomer (%) | Nonionic Surfactant (%) |
|---|---|---|---|---|---|
| CP-1 | DMAEMA (37) | EA (57.7) | BEM25 (5) | EOBDMA (0.3) | C897 (7) |
| CP-2 | DMAEMA (37) | EA (60) | BEM25 (3) | — | C897 (7) |
| CP-3 | DMAEMA (35) | EA (61.9) | BEM25 (3) | TEGDMA (0.1) | P-38 (6.9) |
| CP-4 | DMAEMA (35) | EA (61.9) | BEM25 (3) | TEGDMA (0.1) | P-39 (6.9) |
| CP-5 | DMAEMA (35) | EA (61.9) | BEM25 (3) | TEGDMA (0.1) | F127 (1, 4); L-35 (5.6) |

TABLE 2

Cationic Associative Polymer Emulsions

| Pol. No. | ASV Mon. (%) | HNV Mon. (%) | AV Mon. (%) | SVS Mon. (%) | Other Mon. (%) | Surfactant (%) |
|---|---|---|---|---|---|---|
| A | DMAEMA (37) | EA (55.85) | BEM25 (3) | R208 (2) | TEGDMA (0.15); HEMA (2) | C897 (7) |
| B | DMAEMA (37) | EA (55.85) | BEM25 (3) | R307 (2) | TEGDMA (0.15); HEMA (2) | C897 (7) |
| C | DMAEMA (37) | EA (52.85) | BEM25 (3) | R307 (5) | TEGDMA (0.15); HEMA (2) | C897 (7) |
| D | DMAEMA (31) | EA (61.85) | BEM25 (3) | R307 (2) | TEGDMA (0.15); HEMA (2) | C897 (7) |
| E | DMAEMA (34) | EA (58.85) | BEM25 (3) | R307 (2) | TEGDMA (0.15); HEMA (2) | C897 (7) |
| F | DMAEMA (40) | EA (52.85) | BEM25 (3) | R307 (2) | TEGDMA (0.15); HEMA (2) | C897 (7) |
| G | DMAEMA (34) | EA (56.85) | BEM25 (3) | R307 (6) | TEGDMA (0.15) | C897 (5.5) |
| H | DMAEMA (34) | EA (55.85) | BEM25 (3) | R307 (7) | TEGDMA (0.15) | C897 (5) |
| I | DMAEMA (37) | EA (55.85) | BEM25 (3) | R307 (2) | TEGDMA (0.15); HEMA (2) | P-38 (7) |
| J | DMAEMA (31) | EA (60.85) | BEM25 (3) | R208 (3) | TEGDMA (0.15); HEMA (2) | P-38 (6.5) |

TABLE 2-continued

Cationic Associative Polymer Emulsions

| Pol. No. | ASV Mon. (%) | HNV Mon. (%) | AV Mon. (%) | SVS Mon. (%) | Other Mon. (%) | Surfactant (%) |
|---|---|---|---|---|---|---|
| K | DMAEMA (35) | EA (55.9) | BEM25 (3) | R208 (4) | TEGDMA (0.1); HEMA (2) | P-38 (6.5) |
| L | DMAEMA (40) | EA (52.85) | BEM25 (3) | R307 (2) | TEGDMA (0.15); HEMA (2) | P-38 (6.5) |
| M | DMAEMA (35) | EA (57.85) | BEM25 (3) | R307 (2) | TEGDMA (0.15); HEMA (2) | P-38 (5.6); P-39 (1.4) |
| N | DMAEMA (31) | EA (59.85) | BEM25 (3) | R307 (4) | TEGDMA (0.15); HEMA (2) | P-39 (6.5) |
| O | DMAEMA (35) | EA (57.85) | BEM25 (3) | R208 (2) | TEGDMA (0.15); HEMA (2) | P-39 (7) |
| P | DMAEMA (40) | EA (51.9) | BEM25 (3) | R307 (3) | TEGDMA (0.1); HEMA (2) | P-39 (7) |
| Q | DMAEMA (35) | EA (56.9) | BEM25 (3) | R307 (3) | TEGDMA (0.1); HEMA (2) | F127 (1.4); L-35 (5.6) |
| R | DMAEMA (37) | EA (55.85) | BEM25 (3) | R307 (2) | TEGDMA (0.15); HEMA (2) | F127 (7) |
| S | DMAEMA (37) | EA (55.85) | BEM25 (3) | R307 (2) | TEGDMA (0.15); HEMA (2) | F127 (6) |
| T | DMAEMA (37) | EA (55.85) | BEM25 (3) | R307 (2) | TEGDMA (0.15); HEMA (2) | F127 (5) |
| U | DMAEMA (34) | EA (58.85) | BEM25 (3) | R307 (4) | TEGDMA (0.15) | C897 (6.5) |
| V | DMAEMA (34) | EA (57.85) | BEM25 (3) | R307 (5) | TEGDMA (0.15) | C897 (6.5) |
| W | DMAEMA (35) | EA (55.9) | BEM25 (3) | R307 (4) | TEGDMA (0.1) HEMA (2) | P-38 (7) |
| X | DMAEMA (35) | EA (55.9) | BEM25 (3) | RAL307 (4) | TEGDMA (0.1) HEMA (2) | E407 (7) |
| Y | DMAEMA (35) | EA (55.9) | BEM25 (3) | RAL307 (4) | TEGDMA (0.1) HEMA (2) | E407 (5.5) |

TABLE 2A

Cationic Associative Polymer Emulsions

| Pol. No. | ASV Mon. (%) | HNV Mon. (%) | AV Mon. (%) | SVS Mon. (%) | Other Mon. (%) | Surfactant (%) |
|---|---|---|---|---|---|---|
| AA | DMAEMA (30) TBAEMA (5) | EA (55.9) | BEM25 (3) | R307 (4) | TEGDMA (0.1); HEMA (2) | P-38 (7) |
| AB | DMAEMA (25) TBAEMA (10) | EA (55.9) | BEM25 (3) | R307 (4) | TEGDMA (0.1); HEMA (2) | P-38 (7) |
| AC | DMAEMA (30) DMAPMAm (5) | EA (55.9) | BEM25 (3) | RAL307 (4) | TEGDMA (0.1); HEMA (2) | E-407 (5.5) |
| AD | DMAEMA (35) | EA (50.9) TMCHMA (5) | BEM25 (3) | R307 (4) | TEGDMA (0.1); HEMA (2) | P-38 (7) |
| AE | DMAEMA (35) | EA (53.9) TMCHMA (2) | BEM25 (3) | R307 (4) | TEGDMA (0.1); HEMA (2) | P-38 (7) |
| AF | DMAEMA (35) | EA (55.9) | CSEM25 (3) | R307 (4) | TEGDMA (0.1); HEMA (2) | P-38 (7) |
| AG | DMAEMA (35) | EA (56.4) | CSEM25 (1) BEM25 (1.5) | R307 (4) | TEGDMA (0.1); HEMA (2) | P-38 (7) |
| AH | DMAEMA (35) | EA (55.9) | BEM25 (3) | RAL307 (4) | TEGDMA (0.1); HEMA (2) | P-38 (7) |
| AI | DEAEMA (35) | EA (55.9) | BEM25 (3) | RAL307 (4) | TEGDMA (0.1); HEMA (2) | E-407 (5.5) |
| AJ | DMAEMA (35) | EA (55.9) | CSEM25 (3) | R307 (4) | TEGDMA (0.1); HEMA (2) | A5060 (7) |
| AK | DMAEMA (35) | EA (55.9) | CSEM25 (3) | R307 (4) | TEGDMA (0.1); HEMA (2) | X1005 (7) |
| AL | DMAEMA (35) | EA (55.9) | CSEM25 (3) | R307 (4) | TEGDMA (0.1); HEMA (2) | P-38 (7) AMHEC (0.05) |
| AM | DMAEMA (35) | EA (55.9) | CSEM25 (3) | R307 (4) | TEGDMA (0.1); HEMA (2) | P-38 (7) AMHEC (0.1) |
| AN | DMAEMA (35) | EA (55.9) | CCEM25 (3) | R307 (4) | TEGDMA (0.1); HEMA (2) | P-38 (7) |
| AO | DMAEMA (35) | EA (55.9) | LEM23 (3) | R307 (4) | TEGDMA (0.1); HEMA (2) | P-38 (7) |
| AP | DMAEMA (35) | EA (57.4) | TEM25 (1.5) | R307 (4) | TEGDMA (0.1); HEMA (2) | P-38 (7) |

TABLE 2A-continued

Cationic Associative Polymer Emulsions

| Pol. No. | ASV Mon. (%) | HNV Mon. (%) | AV Mon. (%) | SVS Mon. (%) | Other Mon. (%) | Surfactant (%) |
|---|---|---|---|---|---|---|
| AQ | DMAEMA (35) | EA (52.9) TMCHMA (3) | CSEM25 (3) | R307 (4) | TEGDMA (0.1); HEMA (2) | P-38 (7) |
| AR | DMAEMA (35) | EA (52.9) MMA (3) | CSEM25 (3) | R307 (4) | TEGDMA (0.1); HEMA (2) | P-38 (7) |
| AS | DMAEMA (30) DMANPA (5) | EA (55.9) | CSEM25 (3) | R307 (4) | TEGDMA (0.1); HEMA (2) | P-38 (7) |
| AT | DMANPA (35) | EA (55.9) | CSEM25 (3) | R307 (4) | TEGDMA (0.1); HEMA (2) | P-38 (7) |

After the preparation of the polymers, product emulsions were analyzed to determine the pH, percent total solids based on polymer content, Brookfield viscosity (spindle #2, 20 rpm, ambient room temperature) and particle size (nm). The unneutralized product polymer emulsions generally had a pH in the range of about pH 7.5 to about 9; total solids in the range of about 15 to about 25 weight percent; a Brookfield viscosity in the range of about 10 to about 100 mPa·s, and an average particle size in the range of about 80 nm to about 260 nm.

The product emulsions of the cationic associative polymers shown in Table 2, remained stable, based on studies of up to five F/T cycles, and shelf storage at ambient room temperature for at least about 5 months. The viscosity of the foregoing cationic associative polymer emulsions stored for about 5 weeks at a temperature of about 45° C. remained stable, any viscosity increase noted being not more about 100 mPa·s.

In contrast, the emulsion stability of the product emulsions of the comparative cationic polymers (i.e., lacking any SVS monomer) shown in Table 1 was either poor, i.e., less than 2 months at room temperature (CP-1, CP-2 and CP-5) or the product was so congealed that the viscosity was judged unmeasurable (CP-3 and CP-4).

EXAMPLE 2

Cationic Salt Compatibility

This example illustrates the compatibility of all of the cationic associative polymers of Example 1, except for Polymers H, X, and Y of Table 2, with cationic quaternary ammonium salt, cetyl trimethylammonium chloride (INCI name cetrimonium chloride, referred to herein for brevity as CTAC) based on Brookfield viscosity and turbidity (NTU). Aqueous compositions were prepared containing cationic associative polymer, as indicated below, at an active polymer weight concentration of about 2% and CTAC in amounts of about 0.5, 1 and 1.5 weight % (active weight basis). The viscosity and turbidity values, where determined, are shown in the following Tables 3, 3A, 3B and 3C.

TABLE 3

| Polymer | % CTAC | | | Viscosity | Turbidity |
|---|---|---|---|---|---|
| 2% | 0.5 | 1 | 1.5 | mPa·s | NTU |
| A |   |   |   | 25,000 | — |
| A | X |   |   | 26,500 | — |
| A |   | X |   | 16,750 | — |
| A |   |   | X | 10,250 | 4 |

TABLE 3-continued

| Polymer | % CTAC | | | Viscosity | Turbidity |
|---|---|---|---|---|---|
| 2% | 0.5 | 1 | 1.5 | mPa·s | NTU |
| B |   |   |   | 25,600 | — |
| B | X |   |   | 26,800 | — |
| B |   | X |   | 14,420 | — |
| B |   |   | X | 7,680 | — |
| C |   |   |   | 16,700 | — |
| C | X |   |   | 27,150 | — |
| C |   | X |   | 15,650 | — |
| C |   |   | X | 8,100 | — |
| D |   |   |   | 7,600 | — |
| D | X |   |   | 8,160 | 20 |
| D |   | X |   | 4,300 | 10 |
| D |   |   | X | 2,040 | 10 |
| E |   |   |   | 16,580 | — |
| E | X |   |   | 16,460 | 26 |
| E |   | X |   | 9,280 | 25 |
| E |   |   | X | 4,290 | 22 |
| F |   |   |   | 22,230 | — |
| F | X |   |   | 25,200 | 14 |
| F |   | X |   | 12,840 | 12 |
| F |   |   | X | 6,820 | 12 |
| G |   |   |   | 15,500 | — |
| G | X |   |   | 17,250 | — |
| G |   | X |   | 9,100 | — |
| G |   |   | X | 4,900 | — |

TABLE 3A

| Polymer | % CTAC | | | Viscosity | Turbidity |
|---|---|---|---|---|---|
| 2% | 0.5 | 1 | 1.5 | mPa·s | NTU |
| I |   |   |   | 31,350 | 18 |
| I | X |   |   | 24,950 | 29 |
| I |   | X |   | 17,400 | 13 |
| I |   |   | X | 10,200 | 12 |
| J |   |   |   | 12,500 | 14 |
| J | X |   |   | 9,800 | 6 |
| J |   | X |   | 6,100 | 5 |
| J |   |   | X | 2,900 | 6 |
| K |   |   |   | 25,750 | 7 |
| K | X |   |   | 21,000 | 6 |
| K |   | X |   | 13,500 | 4 |
| K |   |   | X | 7,100 | 4 |
| L |   |   |   | 21,250 | 17 |
| L | X |   |   | 22,750 | 13 |
| L |   | X |   | 12,800 | 10 |
| L |   |   | X | 6,500 | 10 |
| M |   |   |   | 25,500 | 29 |
| M | X |   |   | 21,500 | 10 |
| M |   | X |   | 10,750 | 10 |
| M |   |   | X | 5,000 | 9 |
| N |   |   |   | 12,900 | 17 |
| N | X |   |   | 11,100 | 6 |

TABLE 3A-continued

| Polymer | % CTAC | | | Viscosity | Turbidity |
|---|---|---|---|---|---|
| 2% | 0.5 | 1 | 1.5 | mPa·s | NTU |
| N | | X | | 4,800 | 7 |
| N | | | X | 1,950 | 5 |
| O | | | | 21,250 | 14 |
| O | X | | | 21,000 | 11 |
| O | | X | | 11,000 | 8 |
| O | | | X | 4,800 | 8 |

TABLE 3B

| Polymer | % CTAC | | | Viscosity | Turbidity |
|---|---|---|---|---|---|
| 2% | 0.5 | 1 | 1.5 | mPa·s | NTU |
| P | | | | 30,250 | 36 |
| P | X | | | 27,250 | 14 |
| P | | X | | 18,250 | 13 |
| P | | | X | 10,100 | 12 |
| Q | | | | 12,100 | 47 |
| Q | X | | | 9,000 | 13 |
| Q | | X | | 5,900 | 7 |
| Q | | | X | 2,850 | 7 |
| R | | | | 8,680 | 18 |
| R | X | | | 13,220 | 10 |
| R | | X | | 11,400 | 7 |
| R | | | X | 7,800 | 7 |
| S | | | | 17,400 | 18 |
| S | X | | | 23,100 | 12 |
| S | | X | | 15,850 | 10 |
| S | | | X | 9,020 | 9 |
| T | | | | 17,860 | 19 |
| T | X | | | 20,900 | 13 |
| T | | X | | 16,050 | 12 |
| T | | | X | 9,240 | 11 |
| U | | | | 18,850 | — |
| U | X | | | 17,500 | — |
| U | | X | | 9,800 | — |
| U | | | X | 5,500 | 8 |
| V | | | | 18,250 | — |
| V | X | | | 17,000 | — |
| V | | X | | 8,000 | — |
| V | | | X | 5,100 | 4 |

TABLE 3C

| Polymer | % CTAC | | | Viscosity | Turbidity |
|---|---|---|---|---|---|
| 2% | 0.5 | 1 | 1.5 | mPa·s | NTU |
| W | | | | 28,750 | — |
| W | X | | | 24,500 | — |
| W | | X | | 13,350 | — |
| W | | | X | 7,300 | — |

All of the aqueous cationic associative polymer compositions were smooth-textured and flowable. In contrast, aqueous compositions prepared employing CP-1 shown in Table 1, Example 1, at a 2% active polymer weight concentration, had a Brookfield viscosity of about 50,400 mPa·s without CTAC, of about 57,400 mPa·s with 0.6% CTAC, about 28,050 mPa·s with 1.2% CTAC and about 28,300 mPa·s with 1.5% CTAC and had a congealed, grainy texture. Likewise, the compositions containing CP-2 were also congealed and grainy.

Based on evaluations with Polymers I, J, K, L, M, N, O, P, Q, R, S and T, the Brookfield viscosity of the compositions containing 1.5% CTAC remained substantially unchanged over a period of about 24 hours at ambient temperature.

EXAMPLE 2A

This example illustrates the utility of the cationic associative polymers to provide substantively clear aqueous compositions of varying viscosity by appropriate selection of monomers and surfactants.

As shown in Table 3, Example 2, at a 2% active polymer weight in water, the cationic associative polymers, Polymers A-C, E-Q and S—W produced gels having a Brookfield viscosity in the range of about 12,100 mPa·s to about 31,350 mPa·s and Polymers D and R provided high Brookfield viscosities of about 7,600 mPa·s and 8,680 mPa·s, respectively.

At a 2% active polymer weight in water, Polymers H, X, and Y, shown in Table 2, Example 1, respectively, provided a high Brookfield viscosity of about 6,400 mPa·s, and gels of about 31,800 mPa·s, and 18,900 mPa·s.

Likewise, at a 2% active polymer weight in water, Polymers AA-AH, AJ-AN, and AP-AR, listed in Table 2A, Example 1, provided substantially clear gels having a Brookfield viscosity in the range of about 10,300 mPa·s to about 30,700 mPa·s. A 2% active polymer weight in water of Polymers AI and AO, listed in Table 2A, Example 1, respectively, provided a medium Brookfield viscosity in the range of about 2,530 mPa·s to about 8,800 mPa s. Polymer emulsions containing a polymeric stabilizer (e.g., AMHEC), Polymers AL and AM, listed in Table 2A produced smooth gels with good slip characteristics.

The NTU values for the aqueous cationic associative polymers, Polymers AD-AG, were in the range of about 12 to about 31. The clarity of the aqueous cationic associative polymers, Polymers Y, AA-AC, and AH-AR, was in the range of about 70% (Polymer AH) to about 93% T (Polymer Y).

Substantially clear gels having a higher viscosity were obtained by increasing the amount of cationic associative polymer. For example, at a 3% active polymer weight of Polymer AQ, or Polymer AR, the viscosity increased, respectively, to about 44,400 mPa·s, and 61,500 mPa·s, and clarity was substantially unchanged (% T was in the range of about 85 to about 88%). The viscosity of Polymer AR, at 3% active polymer weight, decreased to about 42,500 mPa·s by including about 10% ethanol, with no loss in clarity (% T was about 89).

EXAMPLE 3

This example illustrates the compatibility of cationic associative polymer, Polymer A of Example 1, with various cationic quaternary ammonium salts at various active weight percent concentrations of each, in aqueous solution as shown in Table 4. Compatibility was determined based on Brookfield viscosity and clarity (% T), as described in Methods A and B, respectively. All compositions shown in Table 4 were readily spreadable and flowable with an aesthetically pleasing, smooth texture, free of lumps or graininess.

TABLE 4

| Cationic Salt INCI/Trade Name | % Cationic Salt | % Polymer A | Viscosity mPa·s | Clarity % T |
|---|---|---|---|---|
| None | — | 2 | 25,000 | 79 |
| Olealkonium chloride (Note 1) | 1 | 2 | 11,000 | 97 |

TABLE 4-continued

| Cationic Salt INCI/Trade Name | % Cationic Salt | % Polymer A | Viscosity mPa · s | Clarity % T |
|---|---|---|---|---|
| VARISOFT® Clear (Note 2) | 1 | 2 | 7,300 | 88 |
| Polyquaternium-4 (Note 3) | 1 | 2 | 15,300 | 87 |
| JAGUAR® C-145 (Note 4) | 1 | 1.5 | 22,600 | — |
| Distearyldimonium chloride (Note 5) | 2.5 | 0.75 | 8,100 | — |
| Distearyldimonium chloride | 2.5 | 1.5 | 41,200 | — |
| Dicetyldimonium chloride (Note 6) | 2.5 | 1.5 | 32,000 | — |

Note 1. INCI name for oleyldimethylbenzyl ammonium chloride
Note 2. Trade name for a mixture having the INCI name, Palmitamidopropyl trimonium chloride; and PPG-3 myristylether and trimethylpentanolhydroxyethyl ether sold by Degussa Care Specialties.
Note 3. INCI name for Copolymer of hydroxyethyl cellulose and diallyldimethyl ammonium chloride, such as CELQUAT® H-100, sold by National Starch.
Note 4. Trade name of Rhône-Poulenc for INCI name compound, Guar hydroxypropyl trimonium chloride.
Note 5. INCI name for distearyldimethyl ammonium chloride.
Note 6. INCI name for dicetyldimethyl ammonium chloride.

EXAMPLE 4

Acidic Skin Care Emulsion

This example illustrates the use of about 0.5 to about 0.6 active weight % cationic associative Polymer A of Example 1 in an acidic skin care emulsion containing about 5% alpha-hydroxy acid (lactic acid) in the formulation shown in Table 5.

TABLE 5

| Ingredient INCI/Trade Name | Wt % |
|---|---|
| 1. Water, deionized, to 100% | q.s. |
| 2. Mineral Oil, USP | 15 |
| 3. Glyceryl stearate, acid stable, self-emulsifying (Note 7) | 3.5 |
| 4. Cetyl alcohol | 2.5 |
| 5. Dow Corning 1401 fluid (Note 8) | 1 |
| 6. Metal ion chelating agent | 0.05 |
| 7. Propylene glycol | 4 |
| 8. Polymer A, Ex. 1 (active %) | 0.5-0.6 |
| 9. Lactic acid (85%) | 6 |
| 10. Fragrance | q.s. |
| 11. NH$_4$OH (30%) to about pH 3-3.5 | q.s. | q.s. = quantity sufficient to meet the requirement
Note 7. Preferably INCI compounds, Glyceryl Stearate (and) PEG-100 Stearate, such as ARLACEL® 165 sold by Uniqema.
Note 8. Trade name of Dow Corning Corp. for INCI name mixture Cyclomethicone (and) Dimethiconol.

The formulation was prepared at a temperature in the range of about 55 to about 65° C. by separately preparing at elevated temperatures an oil phase containing ingredients no. 2, 3, 4 and 5 and a water phase containing ingredients no. 1, 6, 7, 8 and 9, and then adding the oil phase to the water phase, mixing until a homogenous emulsion formed. The emulsion was then cooled to about 30° C., perfumed with ingredient no. 10 and the final pH was adjusted with ingredient no. 11.

Before adjusting the pH with ingredient no. 11, the emulsion had a pH of about 2. The completed emulsion had a pH of about 3.3 and a Brookfield viscosity of about 11,420 mPa·s (24-hour viscosity). The emulsion was a very smooth, glossy lotion.

The viscosity of the lotion can be increased to a viscous cream by increasing the amount of cationic associative polymer as needed. The composition was judged suitable for use as an acidic skin care product of the type employing alpha-hydroxy acid (AHA), beta-hydroxy acid (BHA), and the like.

EXAMPLE 5

Fabric Softener

This example illustrates the cationic salt compatibility of cationic associative polymers of Example 1, Polymer A (Ex. 5A) and Polymer I (Ex. 5B, 5C), employed as thickeners in an esterquat-containing fabric softener composition having the formula shown in Table 6.

TABLE 6

| Ingredient | Wt % |
|---|---|
| Polymer indicated in Table 6A | 0.25-0.35 (active) |
| Water, deionized, to 100% | q.s. |
| Glycolic acid (50%) to about pH 3 | q.s. |
| DEHYQUART® AU35 (35%) (Note 9) | 5 |

Note 9. Trade name for the esterquat, Methyltriethanolammonium methyl sulfate dialkyl ester, sold by Cognis Corp.

The composition was prepared by neutralizing the polymer in water, with glycolic acid to provide a gel having a pH of about 4, then the esterquat component was added to the gel and mixed until homogeneous. The pH of the homogeneous mixture was then adjusted to about pH 3 with glycolic acid.

The viscosity of the composition was determined initially and after 24 hours and the stability was determined by measuring the viscosity after shelf storage for about 12 weeks at a temperature of about 5° C. and after about four weeks at a temperature of about 50° C. The results are shown in Table 6A.

TABLE 6A

| | Ex. 5A | Ex. 5B | Ex. 5C |
|---|---|---|---|
| Polymer of Example 1 | A | I | I |
| Active Weight % | 0.25 | 0.25 | 0.35 |
| Appearance | Smooth | Smooth | Smooth |
| Brookfield viscosity, mPa · s | | | |
| Immediate | 338 | 245 | 395 |
| 24 Hours | 435 | 365 | 760 |
| 12 Weeks @ 5° C. | — | 390 | 690 |
| 4 Weeks @ 50° C. | — | 1,320 | 4,550 |

For comparison, the composition was again prepared, except that the cationic associative polymer was replaced by about 0.2% and about 0.4% of an acid-swellable, commercial rheology modifier reportedly having a nonionic/cationic charge, sold under the trade name STRUCTURE® Plus by National Starch & Chemical. According to the manufacturer, the INCI name for this material is Acrylates/Aminoacrylates/C$_{10-30}$ Alkyl PEG-20 Itaconate Copolymer and is supplied as a liquid emulsion having about 21% solids and a pH of about 8 to about 9. At the active weight % concentration of about 0.2% and 0.4% STRUCTURE® Plus, the formulations had an immediate Brookfield viscosity, respectively, of about 140 mPa·s and about 250 mPa·s, and each of them had a grainy texture and non-uniform flow characteristic.

EXAMPLE 6

Hair Conditioning Hair Setting Compositions

This example illustrates the uses of cationic associative Polymer A of Example 1 as a thickener in two acidic aqueous gels (Ex. 6A, Ex. 6B) containing the hair fixative, polyvinylpyrrolidone (PVP), suitable for conditioning, fixing and styling hair. The compositions are shown in Table 7, along with Brookfield viscosity and % clarity.

TABLE 7

| Ingredients INCI/Trade Name | Ex. 6A Active Weight % | Ex. 6B Active Weight % |
|---|---|---|
| Water, deionized, to 100% | q.s | q.s. |
| Polymer A, Ex. 1 | 2 | 2 |
| PVP | 3 | 3 |
| CTAC | 1 | |
| Polyquaternium-11 (Note 10) | — | 0.5 |
| Preservative | q.s. | q.s. |
| Glycolic acid (50%) | To about pH 4.5 | To about pH 4.3 |
| Appearance | Smooth Buttery Gel | Smooth Buttery Gel |
| Viscosity, mPa · s | 7,500 | 11,800 |
| % Clarity | 84 | 91 |

Note 10. INCI name for quaternized vinyl pyrrolidone/dimethylaminoethyl methacrylate, copolymer, neutralized sold under the trade name, GAFQUAT ® 755N by International Specialty Products.

Each composition was prepared by admixing all of the ingredients, except for the glycolic acid in the water, and then adjusting the pH downward with the glycolic acid. Both of the products were smoothly spreadable and free of any unaesthetic "stringy" character and provided good hair setting efficacy (70% HHCR for about 1 hour).

EXAMPLE 7

Biocidal Compatibility

This example illustrates the compatibility of Polymer A, of Example 1, with cationic biocidal salts in four formulations (Ex. 7A, 7B, 7C and 7D) shown in Table 8 along with the Brookfield viscosity.

TABLE 8

| Ingredient (INCI/Trade Name) | Weight % Active | | | |
|---|---|---|---|---|
| | Ex. 7A | Ex. 7B | Ex. 7C | Ex. 7D |
| Water, deionized, to 100% | q.s. | q.s. | q.s. | q.s. |
| Polymer A, Ex. 1 | 0.75 | 0.75 | 0.75 | 0.75 |
| Didecyldimonium chloride (Note 11) | 0.1 | 0.3 | — | — |
| Benzalkonium chloride (Note 12) | — | — | 0.1 | 0.3 |
| Glycolic acid (50%) to pH 4-4.5 | q.s. | q.s. | q.s. | q.s. |
| Brookfield viscosity, m Pa · s | | | | |
| Immediate | 306 | 94 | 284 | 93 |
| 24 Hours | — | 174 | — | 137 |

Note 11. INCI name for Didecyldimethyl ammonium chloride, sold under the trade name, BARDAC ® 2250 by Lonza, Inc.
Note 12. INCI name for Alkyldimethyl benzyl ammonium chloride mixture ($C_{14}$, 50%; $C_{12}$, 40%; $C_{16}$ 10%) sold under the trade name, BARQUAT ® MB 50, by Lonza, Inc.

All of the compositions were homogeneous and had smooth flow characteristics.

EXAMPLE 8

Hair Conditioner

This example illustrates the use of Polymer I (Ex. 8A, 8B) and Polymer Q (Ex. 8C) in the hair conditioner formulations and in the active amounts shown in Table 9, along with shelf stability based on storage viscosity.

TABLE 9

| Ingredient (INCI/Trade Name) | Weight % Active | | |
|---|---|---|---|
| | Ex. 8A | Ex. 8B | Ex. 8C |
| 1a. Polymer I, Ex. 1 | 1 | 1 | — |
| 1b. Polymer Q, Ex. 1 | — | — | 1.5 |
| 2. Water, deionized, to 100% | q.s. | q.s. | q.s. |
| 3. Dicetyldimonium chloride | 3.3 | 3.3 | 3.3 |
| 4. Propylene glycol | 0.5 | 0.5 | 0.5 |
| 5. Stearamidopropyldimethyl amine | 0.5 | 0.5 | 0.5 |
| 6. Perfume | q.s. | q.s. | q.s. |
| 7. Cyclomethicone (Note 13) | 2 | — | 2 |
| 8. Panthenol | 0.1 | 0.1 | 0.1 |
| 9. Glycolic acid (50%) to pH 4.5 | q.s. | q.s. | q.s. |
| 10. Preservative | q.s. | q.s. | q.s. |
| Brookfield Viscosity, mPa · s and (pH) | | | |
| Immediate | 5,000 | — | 6,200 |
| 24 Hours | 5,600 (4.4) | 10,000 (4.4) | 7,100 (4.4) |
| 12 Weeks shelf storage @ 45° C. | 2,450 (4.2) | 9,400 (4.7) | 3,375 (4.3) |
| 12 Weeks shelf storage @ Room Temp. | 5,100 (4.1) | 9,700 (4.3) | 7,000 (4.3) |

Note 13. INCI name for cyclic dimethyl polysiloxane compound having an average of 3-6 siloxane units, such as Silicone SF1173 (General Electric).

The compositions were prepared by admixing ingredient nos. 2, 3, 4 and 5 together at a temperature in the range of about 62 to about 63° C. until homogeneous, cooling the admixture to a temperature in the range of about 46 to about 47° C., then admixing in either ingredient no. 1a or 1b, as indicated, ingredients no. 7, when present, no. 8, no. 6 and no. 10 until homogeneous. The pH of the product was then adjusted to about pH 4.5 with ingredient no. 9.

All of the compositions were smooth in texture and flowable.

EXAMPLE 9

Hair Conditioner

This example illustrates the use of Polymer I of Example 1 at two concentrations (Ex. 9A, 9B) in the formulation shown in Table 10, suitable for use as a hair conditioner.

TABLE 10

| Ingredient (INCI/Trade Name) | Weight % Active |
|---|---|
| Phase A | |
| Water, deionized, to 100% | q.s. |
| Polymer I in an amount indicated in Table 10A | 1-1.5 |
| Phase B | |
| Stearalkonium Chloride | 3 |
| Polyquaternium-28 (Note 14) | 1 |
| Panthenol | 1 |
| UV Stabilizer | q.s. |

TABLE 10-continued

| Ingredient (INCI/Trade Name) | Weight % Active |
|---|---|
| Sodium lactate | 0.5 |
| Dow Corning 1401 Fluid (Note 15) | 30 |
| Phase C | |
| Lactic Acid to pH indicated in Table 10A | q.s. |

Note 14. INCI name for quaternary ammonium salt consisting of vinyl pyrrolidone and dimethylaminopropyl methacylamide monomers.
Note 15. Trade name of Dow Corning for INCI mixtures Cyclomethicone (and) Dimethiconol.

The compositions were prepared by premixing the components of Phase A and heating the mixture to a temperature in the range of about 55 to about 60° C. The components of Phase B were added in the order listed, stirring the batch until homogeneous, the batch was then cooled to a temperature of about 30° C., and the pH was adjusted to about 4.5 with Phase C. The final product had a creamy, white appearance, very good flow characteristics and felt silky to the touch. The storage stability of the compositions based on Brookfield viscosity is shown in Table 10A.

TABLE 10A

| | Ex. 9A | Ex. 9B |
|---|---|---|
| Polymer I, Active Wt. % | 1.5 | 1 |
| pH | | |
| Initial | 4.6 | 4.4 |
| 24-Hours | 4.4 | 4.6 |
| Brookfield viscosity, mPa · s | | |
| Initial | 10,580 | 6,300 |
| 24-Hours | 13,540 | 8,040 |
| 8 Weeks @ 5° C. | 17,140 | 8,160 |
| 8 Weeks @ 45° C. | 8,380 | 2,960 |

EXAMPLE 10

Gel

This example illustrates the use of Polymer I of Example 1 in three low-pH aqueous gels (Ex. 10A, 10B, and 10C) in the active polymer weight % amounts shown in Table 11.

TABLE 11

| | Active Weight % | | |
|---|---|---|---|
| Ingredient | Ex. 10A | Ex. 10B | Ex. 10C |
| Polymer I, Ex. 1 | 2 | 2.5 | 3 |
| Deionized, water, to 100% | q.s. | q.s. | q.s. |
| Citric acid (50%) | 25 | 25 | 25 |
| pH | 1.8 | 1.8 | 1.5 |
| Brookfield viscosity, mPa · s | 11,600 | 21,000 | 37,000 |

The gels were judged suitable for use as a general purpose rust and stain removal acid cleaner, such as an acid toilet bowl cleaner, truck cleaner, tank car cleaner, floor cleaner and the like.

The aqueous gels can also be prepared with inorganic mineral acids, such as hydrochloric acid, sulfuric acid or phosphoric acid, instead of citric acid, to produce economical low pH gels suitable for rust removal or industrial applications.

EXAMPLE 11

Clear Bath Gel

This example illustrates the use of Polymer I of Example 1 at an active polymer weight of about 1% in a clear gel composition. The gel composition was prepared at varying pH levels (Gels A, B, and C) employing the formula shown in Table 12.

TABLE 12

| Ingredient (INCI/Trade Name) | Weight % |
|---|---|
| 1. Water, deionized, to 100% | q.s. |
| 2. Polymer I, Ex. 1 (active %) | 1 |
| 3. Sodium laureth-3 sulfate (28%) | 40 |
| 4. Glycolic acid (50%) to about pH 4 | 2.5 |
| 5. Cocamidopropyl betaine (35%) | 14.3 |
| 6. Preservative | q.s. |
| 7. Sodium hydroxide to about pH 5-5.6, as indicated below for Gels B and C | q.s. |

Gel A

Gel A was prepared as follows. Ingredient nos. 1 and 2 were premixed, ingredient no. 3 was added to the premix with gentle mixing and then the mixture was neutralized to about pH 4 with Ingredient No. 4. Ingredient nos. 6 and 7 were then added to the neutralized polymer gel with stir mixing until the gel was homogeneous and clear. Gel A had a pH of about 4.2, a Brookfield viscosity of about 4,280 mPa·s, and was judged stable, based on five freeze/thaw cycles.

Gel B

Gel B was prepared by adjusting the pH of the previously prepared clear Gel A with ingredient no. 7 to about pH 5.2. A sample of Gel B was measured for viscosity, turbidity and stability. Gel B had a Brookfield viscosity of about 3,380 mPa·s, and was judged stable, based on five freeze/thaw cycles.

Gel C

Gel C was prepared by further adjusting the pH of the remaining previously prepared Gel B with ingredient no. 7 to about pH 5.6. Gel C had a Brookfield viscosity of about 3,380 mPa·s, and was judged stable, based on five freeze/thaw cycles.

The turbidity value for each of Gels A, B and C was about 41 NTU. All of the gels were judged suitable for use as clear bath gels.

EXAMPLE 12

Shampoo

The example illustrates the use of Polymer I of Example 1 at an active polymer weight of about 1% in a shampoo composition having the formula shown in Table 13.

TABLE 13

| Ingredient (INCI/Trade Name) | Weight % |
|---|---|
| 1. Water, deionized, to 100% | q.s. |
| 2. Sodium laureth-3 sulfate (28%) | 40 |
| 3. Cocamidopropyl betaine (35%) | 5 |
| 4. Cocamide DEA | 3 |
| 5. Polymer I, Ex. 1 (active %) | 1 |
| 6. Citric acid (50%) to about pH 4-4.6 | q.s. |
| 7. Fragrance | q.s. |

The shampoo was prepared by admixing the ingredients in the order listed, then adjusting the pH, as needed, with ingredient no. 6, and mixing until homogenous. The pH of the completed shampoo was about 4.6. The shampoo had a Brookfield viscosity of about 5,580 mPa s, a turbidity value of about 53 NTU and was judged stable, based on five freeze/thaw cycles. The shampoo was judged suitable for use as an all-purpose type shampoo.

For comparison, a shampoo was similarly prepared without the Polymer I ingredient no. 5. The comparative shampoo had a pH of about 4.5, was nonviscous (Brookfield viscosity of about 115 mPa s), and clear (turbidity value of about 3 NTU).

EXAMPLE 13

Anti-Dandruff Shampoo

This example illustrates the use of cationic associative polymer I of Example 1 at an active polymer weight of about 1% in an anti-dandruff shampoo composition, containing zinc pyrithione as the active dandruff control ingredient, and having the following formula shown in Table 14.

TABLE 14

| Ingredient (INCI/Trade Name) | Weight % |
|---|---|
| 1. Water, deionized, to 100% | q.s. |
| 2. Polymer I, Ex. 1 (active %) | 1 |
| 3. Glycolic acid (50%) to about pH 4-4.5 | q.s. |
| 4. PLANTAREN ® PS-100 (50%) (Note 16) | 25 |
| 5. Cocamide DEA | 3 |
| 6. Cocamidopropyl betaine (35%) | 5 |
| 7. Zinc pyrithione (48%) (Note 17) | 2 |
| 8. Preservative | q.s. |
| 9. Fragrance | q.s. |

Note 16. Trade name of nonionic/anionic surfactant blend of Alkyl Polyglycoside and Ammonium Laureth Sulfate having an alkyl distribution of $C_8$-$C_{16}$ sold by Cognis, Corp.
Note 17. INCI name of compound sold under the trade name Zinc OMADINE ® as a 48% dispersion by Arch Chemicals, Inc.

The shampoo was prepared by admixing the ingredients in the order listed, then adjusting the pH with ingredient no. 3, as needed, and mixing until homogenous.

The pH of the completed shampoo was about 4.5. The shampoo had a Brookfield viscosity of about 9,500 mPa·s and had a smooth, creamy texture and lotion-like appearance. The shampoo remained physically stable on shelf storage at ambient room temperature for a period of at least about five months, and was judged stable, based on five freeze/thaw cycles.

For comparison, a shampoo was similarly prepared without the Polymer I ingredient no. 2. The comparative shampoo had a pH of about 4.5, and was non-viscous (Brookfield viscosity of about 115 mPa·s), and unstable (physically separated within two weeks storage at ambient room temperature).

EXAMPLE 14

Conditioning Shampoo

The example illustrates the use of Polymer W of Example 1 at an active polymer weight of about 1.5% in a conditioning shampoo composition having the formula shown in Table 15.

TABLE 15

| Ingredient (INCI/Trade Name) | Weight % |
|---|---|
| Phase A | |
| 1. Water, deionized, to 100% | q.s. |
| 2. Polymer W, Ex. 1 (active %) | 1.5 |
| 3. Sodium laureth-3 sulfate (28%) | 30 |
| 4. Glycolic acid (50%) to about pH 4.5 | q.s. |
| Phase B | |
| 5. Cocamidopropyl hydroxysultaine (50%) | 10 |
| 6. Disodium laureth sulfosuccinate (40%) (Note 18) | 10 |
| Phase C | |
| 7. Water, deionized, to 100% | 3 |
| 8. Mica and Titanium dioxide (Note 19) | 0.2 |
| Phase D | |
| 9. Dimethicone (60,000 cSt) | 3 |
| 10. Preservative | q.s. |
| 11. Fragrance | q.s. |
| 12. Citric acid (50%) to about pH 4.5 | q.s. |

Note 18. INCI name for the disodium salt of an ethoxylated lauryl alcohol half ester of sulfosuccinic acid, having an average of ethylene oxide units between 1 and 4.
Note 19. Mixture sold under the trade name TIMIRON ® MP-115 Starluster by Rona/Merck KGaA reportedly having 69-75% Mica and 25-31% Titanium dioxide.

The shampoo was prepared as follows. Phase A was prepared by admixing ingredients no. 1 and 2, adding ingredient no. 3 with gentle mixing and then acidifying the mixture to about pH 4.5 with ingredient no. 4. The components of phase B were added to phase A with mixing, in the order indicated. Phase C was separately prepared by premixing ingredients no. 7 and 8, and then adding phase C to the mixture of phases A and B. The remaining ingredients no. 9, 10 and 11 of phase D were added to the batch in the order listed and the pH adjusted to about 4.5 with ingredient 12.

The pH of the completed shampoo was about 4.6. The shampoo had a satiny appearance that was judged more pearlescent than that of a comparison shampoo prepared without Polymer W. The shampoo flowed smoothly, the silicone component remained emulsified during present shelf storage aging of at least one week at ambient room temperature. The shampoo had a Brookfield viscosity of about 7,120 mPa·s, and was judged stable, based on five freeze/thaw cycles. The shampoo was judged suitable for use as a conditioning shampoo of the type commonly referred to as "two-in-one" conditioning shampoo.

For comparison, a shampoo that was similarly prepared without the Polymer W ingredient had a pH of about 4.6, was nonviscous (Brookfield viscosity of less than 100 mPa·s), and unstable (physically separated within 24 hours at ambient room temperature). Similarly, a shampoo formulated with an equivalent amount of polyquaternium-32 (INCI name for SALCARE® SC-92, Ciba Specialty Chemicals) in place of Polymer W was unstable, exhibiting a phase separation. (SALCARE® SC-92 is the trade name for a cationic copolymer liquid dispersion mixture reportedly containing Ethanaminium, N,N,N-trimethyl-2-[(2-methyl-1-oxo-2 propenyl)oxy]-, chloride, polymer with 2-propenamide).

EXAMPLE 15

Cationic Cream Conditioner

This example illustrates the use of Polymer W at an active polymer weight of about 1.6% in a cationic, creamy conditioner formulation shown in Table 16.

TABLE 16

| Ingredient | Wt % as is basis |
|---|---|
| 1. Water, deionized, to 100% | q.s. |
| 2. Glycerin | 3.8 |
| 3. Propylene Glycol | 2 |
| 4. Stearalkonium Chloride (25%) | 2.3 |
| 5. Preservative | q.s. |
| 6. Mineral Oil (light) | 5 |
| 7. Polymer W, Ex. 1 (active weight %) | 1.6 |
| 8. Citric Acid (50%) to pH 3.2-3.8 | q.s. |

The cream formulation was prepared by mixing ingredient nos. 1, 2 and 3 without aeration. Ingredient no. 4 was added to the mixture and admixed thoroughly before adding ingredients nos. 5 and 6. Ingredient no. 7 was then added to the foregoing mixture and mixed thoroughly before adjusting the pH range. The resulting formulation had a white creamy appearance and smooth consistency. The formulation was judged stable, based on freeze/thaw cycles. The initial Brookfield viscosity was about 14,400 mPa·s, and remained substantially unchanged on storage at ambient room temperature and at a temperature of about 45° C. over a period of at least four weeks.

EXAMPLE 16

Cationic Conditioner

This example illustrates the use of Polymer W at an active polymer weight of about 2% in a cationic conditioner formulation shown in Table 17.

TABLE 17

| Ingredient | Wt % as is basis |
|---|---|
| 1. Water, deionized, to 100% | q.s. |
| 2. Glycerin | 3.8 |
| 3. Propylene Glycol | 2 |
| 4. CTAC | 2 |
| 5. Preservative | q.s. |
| 6. Polymer W, Ex. 1 (active weight %) | 2 |
| 7. Citric Acid (50%) to pH 3.5 | q.s. |
| Brookfield visc. mPa · s | 3,770 |
| Clarity (% T) | 83 |

The clear conditioner formulation was prepared by mixing ingredient nos. 1, 2 and 3 without aeration. Ingredient no. 4 was added to the mixture and admixed thoroughly before adding ingredient no. 5. Ingredient no. 6 was then added to the foregoing mixture and mixed thoroughly before adjusting the pH with ingredient no. 7. The resulting formulation was substantially clear and had a smooth consistency.

For comparison, a second conditioner was similarly prepared, except that the commercial cationic polymer, Structure® Plus, described in Example 5, was used in place of Polymer W at the same 2% active polymer weight. This composition had a Brookfield viscosity of about 450 mPa·s, a clarity (% T) of 77, and an undesirable clumpy, grainy consistency.

For further comparison, a third conditioner was similarly prepared, except that a conventional nonionic water-soluble thickener, hydroxyethyl cellulose, (NATROSOL® 250 HHR, CS cosmetic high purity grade, Aqualon/Hercules, Wilmington, Del.), was used at an active weight of 1% instead of Polymer W. The resulting composition had a Brookfield viscosity of about 3,900 mPa·s, a clarity (% T) of about 97, and an unaesthetic, "stringy" consistency.

Polymer W, in the absence of CTAC, was judged to be substantive to hair, based on a modification of the well known "Rubine Dye Test" for cationic sorption, using white yak hair and determining the sorption from a solution of about 0.5% Pyrazol dye (Clariant) adjusted to about pH 3.5 with glacial acetic acid. (See, for example, Crawford, et al., "A Replacement for Rubine dye for detecting cationics on keratin," J. Soc. Cosm. Chem., V31, pp. 273-278 (September/October 1980), the relevant disclosures of which are incorporated by reference).

EXAMPLE 17

Hair Care Setting and Conditioning Compositions

This example illustrates the use of cationic associative polymer, Polymer AF of Example 1, Table 2A, at an active polymer weight of about 3% in aqueous hair care conditioning compositions, useful for setting, styling, and/or conditioning hair. In one study, Polymer AF was used alone, (Ex. 17A), as the sole conditioning, rheology modifying, film-forming hair-fixative polymer. In additional studies, Polymer AF was used in combination with an active polymer weight of about 3% of a commercial nonionic auxiliary hair-fixative polymer (Exs. 17B-17D); an active polymer weight of about 3% of a commercial cationic auxiliary hair-fixative polymer (Exs. 17E-17L); an active polymer weight of about 1% or 3% of a commercial amphoteric auxiliary hair-fixative polymer (Exs. 17M and 17N, respectively); or an active polymer weight of about 1% or about 3% of a commercial auxiliary cationic conditioning polymer (Exs. 17O-17T), in the aqueous formulation and in the amounts shown in Table 18.

TABLE 18

| Ingredients (INCI/Trade Name) | Wt. % |
|---|---|
| 1. Polymer AF, Ex. 1 (active wt. %) | 3 |
| 2. Water, deionized, to 100% | q.s. |
| 3. Commercial polymer (active wt. %), identified in Table 18A | |
| Exs. 17B-17L, 17N-17S | 3 |
| Ex. 17M, Ex. 17T | 1 |
| 4. Preservative | q.s. |
| 5. Glycolic acid (50%) to pH 4-6 | q.s. |

Each of the compositions was prepared by dispersing in water the commercial auxiliary polymer ingredient no. 3 indicated in Table 18A and mixing to provide an aqueous polymer solution, Polymer AF was then admixed into the aqueous polymer solution, the pH was adjusted to about 5 with ingredient no. 5, ingredient no. 4 was then added and the pH adjusted with ingredient no. 5 to a range of about 4 to about 6, as needed. The appearance of the composition was noted, and after 24 hours, the Brookfield viscosity was measured, as well as turbidity, clarity, and hair setting efficacy, where measured, as discussed below. Unless indicated otherwise, the HHCR hair setting efficacy was calculated from the average values of 9 hair tresses/composition studied. The viscosity, turbidity and clarity results, where measured, are shown in Table 18A.

TABLE 18A

| Ex. No. | Commercial Polymer (INCI/Tradename) | Viscosity mPa·s | Turbidity NTU | Clarity % T |
|---|---|---|---|---|
| 17A | None Polymer AF, Ex. 1 | 66,000 | 16.9 | — |
| 17B | PVP (Note 20) | 68,400 | 31.3 | — |
| 17C | PVP (Note 21) | 70,100 | 11.6 | — |
| 17D | PVP/VA (Note 22) | 75,000 | 38.2 | 65 |
| 17E | Polyquaternium-11 (Note 10, Table 7) | 16,700 | 44.5 | 60.1 |
| 17F | Polyquaternium-11 (Note 23) | 13,700 | 51.6 | — |
| 17G | Polyquaternium-28 (Note 24) | 27,350 | 59.3 | 51.5 |
| 17H | Polyquaternium-4 (Note 25) | 66,200 | 36.4 | 65.9 |
| 17I | Polyquaternium-16 (Note 26) | 3,800 | 116 | 23 |
| 17J | Polyquaternium-46 (Note 27) | 14,900 | 76.5 | — |
| 17K | Polyquaternium-55 (Note 28) | 22,600 | 37.1 | 69 |
| 17L | Gaffix VC-713 (Note 29) | 27,950 | 24.2 | — |
| 17M | Amphomer ® (Note 30) | 71,400 | opaque | — |
| 17N | Diaformer Z-731 (Note 31) | 12,200 | 38.1 | — |
| 17O | Polyquaternium-10 (Note 32) | 34,000 | 94 | 23.5 |
| 17P | Polyquaternium-39 (Note 33) | 4,670 | opaque | — |
| 17Q | Polyquaternium-7 (Note 34) | 7,400 | 96.3 | 21 |
| 17R | Jaguar ® Excel (Note 35) | 150,000 | 49.3 | — |
| 17S | Chitosan PCA (Note 36) | 19,500 | 192 | 2 |
| 17T | Polyquaternium-10 (Note 37) | 82,400 | 53.9 | — |

Notes to Table 18A
Note 20. PVP K90, BASF (weight average molecular weight reportedly about 1,300,000 Daltons).
Note 21. PVP K30, BASF (weight average molecular weight reportedly about 60,000 Daltons).
Note 22. PVP 73W, BASF.
Note 23. Gafquat ® 734N, ISP, supplied as 50% in ethanol.
Note 24. Gafquat ® HS-100, ISP.
Note 25. Celquat ® H-100, National Starch.
Note 26. Luviquat ® FC-370, BASF.
Note 27. Luviquat ® Hold, BASF.
Note 28. Styleze ® W20, ISP.
Note 29. Trade name for a cationic fixative polymer having the INCI name vinylcaprolactam/PVP/dimethylaminoethylmethacrylate copolymer sold by ISP.
Note 30. Trade name for an amphoteric polymer having the INCI name octylacryamide/acrylates/butylaminoethylmethacrylate copolymer, sold by National Starch.
Note 31. Trade name for an amphoteric polymer, supplied as 40% in ethanol, having the INCI name Arcylates/Lauryl Acrylate/Stearyl Acrylate/Ethylamine Oxide Metharcylate Copolymer sold by Clariant.
Note 32. UCARE ® Polymer JR-400, Amerchol.
Note 33. Merquat ® 3330, Ondeo Nalco.
Note 34. Mackernium ™ 007, McIntyre Group, Ltd.
Note 35. Trade name for a quaternized guar derivative having the INCI name, Guar hydroxypropyltrimonium chloride, sold by Rhodia.
Note 36. Kytamer ® PC, Amerchol.
Note 37. Celquat ® SC-230M, National Starch & Chemical.

EX. 17A. The aqueous composition containing Polymer AF as the sole conditioning, fixative polymer had a pH of about 4.1, was a clear gel, and, surprisingly, provided excellent hair setting efficacy (HHCR of 70% was about 4 hours, and HHCR at about 8 hours was about 57%).

Exs. 17B-17D. The aqueous compositions containing Polymer AF and the commercial nonionic polymer, PVP (Ex. 17B, 17C) or PVP/VA (Ex. 17D) had a pH in the range of about 4.3 to about 5.5, and were substantially clear gels. The hair setting efficacy of the composition of Ex. 17B was judged very good (HHCR of 70% for at least about 3 hours, and HHCR at about 8 hours was about 52%). The composition containing the combination of Polymer AF and PVP or PVP/VA (Ex. 17C and Ex. 17D) provided good to weak hair setting efficacy (HHCR of 70% was less than 1 hour, and HHCR at about 8 hours was about 27 to about 31%), making these compositions more suitable for temporary grooming or shaping of hair than for hair holding. Ex. 17D was judged relatively stiff and suitable for achieving novelty hair shapes.

Exs. 17E-17. The compositions containing Polymer AF and commercial cationic fixative polymers had a pH in the range of about 4.1 to about 4.4. The compositions of Exs. 17E, 17F, 17H, 17K, and 17L were substantially clear. The composition of Ex. 17E provided excellent hair setting efficacy (HHCR of 70% or more for at least about 8 hours), and the composition of Ex. 17K provided excellent hair efficacy for up to about 24 hours (HHCR of 91% for at least about 8 hours, and 88% at about 24 hours), and the texture of the compositions was judged aesthestically smooth. The composition of Ex. 17l provided very good hair setting efficacy (HHCR of 70% for more than 1 hour but less than about 2 hours) and the texture of the composition was judged relatively stiff. The composition of Ex. 17H was translucent and smooth textured and provided excellent hair setting efficacy (HHCR of about 96% or more for up to about 24 hours). The composition of Ex. 17J had a high viscosity, was visibly turbid (slightly cloudy), and provided excellent hair setting efficacy (HHCR of 70% for at least about 7 hours, and an HHCR of about 64% at 8 hours).

Exs. 17M-17N. The gel compositions containing Polymer AF and amphoteric polymer had a pH of about 4.2 and about 4.4. The composition of Ex. 17M had a viscosity of about 71,400 mPa·s, was opaque and provided good to weak hair setting efficacy (HHCR of 70% of less than one hour, and 37% at about 8 hours). The composition of Ex. 17N had a viscosity of about 12,200 mPa·s, and was a smooth, substantially clear gel (turbidity of about 38 NTU).

Exs. 17O-17T. The compositions of Exs. 17O-17T containing Polymer AF and cationic conditioning polymers had a pH of about 4.2 to about 4.3. The composition of Ex. 17O was a turbid, tacky gel, which provided excellent hair setting efficacy (HHCR of more than 90% for up to about 24 hours), making it suitable for use for specialty or novelty hair styles and where high hold is desired. The compositions of Ex. 17P had a high viscosity, was opaque, and provided excellent hair setting efficacy (HHCR of more than 90% for up to about 24 hours). The composition of Ex. 17Q had a high viscosity, was smooth, and provided very good hair setting efficacy (HHCR of 70% or more for at least 2 hours, and an HHCR of about 51% at 8 hours). The composition of Ex. 17R was a thick, substantially clear gel. The composition of Ex. 17S was a turbid, dark-colored gel judged suitable for use where product clarity is not a concern. The composition of Ex. 17T was a substantially clear gel.

Hydroalcoholic Compositions.

In a second study, the formulations of Exs. 17A-17T were prepared as hydroalcoholic compositions by repeating the procedure described above, except that, in step 1, the commercial polymers were dispersed in a mixture of ethanol SD-40 and water, so that the final hydroalcoholic hair care composition contained about 10 weight percent ethanol. The alcohol decreased the viscosity of all the compositions, except for Exs. 17O and 17S, as discussed below.

Ex. 17A. The hydroalcoholic composition containing Polymer AF (Ex. 17A) again was a substantially clear gel (turbidity of about 21.4 NTU) of slightly lower viscosity (about 34,100 mPa·s) and provided excellent hair setting efficacy (HHCR of 70% increased to about 5 hours).

Exs. 17B-17D. The alcohol decreased the viscosity of the compositions of Exs. 17B, 17C, and 17D to a range of about 38,550 mPa·s (Ex. 17C) to about 47,000 mPa·s (Ex. 17D), and increased clarity (turbidity was in a range of about 26.3 NTU (Ex. 17C) to about 28 NTU (Ex. 17B), and the clarity of Ex. 17D increased to about 71.1% T). The hair setting efficacy of Ex. 17B increased to excellent (HHCR of 70% was about 5 hours).

Exs. 17E-17L. The alcohol decreased the viscosity of the compositions of Exs. 17E, 17F, 17H, 17K, and 17L but were still gels (viscosity was in the range of about 10,300 mPa·s (Ex. 17F) to about 51,200 mPa·s (Ex. 17H), and remained substantially clear (turbidity was in the range of about 26.5

NTU (Ex. 17L) to about 36 NTU (Ex. 17E), and the clarity of the compositions of Exs. 17E, 17H, and 17K, respectively increased to about 65.5, 76.6 and 71% T). The excellent hair setting efficacy of the composition of Ex. 17E was unchanged by the presence of the alcohol (HHCR of 70% was about 8 hours). The inclusion of alcohol in the composition of Ex. 17G produced a substantially clear gel having a viscosity of about 21,400 mPa·s, a turbidity of about 40 NTU, and a clarity of about 62% T. The inclusion of alcohol in the composition of Ex. 17I produced a medium viscosity of about 2,880 mPa·s, and improved clarity (turbidity decreased to about 68 NTU, and clarity increased to about 35% T). The inclusion of alcohol in the composition of Ex. 17G produced a gel having a viscosity of about 13,950 mPa·s, and improved clarity (turbidity decreased to about 66.2 NTU).

Exs. 17M-17N. The alcohol decreased the viscosity of the gel compositions of Ex. 17M to about 35,000 mPa·s. The alcohol decreased the viscosity of the composition of Ex. 17N to a high viscosity of about 7,460 mPa·s and increased clarity (turbidity decreased to about 26.4 NTU).

Exs, 17O-17T. The hydroalcoholic composition of Ex. 17O had a slightly increased viscosity and improved clarity (viscosity was about 38,100 mPa·s, turbidity was about 67 NTU, and clarity was about 30% T). The hydroalcoholic composition of Ex. 17P had a slightly increased viscosity of about 7,000 mPa·s, was opaque, and retained its excellent hair setting efficacy (HHCR of 24 hours). The alcohol in the composition of Ex. 17Q decreased the viscosity and improved the clarity (viscosity was about 5,100 mPa·s, turbidity was about 52.3 NTU, and clarity was about 57% T). The alcohol in the composition of Ex. 17R decreased the viscosity and improved the clarity slightly (viscosity was about 120,000 mPa·s, turbidity was about 40.4 NTU). The alcohol in the composition of Ex. 17S increased the viscosity and turbidity (viscosity was about 32,000 mPa·s, turbidity was about 235 NTU, and clarity was about 1.7% T). In the hydroalcoholic composition of Ex. 17T, the alcohol decreased the viscosity slightly to about 72,400 mPa·s and further improved clarity (turbidity decreased to about 40.9 NTU).

EXAMPLE 18

Hair Conditioner Compositions

This example illustrates the use of cationic associative polymer, Polymer Y of Example 1, Table 2, in hair conditioner compositions, at an active polymer weight of about 2% as the sole conditioning agent (Ex. 18A), and in combination with an added dimethicone copolyol (Exs. 18B, 18C), and in combination with both added dimethicone copolyol and quaternary ammonium compound (Exs. 18D, 18E) in the amounts shown in Table 19.

TABLE 19

| | Weight % | | | | |
|---|---|---|---|---|---|
| Ingredient (INCI/Tradename) | EX. 18A | EX. 18B | EX. 18C | EX. 18D | EX. 18E |
| 1. Deionized, Water, to 100% | q.s. | q.s. | q.s. | q.s. | q.s. |
| 2. Propylene glycol | 2 | 2 | 2 | — | — |
| 3. Varisoft Clear (Active Weight %) (Note 2, Table 4) | — | — | — | 0.6 | 0.3 |
| 4. Polyquaternium-39 (Note 32, Table 18A) | — | — | — | 2.5 | — |
| 5. PEG-7 Glycerylcocoate (Note 38) | 3 | 3 | 3 | 2 | 2 |
| 6. Glycerin | 3 | 3 | 3 | 2 | 2 |
| 7. Polymer Y, Ex. 1 (Active Weight %) | 2 | 2 | 2 | 2 | 2 |
| 8. D-Panthenol | 2 | 2 | 2 | 1 | 1 |
| 9. PEG-12 Dimethicone (Note 39) | — | 1 | 3 | 1 | 1 |
| 10. Preservative | q.s. | q.s. | q.s. | q.s. | q.s. |
| 11. Chelating Agent | q.s. | q.s. | q.s. | q.s. | q.s. |
| 12. Glycolic acid (50%) to pH | q.s. | q.s. | q.s. | q.s. | q.s. |
| 13. Fragrance | q.s. | q.s. | q.s. | q.s. | q.s. |
| Brookfield Viscosity (mPa · s) | — | — | 9,500 | 4,060 | 3,360 |

Note 38 Cetiol HE, Cognis
Note 39 Dow Corning 193, Dow Corning

The compositions were prepared by gently admixing Polymer Y and water, partially neutralizing the polymer solution with ingredient no. 12 to a pH of about 5, then admixing the remaining ingredients in the order listed, and adjusting the pH to about 4 as needed with Ingredient No. 12.

The composition of Ex. 18C was substantially clear (turbidity of 16.5 NTU) determined before the addition of the fragrance. The composition of Ex. 18D was substantially clear (turbidity of about 5.45 NTU, freshly prepared and about 13.9 NTU after 24 hours). The composition of Ex. 18E was substantially clear when freshly prepared (turbidity of 24.4 NTU), becoming opaque after 24 hours (turbidity 109.2 NTU).

EXAMPLE 19

Cationic Conditioner Compositions

This example illustrates the compatibility of various concentrations of the cationic associative polymer, Polymer W, of Example 1, with various cationic quaternary ammonium compounds in the formulations and amounts shown in Table 20.

TABLE 20

| | Weight % | | | | | |
|---|---|---|---|---|---|---|
| Ingredient (INCI/Tradename) | EX. 19A | EX. 19B | EX. 19C | EX. 19D | EX. 19E | EX. 19F |
| Part A | | | | | | |
| 1. Deionized Water to 100% | q.s. | q.s. | q.s. | q.s. | q.s. | q.s. |
| 2. Polymer W, Ex. 1 | 1 | 1 | 0.6 | 0.3 | 0.3 | 0.3 |
| 3. Propylene glycol | 2.5 | 2.5 | 2.5 | 2.5 | 2.5 | 2.5 |
| 4. CTAC (Note 40) | 1 | — | 1 | 1 | — | — |
| 5. Quaternium-18 (Note 5, Table 4) | — | 1 | — | — | — | — |
| 6. BTAC (Note 41) | — | — | — | — | 1 | — |
| 7. Quaternium-31 (Note 6, Table 4) | — | — | — | — | — | 1 |

TABLE 20-continued

| Ingredient (INCI/Tradename) | Weight % | | | | | |
|---|---|---|---|---|---|---|
| | EX. 19A | EX. 19B | EX. 19C | EX. 19D | EX. 19E | EX. 19F |
| Part B | | | | | | |
| 8. Cetyl alcohol | 2.2 | 2.2 | 1.1 | 1.1 | 1.1 | 1.1 |
| 9. Stearyl alcohol | 1.25 | 1.25 | 0.63 | 0.63 | 0.63 | 0.63 |
| 10. Hydrogenated Vegetable Oil (Note 42) | 1.2 | 1.2 | 0.6 | 0.6 | 0.6 | 0.6 |
| 11. Caprylic/capric triglyceride (Note 43) | 3.4 | 3.4 | 1.68 | 1.68 | 1.68 | 1.68 |
| Part C | | | | | | |
| 12. Preservative | q.s. | q.s. | q.s. | q.s. | q.s. | q.s. |
| Part D | | | | | | |
| 13. Citric Acid (10%) to pH 4-4.4 | q.s. | q.s. | q.s. | q.s. | q.s. | q.s. |
| Brookfield Viscosity (mPa · s) | 25,000-35,000 | 19,000-21,000 | 7,400 | 4,000 | 7,700 | 850 |

Notes to Table 20
Note 40. CTAC refers to Cetrimonium chloride described in Example 2.
Note 41. BTAC refers to the quaternary ammonium compound having the INCI name Behentrimonium chloride, assigned to N,N,N-trimethyl-1-docosaminium chloride.
Note 42. INCI name for a product sold under the tradename WECOBEE ® S by the Stepan Company.
Note 43. INCI name for product sold under the tradename NEOBEE ® M-5 by the Stepan Company.

The compositions were manufactured as follows. Part A was prepared by gradually dispersing Polymer W (Ingredient No. 2) into water with moderate mixing agitation and mixing until a clear solution resulted. The remaining ingredients of Part A were then added and the mixture was heated to a temperature in the range of about 65 to about 70° C. In a separate vessel, Part B was prepared by admixing the ingredients of Part B and heating the mixture to a temperature in the range of about 65 to about 70° C., mixing until a solid-free homogeneous mixture was obtained. Part B was then added to Part A with moderate mixing agitation and mixed until homogeneous (about 15 minutes). The resulting mixture was then cooled to a temperature in the range of about 35 to about 40° C. Part C was then added and the pH was adjusted to a range of about 4 to about 4.4 by adding Part D, as needed.

All of the compositions had a pH in the range of about 4 (Ex. 19F) and about 4.2 (Ex. 19B), and each composition had a glossy white, creamy appearance. The viscosity of the compositions ranged from thin (Ex. 19F), to high (Exs. 19C, 19D and 19E) to gels (Ex. 19A, 19B).

EXAMPLE 20

Sanitizer Compositions

This example illustrates the use of cationic associative Polymers, Polymer W (Ex. 20A) and Polymer Y (Exs. 20B, 20C, 20D, and 20E) in alcohol-free, antimicrobial, sanitizer formulations and in the active amounts shown in Table 21.

| Ingredient (INCI/Trade Name) | Weight % Active | | | | |
|---|---|---|---|---|---|
| | Ex. 20A | Ex. 20B | Ex. 20C | Ex. 20D | Ex. 20E |
| 1. Water, dionized, to 100% | q.s. | q.s. | q.s. | q.s. | q.s. |
| 2a. Polymer W, Ex. 1 | — | — | — | — | 2 |
| 2b. Polymer Y, Ex. 1 | 1 | 1.5 | 1.75 | 2 | — |
| 3. Benzethonium Chloride (Note 44) | 0.3 | 0.3 | 0.3 | 0.3 | 0.3 |

-continued

| Ingredient (INCI/Trade Name) | Weight % Active | | | | |
|---|---|---|---|---|---|
| | Ex. 20A | Ex. 20B | Ex. 20C | Ex. 20D | Ex. 20E |
| 4. Glycolic Acid (50% to pH | q.s. | q.s. | q.s. | q.s. | q.s. |
| 5. PEG-33 (and) PEG-8 Dimethicone (and) PEG-14 (Note 45) | — | 1 | — | 2 | — |
| pH Before addition of Dimethicone Copolyol | 4.6 | 4.4 | 4.5 | 4.6 | 4.4 |
| Brookfield viscosity, mPa · s, Immediate | 1,400 | 4,500 | 10,200 | 14,650 | 8,560 |
| Turbidity (NTU) After addition of Dimethicone Copolyol | 7.2 | 8.6 | 8.8 | 8.8 | 4.4 |
| Brookfield viscosity, mPa · s | — | 6,500 | — | 9,880 | — |

Notes to Table 20
Note 44. INCI name for Diisobutylphenoxyethoxyethyldimethylbenzylammonium chloride monohydrate sold under the tradename LONZAGARD ® by Lonza, Inc.
Note 45. INCI name for a product sold by Noveon, Inc.

The compositions were prepared by admixing ingredient no. 3 with ingredient no. 1 at ambient room temperature until homogeneous (about 15 minutes), then adding ingredient no. 2, and admixing until homogenous, adjusting the pH with ingredient no.4 to a range of about 4.4 to about 4.7 and then measuring the pH, viscosity and turbidity values. Ingredient no. 5 was then added to the formulation of Exs. 20B and 20D, as indicated in Table 21, and the viscosity again measured. The polymer emulsion of Polymer W of Example 1 had a total polymer solids of about 20.9% by weight and the polymer emulsion of Polymer Y of Example 1 had a total polymer solids of about 20.7% by weight.

The compositions were judged suitable as sanitizing compositions, and particularly suitable as hand sanitizers.

EXAMPLE 21

Instrumental Hair Combing

The wet combing properties of the hair conditioner compositions of Examples 18A, 18B, and 18C were instrumentally evaluated using the well known Texture Analyzer (Texture Technology Corp.) instrument fitted with a hard rubber comb, and combing was carried out at a temperature of about 23° C. and ambient humidity of about 50% RH. A tress of bleached European, natural brown, human hair was dampened with deionized water, about 2 grams of a conditioner was evenly applied by hand and distributed with the thumb and forefinger through the hair tress for about one minute, and then the tress was rinsed with lukewarm tap water for about 30 seconds. The rinsed wet tress was then secured by the A/TG tensile grip of the Texture Analyzer instrument and combed by raising the tensile grip to pull the hair through the fine-tooth section of the comb at a rate of about 3 mm/s until the full length of the tress had been completely passed through. The work force (grams) needed to raise the tress was recorded as a function of distance. The comb-through procedure was repeated four times on the same tress, for a total of five comb-through pulls. For baseline measurement, each hair tress was measured five times for comb-through before applying test composition, and measurements were repeated after applying test composition, and averaged for % total work force.

Polymer Y (Ex. 18A) was judged as providing wet combing conditioning, and ease of combing was further improved by the presence of a dimethicone copolyol (Exs. 18B, 18C). The wet combing data showed that conditioning was substantially equivalent from the compositions of Ex. 18B and 18C, and both compositions provided easier wet combing than the composition of Ex. 18A.

EXAMPLE 22

Acidic Surfactant Skin Cleanser

This example illustrates the compatibility of Polymer AF of Example 1, with anionic surfactants in an acidic surfactant skin cleanser formulation, containing an amphoteric hydroxy complex of alpha-hydroxy acid (Lactic acid) and L-Arginine.

TABLE 22

| Ingredient<br>INCI/Trade Name | Wt % |
|---|---|
| 1. Water, deionized, to 100% | q.s. |
| 2. Glycol Distearate(and)Glycerine(and)Laureth-4 (and)Cocamidopropyl Betaine (Note 46) | 1 |
| 3. Coco-Glucoside(and)Glyceryl Oleate (Note 47) | 2 |
| 4. Cocamidopropylamine Oxide (Note 48) | 1 |
| 5. Sodium Laureth Sulfate(and)Cocamidopropyl Betaine(and)Polyglucoside (Note 49) | 23.5 |
| 6. Lactic Acid(and)L-Arginine blend (Note 50) | 10 |
| 7. Sodium Hydroxide (50%) to pH | q.s. |
| 8. Preservative | q.s. |
| 9. Polymer AF, Ex. 1 (Active Weight %) | 1 |

Note 46. INCI name for product sold under the tradename Euperlan ® PK-3000 by Cognis.
Note 47. INCI name for product sold under the tradename Lamesoft ® PO-65 (65%) by Cognis.
Note 48. INCI name for product sold under the tradename Standamox ® CAW by Cognis.
Note 49. INCI name for the product sold under the tradename Texapon ® 611 (42.8%) by Cognis.
Note 50. INCI name for the product sold under the tradename AHCare ® L-65 by Cognis.

The composition was prepared by dispersing in water, ingredients nos. 2 through 6 in the order shown, mixing well between each addition. The pH of the admixture was adjusted to a range of about 3.8 to about 3.9 with ingredient no. 7. Ingredient no. 8 was then added, followed by Polymer AF (no. 9), and the pH was then adjusted with ingredient no. 7 to a range of about 4.1 to about 4.2 as needed.

The finished composition had a pH of about 4.1 and a Brookfield viscosity of about 5,640 mPa·s. The composition was judged particularly suitable as a body cleanser, typically referred to as a body wash.

EXAMPLE 23

Mousse Formulation

TABLE 23

| Ingredient<br>INCI/Trade Name | Wt. %<br>(as supplied) |
|---|---|
| 1. Water, deionized, to 100% | q.s. |
| 2. Polymer AF, Ex. 1 (Active Polymer Weight) | 0.5 |
| 3. Polyquaternium 11 (20% solids) | 20 |
| 4. SD alcohol | 6 |
| 5. Cocamidopropyl betaine (35%) | 0.5 |
| 6. PEG 40 Hydrogenated Castor Oil | 0.3 |
| 7. Citric Acid (50%) to pH | q.s. |
| 8. Preservative | q.s. |
| 9. Fragrance | q.s. |

Polymer AF was dispersed into deionized water. Ingredient nos. 3, 4, and 5 were then added in the order listed, mixing after each addition until uniform. Ingredient no. 8 was added and mixed until the batch was uniform. Ingredients nos. 6 and 9 were premixed and added to the foregoing batch. The pH was adjusted to about 5 with citric acid. The formulation was judged suitable for use in a mousse product.

EXAMPLE 24

Shampoos for Color Treatment and Color Maintenance

This example illustrates two shampoos (24A and 24B) suitable for color treatment and color maintenance.

TABLE 24

| Ingredient (INCI/Trade Name) | WT. % AS SUPPLIED | |
|---|---|---|
| | 24A | 24B |
| 1. Water, deionized, to 100% | q.s. | q.s. |
| 2. Polymer AF, Ex. 1 (Active Polymer Wt. %) | 1 | 1 |
| 3. Sodium Laureth Sulfate (Note 51) | 20 | 20 |
| 4. Lamesoft ® PO-65 (Note 47, Table 22) | 3 | 3 |
| 5. Cocamidopropyl Betaine | 5.5 | 5.5 |
| 6. Ammonium Laureth Sulfate (Note 52) | 15 | 15 |
| 7. Euperlan ® PK-3000 (Note 46, Table 22) | 3 | 3 |
| 8. Tocopherol | 0.1. | 0.1. |
| 9. Preservative | q.s. | q.s. |
| 10. Sodium cocoyl hydrolyzed wheat (Note 53) | 0.5 | 0.5 |
| 11. C.I. Brown 17 (Note 54a) | 0.13 | — |
| 12. C.I. Blue 99 (Note 54b) | 0.13 | — |
| 13. C.I. Red 76 (Note 54c) | 0.2 | — |

TABLE 24-continued

| | WT. % AS SUPPLIED | |
|---|---|---|
| Ingredient (INCI/Trade Name) | 24A | 24B |
| 14. Fragrance | q.s. | q.s. |
| 15. Citric Acid (50%) to pH | q.s. | q.s. |

Note 51.
INCI name for product sold under the tradename Standapol ® ES-2 by Cognis.
Note 52.
INCI name for product sold under the tradename Stanvapol ® EA-2 by Cognis.
Note 53.
INCI name for product sold under the tradename Gluadin ® WK sold by Cognis.
Note 54.
INCI name for (a) Arianor ® Sienna Brown (b); Arianor ® Steel Blue (c): Arianor ® Madder Red, all sold by Warner Jenkinson Europe, Ltd.

Shampoo 24A was prepared by dispersing Polymer AF in the deionized water with gentle mixing, adding ingredient nos. 3 and 6 with mixing, partially neutralizing the mixture to pH of about 5 with citric acid, and then adding the remaining ingredient nos. 4, 5, 7, 8, 9 and 10 in the order listed. A blend of ingredient nos. 11, 12, 13 and fragrance was added into the mixture, and the pH adjusted to a range of about 4.7 to about 5.0 with ingredient no. 15.

Shampoo 24A was judged suitable for coloring the hair during use, and for maintaining the hair color through continued use as a treatment shampoo.

Shampoo 24B was prepared following the procedure of Shampoo 24A, except that no colorant dyes were present. Shampoo 24B was judged suitable for washing hair that has been colored or chemically treated without removing the color from the hair.

From the foregoing examples, it can be seen that the present inventive polymers can be used in a wide variety of different aqueous compositions and are compatible with cationic quaternary ammonium salts, cationic surfactants and anionic surfactants. The foregoing discussion and reported studies are intended to be illustrative of the present invention and are not to be taken as limiting. Still other variants within the spirit and scope of this invention are possible and will readily present themselves to those skilled in the art.

We claim:

1. A polymer that is the product of polymerization of a monomer mixture comprising:
   a) least one amino-substituted vinyl monomer;
   b) at least one hydrophobic nonionic vinyl monomer;
   c) least one associative vinyl monomer; and
   d) at least one semihydrophobic vinyl surfactant monomer;

wherein said at least one associative vinyl monomer (c) is selected from at least one monomer represented by formula (III):

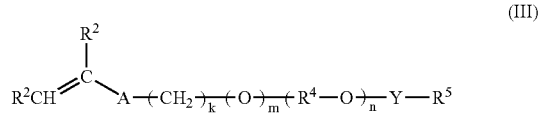

(III)

wherein, each $R^2$ is independently selected from hydrogen, methyl, —C(O)OH, and —C(O)OR$^3$; $R^3$ is selected from $C_1$-$C_{30}$ alkyl; A is selected from —CH$_2$C(O)O—, —C(O)O—, —O—, —CH$_2$O—, —NHC(O)NH—, —C(O)NH—, —Ar—(CE$_2$)$_z$—NHC(O)O—, —Ar—(CE$_2$)$_z$—NHC(O)NH—, and —CH$_2$CH$_2$NHC(O)—; Ar is a divalent aryl; E is selected from hydrogen and methyl; z is 0 or 1 ; k is an integer in the range of 0 to about 30, and m is 0 or 1, with the proviso that when k is 0, m is 0, and when k is in the range of 1 to about 30, m is 1; ($R^4$—O)$_n$ is a polyoxyalkylene, which can be a homopolymer, a random copolymer, or a block copolymer of $C_2$-$C_4$ oxyalkylene units, wherein $R^4$ is —C$_2$H$_4$—, —C$_3$H$_6$—, or —C$_4$H$_8$—, or a mixture thereof, and n is an integer in the range of about 5 to about 250; Y is selected from —R$^4$O—, —R$^4$NH—, —C(O)—, —C(O)NH—, —R$^4$NHC(O)NH—, and —C(O)NHC(O)—; and R$^5$ is a substituted or unsubstituted alkyl selected from $C_8$-$C_{40}$ linear alkyl, $C_8$-$C_{40}$ branched alkyl, $C_8$-$C_{40}$ carbocyclic alkyl, a $C_2$-$C_{40}$ alkyl-substituted phenyl, an aryl-substituted $C_2$-$C_{40}$ alkyl, and $C_8$-$C_{80}$ complex ester; wherein the R$^5$ alkyl group optionally having one or more substituents selected from a hydroxyl group, an alkoxy group, and a halogen group; and wherein said at least one semihydrophobic vinyl surfactant monomer (d) is selected from at least one monomer represented by formulas (IV) or (V) and combinations thereof:

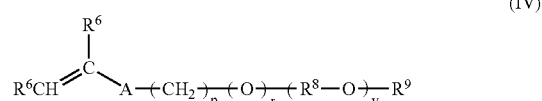

(IV)

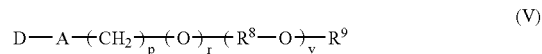

(V)

wherein, in each of formulas (IV) and (V), each $R^6$ is independently selected from hydrogen, $C_1$-$C_{30}$ alkyl, —C(O)OH, and —C(O)OR$^7$; $R^7$ is selected $C_1$-$C_{30}$ alkyl; A is selected from —CH$_2$C(O)O—, —C(O)O—, —O—, —CH$_2$O—, —NCH(O)NH—, —C(O)NH—, —Ar—(CE$_2$)$_z$—NHC(O)O—, —Ar—(CE$_2$)$_z$—NHC(O)NH—, and —CH$_2$CH$_2$NHC(O)—; Ar is a divalent aryl; E is selected from hydrogen and methyl; z is 0 or 1; p is an integer in the range of 0 to about 30, and r is 0 or 1, with the proviso that when p is 0, r is 0, and when p is in the range of 1 to about 30, r is 1; ($R^8$—O)$_v$ is a polyoxyalkylene, which can be a homopolymer, a random copolymer or a block copolymer of $C_2$-$C_4$ oxyalkylene units, wherein $R^8$ is —C$_2$H$_4$—, —C$_3$H$_6$—, —C$_4$H$_8$—, or a mixture thereof, and v is an integer in the range of about 5 to about 250; R$^9$ is selected from hydrogen and $C_1$-$C_4$ alkyl; and D is selected from $C_8$-$C_{30}$ unsaturated alkyl, and carboxy-substituted $C_8$-$C_{30}$ unsaturated alkyl.

2. The polymer of claim 1 wherein the amino-substituted vinyl monomer is selected from:
   a mono-($C_1$-$C_4$)alkylamino($C_1$-$C_8$)alkyl (meth)acrylate,
   a di-($C_1$-$C_4$)alkylamino($C_1$-$C_8$)alkyl (meth)acrylate,
   a mono-($C_1$-$C_4$)alkylamino($C_1$-$C_8$)alkyl (meth)acrylamide,
   a di-($C_1$-$C_4$)alkylamino($C_1$-$C_8$)alkyl (meth)acrylamide,
   a nitrogen-containing heterocyclic (meth)acrylamide,
   a nitrogen-containing heterocyclic (meth)acrylate, and a mixture thereof.

3. The polymer of claim 1 wherein the hydrophobic nonionic vinyl monomer is selected from a compound of the formulas (I), (II), and combinations thereof:

(I)

(II)

wherein, in each of formulas (I) and (II), X is H or methyl; and Z is —C(O)OR$^1$, —C(O)NH$_2$, —C(O)NHR$^1$, —C(O)N(R$^1$)$_2$, —C$_6$H$_4$R$^1$, —C$_6$H$_4$OR$^1$, —C$_6$H$_4$Cl, —CN, —NHC(O)CH$_3$, —NHC(O)H, N-(2-pynolidonyl), N-caprolactamyl, —C(O)NHC(CH$_3$)$_3$, —C(O)NHCH$_2$CH$_2$—N-ethyleneurea, —SiR$_3$, —C(O)O(CH$_2$)$_x$SiR$_3$, —C(O)NH(CH$_2$)$_x$SiR$_3$, or —(CH$_2$)$_x$SiR$_3$; x is an integer in the range of 1 to about 6; each R is independently C$_1$-C$_{30}$ alkyl; each R$^1$ is independently C$_1$-C$_{30}$ alkyl, hydroxy-substituted C$_2$-C$_{30}$ alkyl or halogen-substituted C$_1$-C$_{30}$ alkyl.

4. The polymer of claim 1 wherein the hydrophobic nonionic vinyl monomer is a C$_1$-C$_{30}$ alkyl ester of acrylic acid, a C$_1$-C$_{30}$ alkyl ester of methacrylic acid, or a mixture thereof.

5. The polymer of claim 1 wherein the polyoxyalkylene group is a homopolymer, a random copolymer, or a block copolymer comprising about 5 to about 250 C$_2$-C$_4$ oxyalkylene units.

6. A polymer of claim 1 that is the product of polymerization of a monomer mixture comprising, on a total monomer mixture weight basis:
(a) about 10 to about 70 weight percent of at least one amino-substituted vinyl monomer or a salt thereof;
(b) about 20 to about 80 weight percent of at least one hydrophobic nonionic vinyl monomer;
(c) about 0.01 to about 25 weight percent of at least one associative vinyl monomer;
(d) about 0.01 to about 25 weight percent of at least one semihydrophobic vinyl surfactant monomer;
(e) up to about 10 weight percent of a hydroxy-substituted nonionic vinyl monomer;
(f) up to about 5 weight percent of a crosslinking monomer;
(g) up to about 10 weight percent of a chain transfer agent; and
(h) up to about 2 weight percent of a polymeric stabilizer.

7. The polymer of claim 6 wherein the amino-substituted vinyl monomer is selected from:
a mono-(C$_1$-C$_4$)alkylamino(C$_1$-C$_8$)alkyl (meth)acrylate,
a di-(C$_1$-C$_4$)alkylamino(C$_1$-C$_8$)alkyl (meth)acrylate,
a mono-(C$_1$-C$_4$)alkylamino(C$_1$-C$_8$)alkyl (meth)acrylamide,
a di-(C$_1$-C$_4$)alkylainino(C$_1$-C$_8$)alkyl (meth)acrylamide,
a nitrogen-containing heterocyclic (meth)acrylamide,
a nitrogen-containing heterocyclic (meth)acrylate, and a mixture thereof.

8. The polymer of claim 6 wherein the hydrophobic nonionic vinyl monomer is selected from a compound of the formulas (I), (II), and combinations thereof:

$$CH_2=C(X)Z, \qquad (I)$$

$$CH_2=CH-OC(O)R; \qquad (II)$$

wherein, in each of fonnulas (I) and (II), X is H or methyl; and Z is —C(O)OR$^1$, —C(O)NH$_2$, —C(O)NHR$^1$, —C(O)N(R$^1$)$_2$, —C$_6$H$_4$R$^1$, —C$_6$H$_4$OR$^1$, —C$_6$H$_4$Cl, —CN, —NHC(O)CH$_3$, —NHC(O)H, N-(2-pyrrolidonyl), N-caprolactamnyl, —C(O)NHC(CH$_3$)$_3$, —C(O)NHCH$_2$CH$_2$—N-ethyleneurea, —SiR$_3$, —C(O)O(CH$_2$)$_x$SiR$_3$, —C(O)NH(CH$_2$)$_x$SiR$_3$, or —(CH$_2$)$_x$SiR$^3$; x is an integer in the range of 1 to about 6; each R is independently C$_1$-C$_{30}$ alkyl; each R$^1$ is independently C$_1$-C$_{30}$ alkyl, hydroxy-substituted C$_2$-C$_{30}$ alkyl or halogen-substituted C$_1$-C$_{30}$ alkyl.

9. The polymer of claim 6 wherein the hydrophobic nonionic vinyl monomer is a C$_1$-C$_{30}$ alkyl ester of acrylic acid, a C$_1$-C$_{30}$ alkyl ester of methacrylic acid, or a mixture thereof.

10. The polymer of claim 7 wherein said monomers are selected from:
(b) about 50 to about 65 weight percent of at least one hydrophobic nonionic vinyl monomer selected from a C$_1$-C$_{30}$ alkyl ester of acrylic acid, a C$_1$-C$_{30}$ alkyl ester of methacrylic acid, and a mixture thereof;
(c) about 0.1 to about 10 weight percent of at least one associative vinyl monomer selected from cetyl polyethoxylated methacrylate, cetearyl polyethoxylated methacrylate, stearyl polyethoxylated (meth)acrylate, arachidyl polyethoxylated (meth)acrylate, behenyl polyethoxylated methacrylate, lauryl polyethoxylated methacrylate, cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate, hydrogenated castor oil polyethoxylated methacrylate, canola polyethoxylated (meth)acrylate, and cholesterol polyethoxylated methacrylate;
(d) about 0.1 to about 10 weight percent of at least one semihydrophobic vinyl surfactant monomer is selected from a compound represented by one of the following chemical formulas and combinations thereof:

$$CH_2=CH-O(CH_2)_aO(C_3H_6O)_b(C_2H_4O)_eH;$$

$$CH_2=CHCH_2O(C_3H_6O)_d(C_2H_4O)_eH;$$

wherein a is 2, 3, or 4; b is an integer in the range of 1 to about 10; c is an integer in the range of about 5 to about 50; d is an integer in the range of 1 to about 10; and e is an integer in the range of about 5 to about 50;
(e) up to about 10 weight percent of a hydroxy-substituted nonionic vinyl monomer;
(f) up to about 5 weight percent of a crosslinking monomer;
(g) up to about 10 weight percent of a chain transfer agent; and
(h) up to about 2 weight percent of a polymeric stabilizer.

11. The polymer of claim 6 wherein the associative vinyl monomer is selected from cetyl polyethoxylated methacrylate, cetearyl polyethoxylated methacrylate, steamyl polyethoxylated (meth)acrylate, arachidyl polyethoxylated (meth)acrylate, behenyl polyethoxylated methacrylate, lauryl polyethoxylated methacrylate, cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate, hydrogenated castor oil polyethoxylated methacrylate, canola polyethoxylated (meth)acrylate, and cholesterol polyethoxylated methacrylate, and a mixture thereof.

12. The polymer of claim 10 wherein the polyoxyalkylene group in said semihydrophobic monomer is a homopolymer, a random copolymer, or a block copolymer having about 5 to about 250 C$_2$-C$_4$ oxyalkylene units.

13. The polymer of claim 6 wherein the monomer mixture includes a semihydrophobic vinyl surfactant monomer is selected from a compound represented by one of the following chemical formulas and combinations thereof:

$$CH_2=CH-O(CH_2)_aO(C_3H_6O)_b(C_2H_4O)_eH;$$

$$CH_2=CHCH_2O(C_3H_6O)_d(C_2H_4O)_eH;$$

wherein a is 2, 3, or 4; b is an integer in the range of 1 to about 10; c is an integer in the range of about 5 to about 50; d is an integer in the range of 1 to about 10; and e is an integer in the range of about 5 to about 50.

14. The polymer of claim 6 wherein the monomer mixture comprises about 0.01 to about 10 weight percent of at least one hydroxy-substituted nonionic vinyl monomer, based on the total monomer mixture weight.

15. The polymer of claim 14 wherein the hydroxy-substituted nonionic vinyl monomer is selected from a hydroxy-substituted($C_1$-$C_4$)alkyl acrylate, a hydroxy-substituted($C_1$-$C_4$)alkyl methacrylate, hydroxy-substituted($C_1$-$C_4$)alkyl acrylamide, a hydroxy-substituted($C_1$-$C_4$)alkyl methacrylamide, and a mixture thereof.

16. The polymer of claim 14 wherein the hydroxy-substituted nonionic vinyl monomer is 2-hydroxyethyl methacrylate.

17. The polymer of claim 6 wherein the monomer mixture contains about 0.01 to about 3 weight percent of at least one crosslinking monomer, based on the total monomer mixture weight.

18. The polymer of claim 17 wherein the crosslinking monomer is an acrylate ester of a polyol having at least two acrylate ester groups, a methacrylate ester of a polyol having at least two methacrylate ester groups or a combination thereof.

19. The polymer of claim 6 wherein the monomer mixture contains at least about 0.1 weight percent of a chain transfer agent, based on the total monomer mixture weight.

20. The polymer of claim 19 wherein the chain transfer agent is selected from a thio compound, a disulfide compound, a phosphite, a hypophosphite, a haloalkyl compound, and a combination thereof.

21. A polymer that is the product of polymerization of a monomer mixture comprising, on a total monomer mixture weight basis:
  (a) about 20 to about 50 weight percent of at least one amino-substituted vinyl monomer selected from:
  3-(N,N-dimethylamino)propyl (meth)acrylate,
  N'-(3-N,N-dimethylamino)propyl (meth)acrylamide.
   2-(N,N-dimethylamnino)ethyl methacrylate,
   2-(N,N-diethylamino)ethyl methacrylate,
   2-(tert-butylamino)ethyl methacrylate,
   2-(N,N-dimethylamino)propyl methacrylamide, and
   2-(N,N-dimethylaminO)neopentyl acrylate.
  (b) about 50 to about 65 weight percent of at least one hydrophobic nonionic vinyl monomer selected from a $C_1$-$C_{30}$ alkyl ester of acrylic acid, a $C_1$-$C_{30}$ alkyl ester of methacrylic acid, and a mixture thereof;
  (c) about 0.1 to about 10 weight percent of at least one associative vinyl monomer selected from cetyl polyethoxylated methacrylate, cetearyl polyethoxylated methacrylate, steamyl polyethoxylated (meth)acrylate, arachidyl polyethoxylated (meth)acrylate, behenyl polyethoxylated methacrylate, lauryl polyethoxylated methacrylate, cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate, hydrogenated castor oil polyethoxylated methacrylate, canola polyethoxylated (meth)acrylate, and cholesterol polyethoxylated methacrylate;
  (d) about 0.1 to about 10 weight percent of at least one semihydrophobic vinyl surfactant monomer is selected from a compound represented by one of the following chemical formulas and combinations thereof:

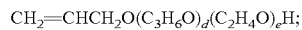

wherein a is 2, 3, or 4; b is an integer in the range of 1 to about 10; c is an integer in the range of about 5 to about 50; d is an integer in the range of 1 to about 10; and e is an integer in the range of about 5 to about 50;
  (e) up to about 10 weight percent of a hydroxy-substituted nonionic vinyl monomer;
  (f) up to about 5 weight percent of a crosslinking monomer;
  (g) up to about 10 weight percent of a chain transfer agent; and
  (h) up to about 2 weight percent of a polymeric stabilizer.

22. The polymer of claim 21 wherein the monomer mixture comprises about 1 to about 5 weight percent of at least one hydroxy-substituted nonionic vinyl monomer, based on the total monomer mixture weight.

23. The polymer of claim 22 wherein the hydroxy-substituted nonionic vinyl monomer is selected from a hydroxy-substituted($C_1$-$C_4$)alkyl acrylate, a hydroxy-substituted($C_1$-$C_4$)alkyl methacrylate, hydroxy-substituted($C_1$-$C_4$)alkyl acrylamide, and a hydroxy-substituted($C_1$-$C_4$)alkyl methacrylamide, and a mixture thereof.

24. The polymer of claim 22 wherein the hydroxy-substituted nonionic vinyl monomer is 2-hydroxyethyl methacrylate.

25. The polymer of claim 21 wherein the monomer mixture comprises about 0.01 to about 3 weight percent of a crosslinking monomer, based on the total monomer mixture weight.

26. The polymer of claim 25 wherein the crosslinking monomer is an acrylate ester of a polyoi having at least two acrylate ester groups, a methacrylate ester of a polyol having at least two methacrylate ester groups or a niixture thereof.

27. The polymer of claim 21 wherein the monomer mixture comprises at least about 0.1 percent by weight of a chain transfer agent, based on the total monomer mixture weight.

28. The polymer of claim 27 wherein the chain transfer agent is selected from a thio compound, a disulfide compound, a phosphite, a hypophosphite, a haloalkyl compound, and a mixture thereof.

29. The polymer of claim 1 wherein the at least one semihydrophobic vinyl surfactant monomer is selected from a compound represented by one of the following chemical formulas and combinations thereof:

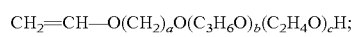

wherein a is 2, 3, or 4; b is an integer in the range of 1 to about 10; c is an integer in the range of about 5 to about 50; d is an integer in the range of 1 to about 10; and e is an integer in the range of about 5 to about 50.

* * * * *